United States Patent
Alcaraz et al.

(10) Patent No.: US 7,129,246 B2
(45) Date of Patent: Oct. 31, 2006

(54) N-ADAMANTLMETHYL DERIVATIVES AND INTERMEDIATES AS PHARMACEUTICAL COMPOSITIONS AND PROCESSES FOR THEIR PREPARATION

(75) Inventors: Lilian Alcaraz, Loughborough (GB); Timothy Johnson, Loughborough (GB); Michael Stocks, Loughborough (GB)

(73) Assignee: AstraZeneca AB, Sodertalje (SE)

( * ) Notice: Subject to any disclaimer, the term of this patent is extended or adjusted under 35 U.S.C. 154(b) by 261 days.

(21) Appl. No.: 10/495,711

(22) PCT Filed: Nov. 12, 2002

(86) PCT No.: PCT/SE02/02057

§ 371 (c)(1),
(2), (4) Date: May 14, 2004

(87) PCT Pub. No.: WO03/041707

PCT Pub. Date: May 22, 2003

(65) Prior Publication Data

US 2005/0010052 A1    Jan. 13, 2005

(30) Foreign Application Priority Data

Nov. 16, 2001  (SE) .................... 0103836

(51) Int. Cl.
| A61K 31/435 | (2006.01) |
| A61K 31/44 | (2006.01) |
| C07D 211/72 | (2006.01) |
| C07D 213/72 | (2006.01) |
| C07D 211/70 | (2006.01) |

(52) U.S. Cl. .............. 514/277; 514/352; 514/353; 514/357; 546/296; 546/297; 546/300; 546/301

(58) Field of Classification Search ............. 546/296, 546/297, 300, 301; 514/277, 352, 357
See application file for complete search history.

(56) References Cited

U.S. PATENT DOCUMENTS

| 3,464,998 A | 9/1969 | Krimmel ............... 260/295.5 |
| 3,471,491 A | 10/1969 | Venkatachala et al. ... 260/249.9 |
| 4,751,292 A | 6/1988 | Fox ........................ 536/24 |

FOREIGN PATENT DOCUMENTS

| BE | 650919 A | 7/1964 |
| DE | 1943404 A | 12/1970 |
| EP | 0002065 A1 | 5/1979 |
| EP | 0867436 A1 | 9/1998 |
| WO | 90/10622 | * 9/1990 |
| WO | WO 95/04720 | 2/1995 |
| WO | WO 99/29660 | 6/1999 |
| WO | WO 99/29661 | 6/1999 |
| WO | WO 00/61569 | 10/2000 |
| WO | WO 01/94338 A1 | 12/2001 |
| WO | WO 03/080579 | 10/2003 |

OTHER PUBLICATIONS

Costakis et al., "Synthesis of Some Adamantane Derivatives of 2-Aminobenzothiazoles", *Journal of Medicinal Chemistry* 14(12):1222-1223 (1971).

Ho et al., "Synthesis of a Peptidomimetic Tricyclic Tetrahydrobenzo[*ij*] quinoline as a VLA-4 Antagonist", *J. Org. Chem.* 65:6743-6748, p. 6745, scheme 5, (27) (2000).

STN International, File REGISTRY, see RN 405068-97-5, 405070-41-9, 405076-22-4, Apr. 14, 2002.

STN International, File REGISTRY, see RN 445032-09-7, Aug. 30, 2002.

STN International, File CHEMCATS, Accession No. 2001:48444, May 14, 2001, NS18552, 2-Quinolinecarboxamide, N-(tricycle[3.3.1.13,7]dec-1-ylmethyl), CAS Registry No. 313688-07-2.

STN International, File REGISTRY, see RN 401622-10-4, Mar. 24, 2002.

* cited by examiner

*Primary Examiner*—James O. Wilson
*Assistant Examiner*—Binta Robinson
(74) *Attorney, Agent, or Firm*—Fish & Richardson P.C.

(57) ABSTRACT

The invention provides compounds of general formula (I) in which m, A, $R^1$ and Ar have the meanings defined in the specification; a process for, and intermediates used in, their preparation; pharmaceutical compositions containing them; a process for preparing the pharmaceutical compositions; and their use in therapy.

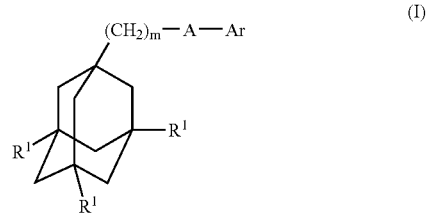

19 Claims, No Drawings

N-ADAMANTLMETHYL DERIVATIVES AND INTERMEDIATES AS PHARMACEUTICAL COMPOSITIONS AND PROCESSES FOR THEIR PREPARATION

CROSS-REFERENCE TO RELATED APPLICATIONS

This application is the national phase application under 35 U.S.C. § 371 of PCT International Application No. PCT/SE02/02057, filed Nov. 12, 2002, which claims priority to Swedish Application Serial No. 0103836-3, filed Nov. 16, 2001.

The present invention relates to adamantane derivatives, processes for their preparation, pharmaceutical compositions containing them, a process for preparing the pharmaceutical compositions, and their use in therapy.

The $P2X_7$ receptor (previously known as P2Z receptor), which is a ligand-gated ion channel, is present on a variety of cell types, largely those known to be involved in the inflammatory/immune process, specifically, macrophages, mast cells and lymphocytes (T and B). Activation of the $P2X_7$ receptor by extracellular nucleotides, in particular adenosine triphosphate, leads to the release of interleukin-1β (IL-1β) and giant cell formation (macrophages/microglial cells), degranulation (mast cells) and proliferation (T cells), apoptosis and L-selectin shedding (lymphocytes). $P2X_7$ receptors are also located on antigen-presenting cells (APC), keratinocytes, salivary acinar cells (parotid cells), hepatocytes and mesangial cells.

It would be desirable to make compounds effective as $P2X_7$ receptor antagonists for use in the treatment of inflammatory, immune or cardiovascular diseases, in the aetiologies of which the $P2X_7$ receptor may play a role.

In accordance with the present invention, there is therefore provided a compound of formula

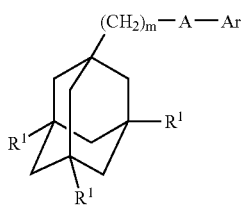
(I)

wherein m represents 1, 2 or 3, preferably 1 or 2;
each $R^1$ independently represents a hydrogen or halogen (e.g. fluorine, chlorine, bromine or iodine) atom, preferably a hydrogen atom;
A represents C(O)NH or, preferably, NHC(O);
Ar represents a group

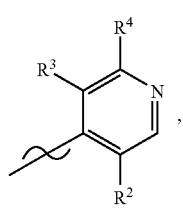
(II)

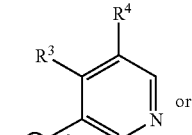
(III)
or

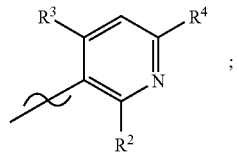
(IV)

one of $R^2$ and $R^3$ represents halogen, nitro, amino, hydroxyl, or a group selected from (i) $C_1$–$C_6$ alkyl optionally substituted by at least one halogen atom, (ii) $C_3$–$C_8$ cycloalkyl, (iii) $C_1$–$C_6$ alkoxy optionally substituted by at least one halogen atom, and (iv) $C_3$–$C_8$ cycloalkyloxy, and the other of $R^2$ and $R^3$ represents a hydrogen or halogen atom;
$R^4$ represents a group

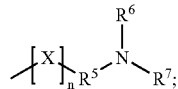
(V)

X represents an oxygen or sulphur atom or a group >N—$R^8$;
n is 0 or 1;
$R^5$ represents a $C_1$–$C_5$ alkyl group which may be optionally substituted by at least one substituent selected from hydroxyl, halogen and $C_1$–$C_6$ alkoxy;
$R^6$ and $R^7$ each independently represent a hydrogen atom, $C_1$–$C_6$ alkyl (optionally substituted by at least one substituent selected from hydroxyl, halogen, $C_1$–$C_6$ alkoxy, and (di)-$C_1$–$C_4$ alkylamino (itself optionally substituted by at least one hydroxyl group)), or $C_3$–$C_8$ cycloalkyl (optionally substituted by at least one substituent selected from hydroxyl, halogen and $C_1$–$C_6$ alkoxy); and
$R^8$ represents a hydrogen atom or a $C_1$–$C_5$ alkyl group which may be optionally substituted by at least one substituent selected from hydroxyl, halogen and $C_1$–$C_6$ alkoxy;
with the provisos that:
(a) when n is 0, then A is NHC(O), and
(b) when n is 1, X represents oxygen and A is C(O)NH, then $R^6$ and $R^7$ do not both simultaneously represent a hydrogen atom or do not both simultaneously represent an unsubstituted $C_1$–$C_6$ alkyl, or when one of $R^6$ and $R^7$ represents a hydrogen atom, then the other of $R^6$ and $R^7$ does not represent an unsubstituted $C_1$–$C_6$ alkyl; and
(c) when n is 1, X is oxygen, sulphur or >NH and A is NHC(O), then $R^6$ and $R^7$ do not both simultaneously represent a hydrogen atom or do not both simultaneously represent an unsubstituted $C_1$–$C_6$ alkyl, or when one of $R^6$ and $R^7$ represents a hydrogen atom, then the other of $R^6$ and $R^7$ does not represent an unsubstituted $C_1$–$C_6$ alkyl or —$CH_2CH_2OH$;

or a pharmaceutically acceptable salt or solvate thereof.

In one embodiment of the invention, there is provided a compound of formula

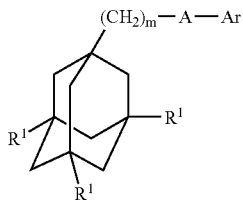

(I)

wherein m represents 1, 2 or 3, preferably, 1 or 2;
each $R^1$ independently represents a hydrogen or halogen (e.g. fluorine, chlorine, bromine or iodine) atom, preferably a hydrogen atom;
A represents C(O)NH or, preferably, NHC(O);
Ar represents a group

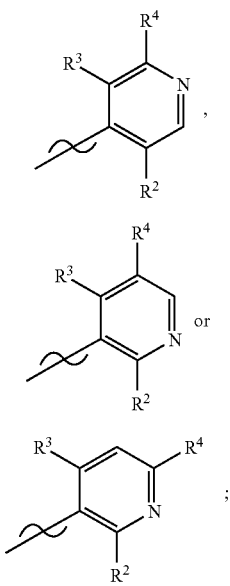

one of $R^2$ and $R^3$ represents halogen, nitro, amino, hydroxyl, or a group selected from (i) $C_1$–$C_6$ alkyl optionally substituted by at least one halogen atom, (ii) $C_3$–$C_8$ cycloalkyl, (iii) $C_1$–$C_6$ alkoxy optionally substituted by at least one halogen atom, and (iv) $C_3$–$C_8$ cycloalkyloxy, and the other of $R^2$ and $R^3$ represents a hydrogen or halogen atom;
$R^4$ represents a group

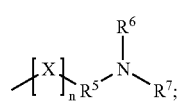

X represents an oxygen or sulphur atom or a group >N—$R^8$;
n is 0 or 1;
$R^5$ represents a $C_1$–$C_5$ alkyl group which may be optionally substituted by at least one substituent selected from hydroxyl, halogen and $C_1$–$C_6$ alkoxy; and $R^6$, $R^7$ and $R^8$ each independently represent a hydrogen atom or a $C_1$–$C_5$ allyl group which may be optionally substituted by at least one substituent selected from hydroxyl, halogen and $C_1$–$C_6$ alkoxy;
with the provisos that:
(d) when n is 0, then A is NHC(O), and
(e) when n is 1, X represents oxygen and A is C(O)NH, then $R^6$ and $R^7$ do not both simultaneously represent a hydrogen atom or do not both simultaneously represent an unsubstituted $C_1$–$C_5$ alkyl, or when one of $R^6$ and $R^7$ represents a hydrogen atom, then the other of $R^6$ and $R^7$ does not represent an unsubstituted $C_1$–$C_5$ alkyl, and
(f) when n is 1, X is oxygen, sulphur or >NH and A is NHC(O), then $R^6$ and $R^7$ do not both simultaneously represent a hydrogen atom or do not both simultaneously represent an unsubstituted $C_1$–$C_5$ alkyl, or when one of $R^6$ and $R^7$ represents a hydrogen atom, then the other of $R^6$ and $R^7$ does not represent an unsubstituted $C^1$–$C_5$ alkyl or —$CH_2CH_2OH$;

or a pharmaceutically acceptable salt or solvate thereof.

In the context of the present specification, unless otherwise indicated, an alkyl substituent or alkyl moiety in a substituent group may be linear or branched. Examples of alkyl groups/moieties containing up to 6 carbon atoms include methyl, ethyl, n-propyl, isopropyl, n-butyl, isobutyl, tert-butyl, n-pentyl, n-hexyl and combinations of any two or more thereof. The alkyl groups in a di-$C_1$–$C_4$ alkylamino substituent group may be the same or different. Further, it should be appreciated that in the definition of $R^5$, if the at least one optional substituent is a hydroxyl or alkoxy group, it will not be attached to a carbon atom adjacent either to —X— or to —$NR^6R^7$. Similarly, in the definitions of $R^6$, $R^7$ and $R^8$, a hydroxyl or alkoxy moiety should not be attached to a carbon atom which is adjacent to a nitrogen atom.

In an embodiment of the invention, Ar represents a group of formula (II) or (III).

In another embodiment of the invention, Ar represents a group of formula (II).

One of $R^2$ and $R^3$ represents a halogen (e.g. fluorine, chlorine, bromine or iodine), nitro, amino (—$NH_2$), hydroxyl, or a group selected from (i) $C_1$–$C_6$ alkyl, preferably $C_1$–$C_4$ alkyl, optionally substituted by at least one (e.g. one, two, three or four) halogen atom(s) as defined above, (ii) $C_3$–$C_8$ cycloalkyl (e.g. cyclopropyl, cyclobutyl, cyclopentyl or cyclohexyl), (iii) $C_1$–$C_6$ alkoxy, preferably $C_1$–$C_4$ alkoxy, optionally substituted by at least one (e.g. one, two, three or four) halogen atom(s) as defined above, and (iv) $C_3$–$C_8$ cycloalkyloxy (e.g. cyclopropyloxy, cyclobutyloxy, cyclopentyloxy or cyclohexyloxy), and the other of $R^2$ and $R^3$ represents a hydrogen or halogen atom as defined above.

In one embodiment of the invention, one of $R^2$ and $R^3$ represents a halogen (such as a chlorine or bromine) atom and the other of $R^2$ and $R^3$ represents a hydrogen atom.

In an embodiment of the invention, n is 0.

$R^5$ represents a $C_1$–$C_5$ (e.g. $C_1$–$C_3$) alkyl group which may be optionally substituted by at least one substituent (e.g. one, two, three or four substituents independently) selected from hydroxyl, halogen (e.g. fluorine, chlorine, bromine or iodine) and $C_1$–$C_6$, preferably $C_1$–$C_4$, alkoxy (e.g. methoxy, ethoxy, n-propoxy, n-butoxy, n-pentoxy, n-hexoxy and combinations of any two or more thereof).

In an embodiment of the invention, $R^5$ represents —$CH_2$—, —$(CH_2)_2$—, —$(CH_2)_3$— or —$CH_2CH(OH)$$CH_2$—.

$R^6$ and $R^7$ each independently represent:
(i) a hydrogen atom, (ii) $C_1$–$C_6$, preferably $C_1$–$C_5$, alkyl optionally substituted by at least one substituent (e.g. one, two, three or four substituents independently) selected from hydroxyl, halogen (e.g. fluorine, chlorine, bromine or iodine), $C_1$–$C_6$, preferably $C_1$–$C_4$, alkoxy (e.g. methoxy, ethoxy, n-propoxy, n-butoxy, n-pentoxy, n-hexoxy and combinations of any two or more thereof), and (di)-$C_1$–$C_4$, preferably $C_1$–$C_2$, alkylamino (itself optionally substituted by at least one, e.g. one or two, hydroxyl group(s)), or (iii) $C_3$–$C_8$ cycloalkyl optionally substituted by at least one substituent (e.g. one, two, three or four substituents independently) selected from hydroxyl, halogen (e.g., fluorine, chlorine, bromine or iodine) and $C_1$–$C_6$, preferably $C_1$–$C_4$, alkoxy (e.g. methoxy, ethoxy, n-propoxy, n-butoxy, n-pentoxy, n-hexoxy and combinations of any two or more thereof).

In an embodiment of the invention, $R^6$ and $R^7$ each independently represent:

(i) a hydrogen atom, (ii) $C_1$–$C_5$ alkyl optionally substituted by at least one substituent (e.g. one, two or three substituents independently) selected from hydroxyl and (di)-$C_1$–$C_4$, preferably $C_1$–$C_2$, alkylamino (itself optionally substituted by at least one, e.g. one or two, hydroxyl group(s)), or (iii) $C_5$–$C_6$ cycloalkyl optionally substituted by at least one, e.g. one or two, hydroxyl group(s).

$R^8$ represents a hydrogen atom or a $C_1$–$C_5$, preferably $C_1$–$C_3$, alkyl group which may be optionally substituted by at least one substituent (e.g. one, two, three or four substituents independently) selected from hydroxyl, halogen (e.g. fluorine, chlorine, bromine or iodine) and $C_1$–$C_6$, preferably $C_1$–$C_4$, alkoxy (e.g. methoxy, ethoxy, n-propoxy, n-butoxy, n-pentoxy, n-hexoxy and combinations of any two or more thereof).

In an embodiment of the invention, $R^8$ represents a hydrogen atom or a $C_1$–$C_3$ alkyl group which may be optionally substituted by at least one, e.g. one or two, hydroxyl group(s).

In another embodiment of the invention, $R^6$, $R^7$ and $R^8$ each independently represent a hydrogen atom or a $C_1$–$C_5$ (e.g. $C_1$–$C_3$) alkyl group which may be optionally substituted by at least one substituent (e.g. one, two, three or four substituents independently) selected from hydroxyl, halogen (e.g. fluorine, chlorine, bromine or iodine) and $C_1$–$C_6$ alkoxy (e.g. methoxy, ethoxy, n-propoxy, n-butoxy, n-pentoxy, n-hexoxy and combinations of any two or more thereof.

In a further embodiment of the invention, $R^6$, $R^7$ and $R^8$ each independently represent a hydrogen atom or a $C_1$–$C_5$ (e.g. $C_1$–$C_3$) alkyl group optionally substituted by at least one, e.g. one, two or three, hydroxyl group (s) such as —$CH_3$, —$C_2H_5$, —$CH(CH_3)_2$, —$CH_2OH$, —$(CH_2)_2OH$, —$(CH_2)_3OH$, —$CH(CH_3)CH_2OH$, —$CH_2CH(CH_3)OH$, —$CH_2CH(OH)CH_3$, —$CH_2CH(OH)CH_2OH$, —$CH_2C(CH_3)_2OH$, —$CH(isopropyl)CH_2OH$, —$CH(CH_2OH)_2$, or —$CH_2C(CH_3)_2CH_2OH$.

In an embodiment of the invention, there is provided a subset of compounds of formula (I), and pharmaceutically acceptable salts and solvates thereof, in which:

m represents 1;

each $R^1$ represents a hydrogen atom;

A represents NHC(O);

Ar represents a group

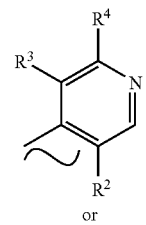

or

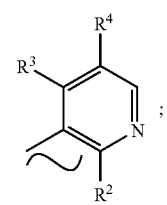

one of $R^2$ and $R^3$ represents a halogen atom, and the other of $R^2$ and $R^3$ represents a hydrogen atom;

$R^4$ represents a group

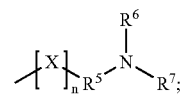

X represents an oxygen or sulphur atom or a group >N—$R^8$;

n is 0 or 1;

$R^5$ represents a $C_1$–$C_3$ alkyl group optionally substituted by at least one hydroxyl group;

$R^6$ and $R^7$ each independently represent a hydrogen atom, $C_1$–$C_5$ alkyl (optionally substituted by one or two substituents independently selected from hydroxyl and (di)-$C_1$–$C_2$ alkylamino (itself optionally substituted by at least one hydroxyl group)), or $C_6$ cycloalkyl (substituted by at least one hydroxyl group);

$R^8$ represents a hydrogen atom or a $C_2$ alkyl group substituted by at least one hydroxyl group; and subject to the provisos (a), (b) and (c) mentioned above.

In another embodiment of the invention, there is provided a further subset of compounds of formula (I), and pharmaceutically acceptable salts and solvates thereof in which:

m represents 1;

each $R^1$ represents a hydrogen atom;

A represents NHC(O);

Ar represents a group

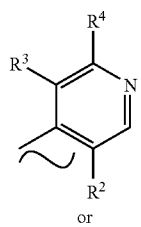

or

-continued $$\text{(III)}$$

one of $R^2$ and $R^3$ represents a halogen atom, and the other of $R^2$ and $R^3$ represents a hydrogen atom;

$R^4$ represents a group $$\text{(V)}$$

X represents an oxygen or sulphur atom or a group >N—$R^8$;
n is 0 or 1;
$R^5$ represents a $C_2$–$C_3$ alkyl group optionally substituted by at least one hydroxyl group;
$R^6$ and $R^7$ each independently represent a hydrogen atom or a $C_1$–$C_5$ alkyl group optionally substituted by one or two hydroxyl groups;
$R^8$ represents a hydrogen atom or a $C_2$ alkyl group substituted by at least one hydroxyl group; and
subject to the provisos (d), (e) and (f) mentioned above.

Examples of compounds of the invention include:

N-(1-Adamantylmethyl)-5-chloro-2-{3-[(3-hydroxypropyl)-amino]propyl}isonicotinamide, N-(1-Adamantylmethyl)-5-chloro-2-{3-[(3-hydroxypropyl)amino]propyl}-isonicotinamide dihydrochloride, N-(1-Adamantylmethyl)-2-chloro-5-{3-[(3-hydroxypropyl)amino]propyl}nicotinamide, N-(1-Adamantylmethyl)-2-chloro-5-(3-{[(1S)-2-hydroxy-1-methylethyl]amino}propyl)nicotinamide, N-(1-Adamantylmethyl)-2-chloro-5-(3-{[(1R)-2-hydroxy-1-methylethyl]amino}propyl)nicotinamide, N-(1-Adamantylmethyl)-2-(3-aminopropyl)-5-chloroisonicotinamide hydrochloride, N-(1-Adamantylmethyl)-5-chloro-2-[3-(ethylamino)propyl]isonicotinamide hydrochloride, N-(1-Adamantylmethyl)-5-chloro-2-({2-[(3-hydroxypropyl)amino]-ethyl}thio)isonicotinamide hydrochloride, N-(1-Adamantylmethyl)-5-chloro-2-(3-{[(1R)-2-hydroxy-1-methylethyl]amino}propyl)isonicotinamide, dihydrochloride, N-(1-Adamantylmethyl)-5-chloro-2-(3-{[(1S)-2-hydroxy-1-methylethyl]amino}propyl)isonicotinamide, dihydrochloride, N-(1-Adamantylmethyl)-5-chloro-2-{3-[(2-hydroxyethyl)amino]propyl}-isonicotinamide hydrochloride, N-(1-Adamantylmethyl)-5-chloro-2-{2-[(3-hydroxypropyl)amino]ethoxy}isonicotinamide, hydrochloride N-(1-Adamantylmethyl)-5-chloro-2-({2-[(2-hydroxyethyl)amino]ethyl}-amino)isonicotinamide dihydrochloride, N-(1-Adamantylmethyl)-5-chloro-2-[3-(isopropylamino)propyl]isonicotinamide dihydrochloride, N-(1-Adamantylmethyl)-5-chloro-2-(3-{[(2S)-2-hydroxypropyl]amino}propyl)isonicotinamide, dihydrochloride, N-(1-Adamantylmethyl)-5-chloro-2-(3-{[(2R)2,3-dihydroxypropyl]amino}propyl)isonicotinamide, dihydrochloride, N-(1-Adamantylmethyl)-5-chloro-2-(3-{[(2S)-2,3-dihydroxypropyl]amino}propyl)isonicotinamide, dihydrochloride, N-(1-Adamantylmethyl)-5-chloro-2-{3-[(4-methylcyclohexyl)amino]propyl}isonicotinamide dihydrochloride, N-(1-Adamantylmethyl)-5-chloro-2-{3-[(2-hydroxy-2-methylpropyl)amino]propyl}isonicotinamide dihydrochloride, N-(1-Adamantylmethyl)-5-chloro-2-(3-{[(1R)-1-(hydroxymethyl)-2-methylpropyl]amino}propyl)isonicotinamide, dihydrochloride, N-(1-Adamantylmethyl)-5-chloro-2-(3-{[2-(methylamino)ethyl]amino}propyl)isonicotinamide dihydrochloride, N-(1-Adamantylmethyl)-5-chloro-2-(3-{[3-(methylamino)propyl]amino}propyl)isonicotinamide bis(trifluoroacetate), N-(1-Adamantylmethyl)-5-chloro-2-[3-({2-[(2-hydroxyethyl)amino]ethyl}amino)propyl]isonicotinamide dihydrochloride, N-(1-Adamantylmethyl)-5-chloro-2-(3-{[2-(diethylamino)ethyl]amino}propyl)isonicotinamide dihydrochloride, N-(1-Adamantylmethyl)-5-chloro-2-(3-{[2-hydroxy-1-(hydroxymethyl)ethyl]amino}propyl)isonicotinamide dihydrochloride, N-(1-Adamantylmethyl)-5-chloro-2-{3-[(2-hydroxyethyl)(methyl)amino]propyl}isonicotinamide dihydrochloride, N-(1-Adamantylmethyl)-5-chloro-2-{3-[(3-hydroxy-2,2-dimethylpropyl)amino]propyl}isonicotinamide dihydrochloride, N-(1-Adamantylmethyl)-5-chloro-2-(3-{[(2R)-2-hydroxypropyl]amino}propyl)isonicotinamide, dihydrochloride, N-(1-Adamantylmethyl)-5-chloro-2-({[3-(methylamino)propyl]amino}methyl)isonicotinamide dihydrochloride, N-(1-Adamantylmethyl)-5-chloro-2-[({2-[(2-hydroxyethyl)amino]ethyl}amino)methyl]isonicotinamide dihydrochloride, N-(1-Adamantylmethyl)-5-chloro-2-({[2-(methylamino)ethyl]amino}methyl)isonicotinamide dihydrochloride, N-(1-Adamantylmethyl)-5-chloro-2-{3-[(2-hydroxyethyl)amino]ethyl}isonicotinamide dihydrochloride, N-(1-Adamantylmethyl)-5-chloro-2-{3-[(3-hydroxypropyl)amino]ethyl}isonicotinamide dihydrochloride, N-(1-Adamantylmethyl)-5-chloro-2-[3-(methylamino)propyl]isonicotinamide hydrochloride, N-(1-Adamantylmethyl)-5-bromo-2-{[(2S)-2-hydroxy-3-methylamino)propyl]oxy}isonicotinamide, N-(1-Adamantylmethyl)-2-({3-[bis(3-hydroxypropyl)amino]propyl}amino)-3-chloroisonicotinamide dihydrochloride, and all pharmaceutically acceptable salts and solvates of any one thereof.

The present invention further provides a process for the preparation of a compound of formula (I) as defined above, or a pharmaceutically acceptable salt or solvate thereof, which comprises:

(i) when n is 0 and $R^5$ represents $CH_2$, reacting a compound of formula

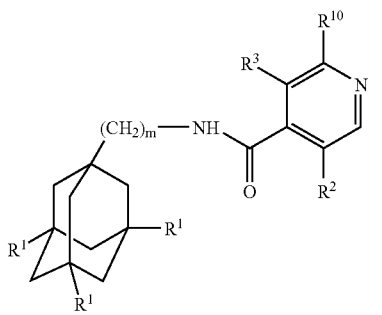

(X)

wherein R[10] represents —C(O)H or —CH$_2$L[1], L[1] represents a leaving group (e.g. halogen, paratoluene sulphonate or methane sulphonate) and m, R[1], R[2] and R[3] are as defined in formula (I), or a compound of formula

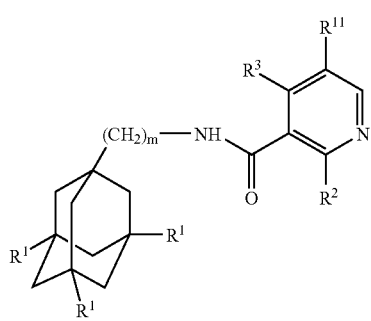

(XI)

wherein R[11] represents —C(O)H or —CH$_2$L[2], L[2] represents a leaving group (e.g. halogen, paratoluene sulphonate or methane sulphonate) and m, R[1], R[2] and R[3] are as defined in formula (I), or a compound of formula (XII)

wherein R[12] represents —C(O)H or —CH$_2$L[3], L[3] represents a leaving group (e.g. halogen, paratoluene sulphonate or methane sulphonate) and m, R[1], R[2] and R[3] are as defined in formula (I), with a compound of formula (XIII), HNR[6]R[7], wherein R[6] and R[7] are as defined in formula (I), under reductive amination conditions when R[10], R[11] or R[12] represents —C(O)H or in the presence of a suitable base R[10], R[11] or R[12] represents —CH$_2$L[1], —CH$_2$L[2] or —CH$_2$L[3]; or (ii) when n is 0, R[5] is (CH$_2$)$_2$ and R[6] and R[7] are both hydrogen, reacting a compound of formula (X) as defined in (i) above in which R[10] represents —CH$_2$L[1], or a compound of formula (X) as defined in (i) above in which R[11] represents —CH$_2$L[2], or a compound of formula (XI) as defined in (i) above in which R[12] represents —CH$_2$L[3], with an alkali metal cyanide, followed by a hydrogenation reaction; or (ii) when n is 0, R[5] is (CH$_2$)$_2$ and at least one of R[6] and R[7] is other than hydrogen, reacting a compound as prepared in (ii) above with at least one compound of formula (XIV), R[13]C(O)H, wherein R[13] represents an optionally substituted C$_1$–C$_6$ alkyl or C$_3$–C$_8$ cycloalkyl group as defined for R[6] and R[7] in formula (I), under reductive amination conditions; or (iv) when n is 0 and R[5] represents a C$_3$–C$_5$ all group optionally substituted as defined in formula (I), reacting a compound of formula (XV)

wherein R[14] represents a leaving group (e.g. halogen or trifluoromethanesulphonate) and m, R[1], R[2] and R[3] are as defined in formula (I), or a compound of formula (XVI)

wherein R[15] represents a leaving group. (e.g. halogen or trifluoromethanesulphonate) and m, R[1], R[2] and R[3] are as defined in formula (I), or a compound of formula (XVII)

wherein $R^{16}$ represents a leaving group (e.g. halogen or trifluoromethanesulphonate) and m, $R^1$, $R^2$ and $R^3$ are as defined in formula (I), with a compound of formula

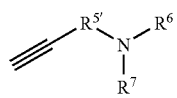
(XVIII)

wherein $R^{5'}$ represents a $C_1$–$C_3$ alkyl group optionally substituted as defined for $R^5$ in formula (I) and $R^6$ and $R^7$ are as defined in formula (I), followed by a hydrogenation reaction; or (v) when n is 0 and $R^5$ represents a $C_3$–$C_5$ alkyl group optionally substituted as defined in formula (I), reacting a compound of formula (XV), (XVI) or (XVII) as defined in (iv) above, with a compound of formula

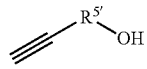
(XIX)

wherein $R^{5'}$ is as defined in formula (XVIII) in (iv) above, followed by a hydrogenation reaction and then an oxidation reaction and then by reaction with a compound of formula (XIII) as defined in (i) above under reductive amination conditions; or (vi) when n is 1 and X is oxygen or >N—$R^8$, reacting a compound of formula

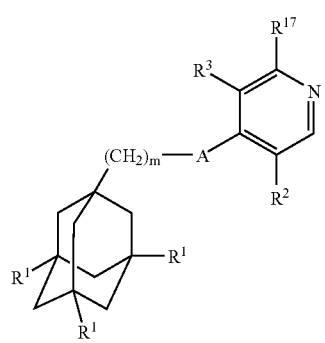
(XX)

wherein $R^{17}$ represents a leaving group (e.g. halogen or trifluoromethanesulphonate) and m, A, $R^1$, $R^2$ and $R^3$ are as defined in formula (I), or a compound of formula

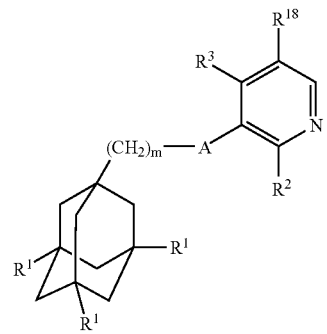
(XXI)

wherein $R^{18}$ represents a leaving group (e.g. halogen or trifluoromethanesulphonate) and m, A, $R^1$, $R^2$ and $R^3$ are as defined in formula (I), or a compound of formula

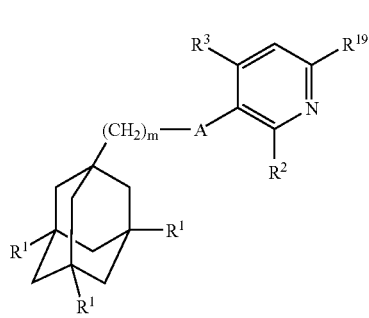
(XXII)

wherein $R^{19}$ represents a leaving group (e.g. halogen or trifluoromethanesulphonate) and m, A, $R^1$, $R^2$ and $R^3$ are as defined in formula (I), with a compound of formula

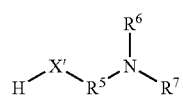
(XXIII)

wherein X' represents oxygen or >N—$R^8$ and $R^5$, $R^6$, $R^7$ and $R^8$ are as defined in formula (I); or (vii) when A is NHC(O), n is 1 and X is sulphur, reacting a compound of formula

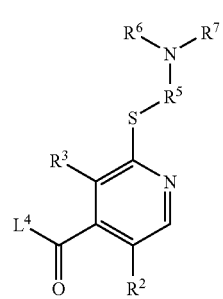
(XXIV)

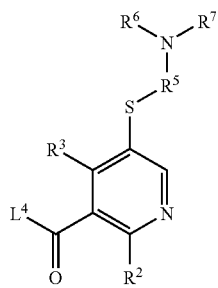

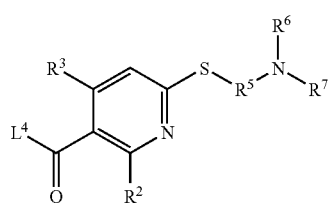

or

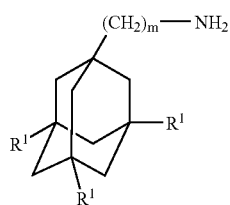

wherein, in each of formulae (XXIV), (XXV) and (XXVI), $L^4$ represents a leaving group (e.g. halogen or hydroxyl) and $R^2$, $R^3$, $R^5$, $R^6$ and $R^7$ are as defined in formula (I), with a compound of formula

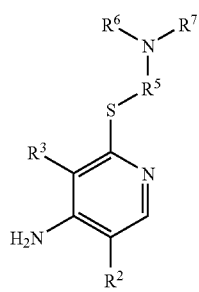

wherein m and $R^1$ are as defined in formula (I); or (viii) when A is C(O)NH, n is 1 and X is sulphur, reacting a compound of formula

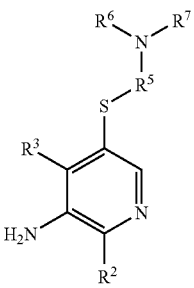

or

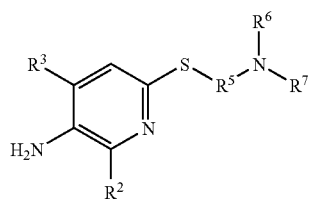

wherein, in each of formulae and (XXVIII), (XXIX) and (XXX), $R^2$, $R^3$, $R^5$, $R^6$ and $R^7$ are as defined in formula (I), with a compound of formula

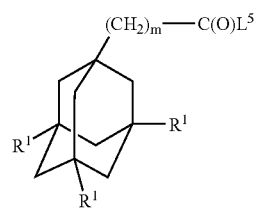

wherein $L^5$ represents a leaving group (e.g. halogen or hydroxyl) and m and $R^1$ are as defined in formula (I); or (ix) when n is 0 and $R^5$ represents a $C_2$–$C_5$ alkyl group substituted as defined in formula (I), reacting a compound of formula

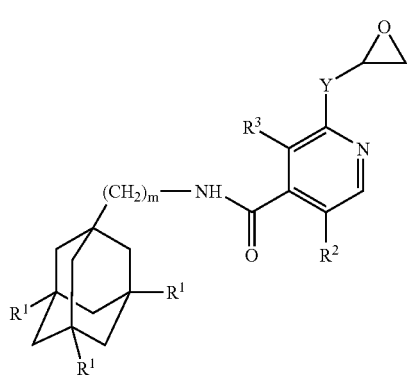

or a compound of formula

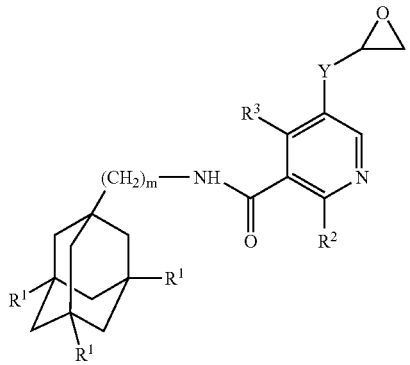

(XXXIII)

or a compound of formula

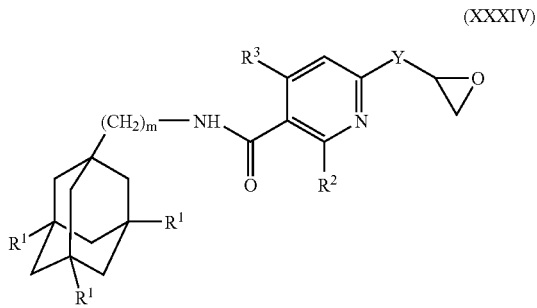

(XXXIV)

wherein, in each of formulae (XXXII), (XXXIII) and (XXXIV), Y represents a bond or a $C_1$–$C_3$ alkyl and m, $R^1$, $R^2$ and $R^3$ are as defined in formula (I), with a compound of formula (XIII) as defined in (i) above, and optionally thereafter reacting with a $C_1$–$C_6$ alkylating agent or with a halogenating agent; or (x) when n is 0 and $R^5$ represents a $C_3$–$C_5$ alkyl group optionally substituted as defined in formula (I), reacting a compound of formula (XV), (XVI) or (XVII) as defined in (iv) above, with a pre-treated compound of formula

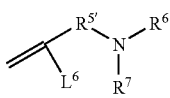

(XXXV)

in which $L^6$ represents a hydrogen atom and $R^{5'}$ represents a $C_1$–$C_3$ alkyl group optionally substituted as defined for $R^5$ in formula (I) and $R^6$ and $R^7$ are as defined in formula (I), wherein the compound of formula (XXXV) is pre-treated with a hydroborating agent; or (xi) when n is 0 and $R^5$ represents a $C_3$–$C_5$ alkyl group optionally substituted as defined in formula (I), reacting a compound of formula (XV), (XVI) or (XVII) as defined in (iv) above in the presence of a suitable catalyst such as tetrakis(triphenylphosphine)palladium, with a pre-treated compound of formula

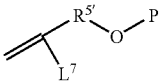

(XXXVIII)

in which $L^7$ represents a hydrogen atom and $R^{5'}$ represents a $C_1$–$C_3$ alkyl group optionally substituted as defined for $R^5$ in formula (I) and P is a suitable protecting group such as tert-butyldimethylsilyl, wherein the compound of formula (XXXVIII) is pre-treated with a hydroborating agent, followed by removal of the protecting group, P, in a deprotection reaction, then by an oxidation reaction and then by reaction with a compound of formula (XIII) as defined in (i) above under reductive amination conditions; or (xii) when n is 0 and $R^5$ is $(CH_2)_2$, reacting a compound of formula (XV), (XVI) or (XVII) as defined in (iv) above with a compound of formula

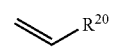

(XXXIX)

wherein $R^{20}$ represents a suitable leaving group such as trialkyltin, dialkylboron or zinc, in the presence of a suitable catalyst such as dichlorobis(triphenylphosphine) palladium, followed by reaction with a compound of formula (XIII) as defined in (i) above; or (xiii) when n is 0 and $R^5$ is $CH_2$, reacting a compound of formula (XV), (XVI) or (XVII) as defined in (iv) above with a compound of formula (XXXIX) as defined in (xii) above, followed by an oxidation reaction and then by reaction with a compound of formula (XIII) as defined in (i) above under reductive amination conditions;

and optionally after (i), (ii), (iii), (iv), (v), (vi), (vii), (viii), (ix), (x), (xi), (xii) or (xiii) carrying out one or more of the following:

converting the compound obtained to a further compound of formula (I)

forming a pharmaceutically acceptable salt or solvate of the compound.

In (i) above, the reductive amination is conveniently carried out in the presence of a reducing agent such as sodium cyanoborohydride, triacetoxyborohydride or sodium borohydride and in a polar solvent such as methanol, ethanol or dichloromethane either alone or in combination with acetic acid.

The base mentioned in (i) is conveniently potassium carbonate and the reaction employing it may be carried out in a polar solvent such as ethanol or dimethylformamide.

In process (ii), the alkali metal cyanide used may be sodium or potassium cyanide. The hydrogenation reaction is conveniently carried out using hydrogen gas and a hydrogenation catalyst such as Raney nickel.

In process (iii), the reductive amination conditions may be the same as described for (i) above.

In process (iv), the reaction with the acetylenic compound of formula (XVIII) may be carried out in the presence of catalytic bistriphenylphospine dichloride palladium (0), copper (I) iodide and a base (e.g. triethylamine) and in a solvent such as acetonitrile at ambient temperature (20° C.). The subsequent hydrogenation reaction may use hydrogen gas with a catalyst such as 5% rhodium on carbon in a solvent, for example, ethyl acetate or ethanol, and at a pressure of 3 barr.

In process (v), the reaction with the acetylenic compound of formula (XIX) and then the hydrogenation reaction can be performed by procedures analogous to those described in the previous paragraph for process (iv). The oxidation reaction can be carried out using standard oxidants (e.g. Dess-Martin periodinane or pyridinium dichromate), in a solvent such as dichloromethane. Reaction with the compound of formula (XIII) is carried out under reductive amination conditions, for example, in the presence of a reducing agent such as sodium cyanoborohydride, triacetoxyborohydride or sodium borohydride and in a polar solvent such as methanol, ethanol or dichloromethane either alone or in combination with acetic acid.

Process (vi) may be performed in a solvent such as dimethyl formamide or N-methyl-2-pyrrolidinone, using a base such as caesium carbonate, potassium carbonate or sodium hydride and at elevated temperature, e.g., $\geq 30°$ C., more particularly at a temperature in the range from 30 to 150° C., especially 100 to 150° C. A temperature of about 120° C. was found to be very effective.

Processes (vii) and (viii) are conveniently carried out in a solvent such as dichloromethane or dimethyl formamide and in the presence of carbonyl diimidazole or a coupling agent such as dicyclohexyl carbodiimide.

In process (ix), reaction with the compound of formula (XIII) may conveniently be carried out in a solvent such as N-methyl-2-pyrrolidinone using a base such as potassium carbonate at a temperature in the range from, for example, 0° C. or 20° C. to 100° C.

Subsequent reaction of the alcohol formed with a $C_1$–$C_6$ alkylating agent (e.g. a $C_1$–$C_6$ alkyl halide) may be carried out in the same solvent and in the presence of a base such as sodium hydride. Alternatively, subsequent reaction of the alcohol formed with a halogenating agent (e.g. N-bromosuccinimide or N-chlorosuccinimide with triphenylphosphine) may be carried out in a solvent such as tetrahydrofuran.

In process (x), the compound of formula (XXXV) is pre-treated by reaction with a hydroborating reagent (such as 9-borabicyclo[3.3.1]nonane or catecholborane) in a solvent (such as diethyl ether or tetrahydrofuran) at a temperature in the range from 0° C. to 80° C. (in particular from 60° C. to 70° C.) for about 2 to 3 hours, then cooling the reaction mixture to room temperature and adding a solution of a base (such as sodium hydroxide in water or tri-potassium orthophosphate in water) followed by a solution of the compound of formula (XV), (XVI) or (XVII) in a solvent (such as dimethylformamide) and a palladium catalyst (such as dichloro[1,1'-bis(diphenylphosphino)ferrocene]palladium (II) dichloromethane adduct). The resulting reaction mixture is stirred at a temperature in the range from 25° C. to 90° C. (particularly from 60° C. to 70° C.) for about 2 to 24 hours to yield the desired compounds of formula (I).

In process (xi), the reaction with the vinyl compound of formula (XXXVIII) can be performed by procedures analogous to those outlined in the paragraph for process (x). With a suitable protecting group, such as tert-butyldimethylsilyl, deprotection can be carried out using standard conditions (eg tetra-butylammonium fluoride, hydrofluoric acid) in a solvent such as tetrahydrofuran or water. The subsequent oxidation and reductive amination reactions may be carried out in processes analogous to those outlined in the paragraph for process (v).

In process (xii), the reaction with the vinyl compound of formula (XXXIX) may be carried out in the presence of catalytic dichlorobis(triphenylphosphine)palladium, in a solvent such as N,N-dimethylformamide at an elevated temperature such as 70° C. The subsequent addition reaction may be performed under acidic or basic conditions for example in acetic acid in a solvent such as methanol or isopropanol at an elevated temperature such as 100° C.

In process (xiii), the reaction with the vinyl compound of formula (XXXIX) can be performed by procedures analogous to those outlined in the paragraph for process (xii). The subsequent oxidation can be performed under standard conditions such as by reaction with ozone followed by treatment with dimethylsulfide or triphenylphosphine in a suitable solvent such as dichloromethane or by treatment with osmium tetroxide and sodium periodate in a suitable solvent such as 1,4-dioxane and water. The resulting aldehyde can be derivatised by a reductive amination reaction which may be carried out in a process analogous to that outlined in the paragraph for process (v).

Compounds of formula (X) in which $R^{10}$ represents —C(O)H may be prepared according to the following reaction schemes.

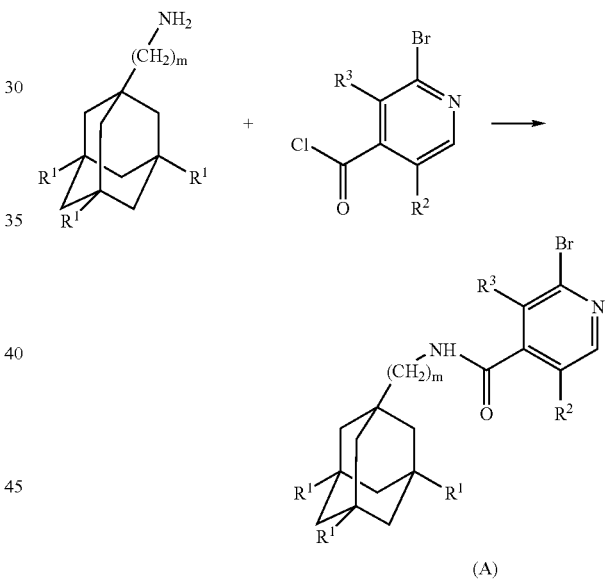

(A)

(A) is then further reacted as follows.

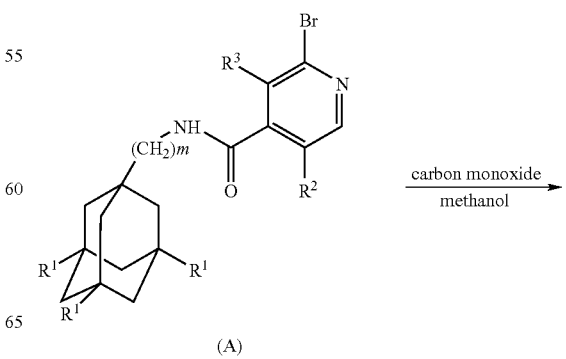

(A)

-continued

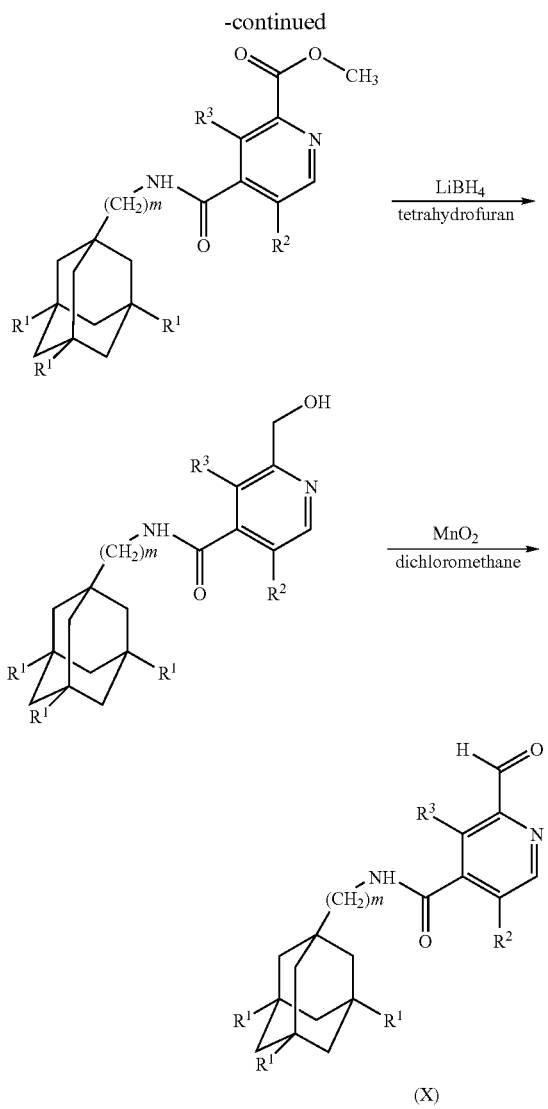

Compounds of formulae (XI) and (XII) in which $R^{11}$ and $R^{12}$ represent —C(O)H may be prepared in a similar manner to the compounds of formula (X).

Compounds of formula (X) in which $R^{10}$ represents —CH$^2$L$^1$ and L$^1$ represents, for example, a chlorine atom may be prepared as shown below:

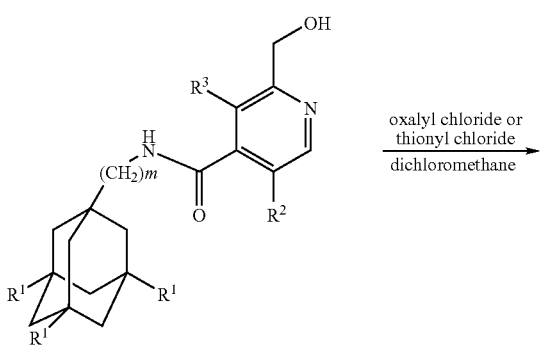

-continued

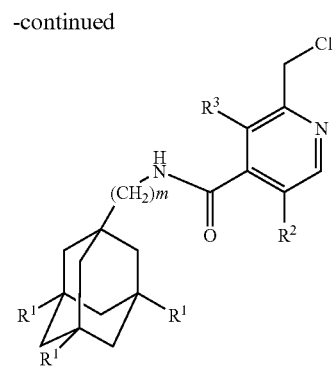

It will be appreciated that compounds of formulae (XI) and (XII) in which $R^{11}$ represents —CH$_2$L$^2$ and $R^{12}$ represents —CH$_2$L$^3$ may be prepared in an analogous manner.

Compounds of formulae (XV), (XVI) and (XVII) may be prepared as described for compound (A) above. Similarly, compounds of formula (XX), (XXI) and (XXII) in which A is NHC(O) may be prepared as described for compound (A) above. Compounds of formula (XX) in which A is C(O)NH may be prepared in the following manner:

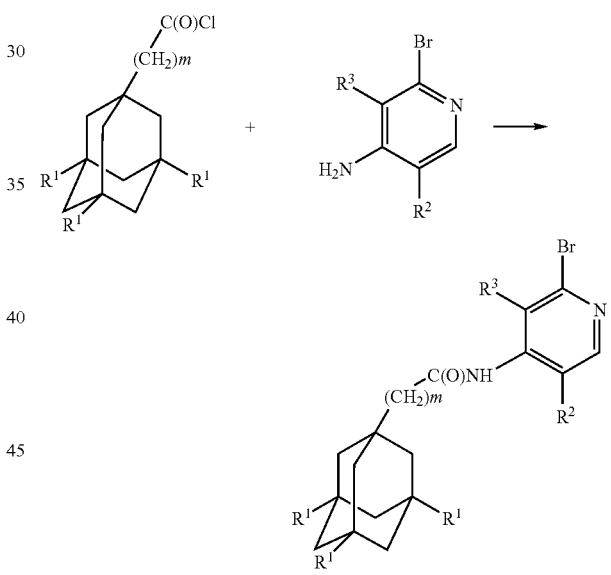

Compounds of formula (XXI) and (XXII) in which A is C(O)NH may be prepared by analogous processes.

Compounds of formula (XXIV) can be prepared by reacting a compound of formula

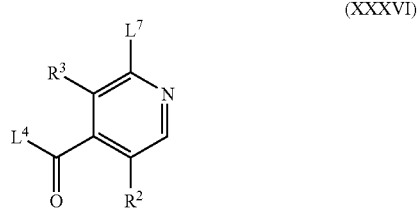

(XXXVI)

wherein L⁷ represents a suitable leaving group such as a halogen atom and R², R³ and L⁴ are as defined in formula (XXIV), with a thiol of formula

(XXXVII)

in which R⁵, R⁶ and R⁷ are as defined in formula (I), in a solvent such as dimethyl formamide, N-methyl-2-pyrrolidinone or ethanol, in the presence of a base such as caesium carbonate, potassium carbonate or sodium hydride and at elevated temperature (e.g. 120° C.).

Compounds of formulae (XXV), (XXVI), (XXVIII), (XXIX) and (XXX) may be prepared in a like manner to the compounds of formula (XXIV).

Compounds of formula (XXXII) (and by analogy compounds of formula (XXXIII) and (XXXIV)) can be prepared by the following route:

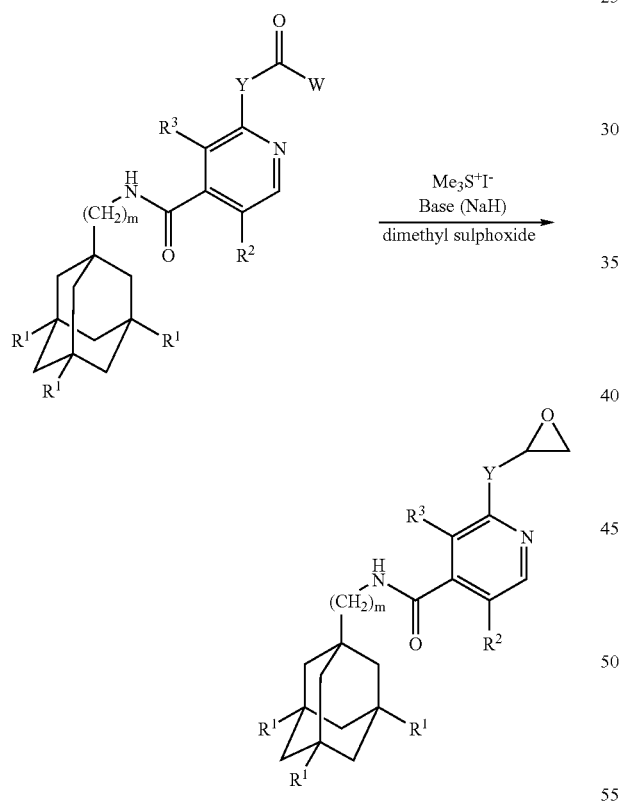

Compounds of formulae (XIII), (XIV), (XVIII), (XIX), (XXIII), (XXVII), (XXXI), (XXXV), (XXXVI), (XXVII), (XXXVIII) and (XXXIX) are either commercially available, are well known in the literature or may be prepared easily using known techniques.

Compounds of formula (I) can be converted into further compounds of formula (I) using standard procedures. For example, compounds of formula (I) in which one of R² and R³ represents a halogen atom may be converted to a corresponding compound of formula (I) in which one of R² and R³ represents a C₁–C₆ alkyl group by reaction with an alkyl Grignard reagent (e.g. methyl magnesium bromide) in the presence of a catalyst such as [1,3-bis(diphenylphosphino) propane]dichloronickel (II) in a solvent such as tetrahydrofuran.

It will be appreciated by those skilled in the art that in the processes of the present invention certain functional groups such as hydroxyl or amino groups in the starting reagents or intermediate compounds may need to be protected by protecting groups. Thus, the preparation of the compounds of formula (I) may involve, at various stages, the addition and removal of one or more protecting groups.

The protection and deprotection of functional groups is described in 'Protective Groups in Organic Chemistry', edited by J. W. F. McOmie, Plenum Press (1973) and 'Protective Groups in Organic Synthesis', 2nd edition, T. W. Greene and P. G. M. Wuts, Wiley-Interscience (1991).

The compounds of formula (I) above may be converted to a pharmaceutically acceptable salt or solvate thereof, preferably an acid addition salt such as a hydrochloride, hydrobromide, phosphate, acetate, fumarate, maleate, tartrate, citrate, oxalate, methanesulphonate p-toluenesulphonate, or an alkali metal salt such as a sodium or potassium salt.

Certain compounds of formula (I) are capable of existing in stereoisomeric forms. It will be understood that the invention encompasses all geometric and optical isomers of the compounds of formula (I) and mixtures thereof including racemates. Tautomers and mixtures thereof also form an aspect of the present invention.

The present invention also provides novel intermediates, in particular, intermediates of formula

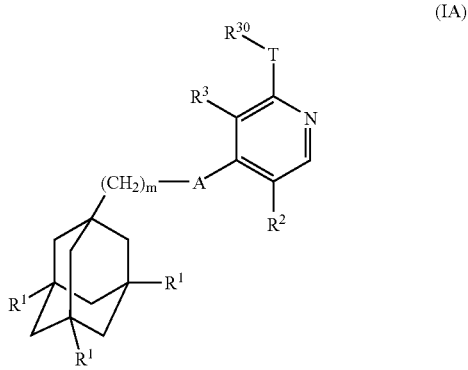
(IA)

wherein T represents —C≡C— or —CH₂CH₂—;
R³⁰ represents —CHO, —CH₂OP¹ or a group of formula

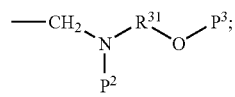

P¹ represents a hydrogen atom or a suitable protecting group (e.g. t-butyldimethylsilyl);
P² represents a suitable protecting group (e.g. t-butylcarbamate);
P³ represents a suitable protecting group (e.g. t-butyldimethylsilyl or tetrahydro-2H-pyran-2-yl);
R³¹ represents a C₅–C₅ alkyl group; and
m, A, R¹, R² and R³ are as defined in formula (I).

In an embodiment of the invention, in formula (IA), m represents 1;

A represents NHC(O);
each $R^1$ represents a hydrogen atom;
$R^2$ represents a halogen atom; and
$R^3$ represents a hydrogen atom.

The compounds of the present invention are advantageous in that they possess pharmacological activity. They are therefore indicated as pharmaceuticals for use in the treatment of rheumatoid arthritis, osteoarthritis, psoriasis, allergic dermatitis, asthma, chronic obstructive pulmonary disease (COPD), hyperresponsiveness of the airway, septic shock, glomerulonephritis, inflammatory bowel disease, Crohn's disease, ulcerative colitis, atherosclerosis, growth and metastases of malignant cells, myoblastic leukaemia, diabetes, Alzheimer's disease, meningitis, osteoporosis, burn injury, ischaemic heart disease, stroke, varicose veins, sarcoidosis, rhinitis, acute and chronic pain, multiple sclerosis, myeloma, bone loss associated with malignancy and inflammatory and neurodegenerative diseases of the eye such as scleritis, episcleritis, uveitis, Sjogrens syndrome-keratoconjuctivitis, sclerokeratitis, optic neuritis, diabetic retinopathy, retinitis pigmentosa, antimalarial-induced retinopathy.

Accordingly, the present invention provides a compound of formula (I) or a pharmaceutically acceptable salt or solvate thereof as hereinbefore defined for use in therapy.

In another aspect, the invention provides the use of a compound of formula (I) or a pharmaceutically acceptable salt or solvate thereof as hereinbefore defined in the manufacture of a medicament for use in therapy.

In the context of the present specification, the term "therapy" also includes "prophylaxis" unless there are specific indications to the contrary. The terms "therapeutic" and "therapeutically" should be construed accordingly.

The invention further provides a method of effecting immunosuppression (e.g. in the treatment of rheumatoid arthritis, osteoarthritis, inflammatory bowel disease, atherosclerosis or psoriasis) which comprises administering a therapeutically effective amount of a compound of formula (I) or a pharmaceutically acceptable salt or solvate thereof as hereinbefore defined to a patient.

The invention also provides a method of treating an obstructive airways disease (e.g. asthma or COPD) which comprises administering to a patient a therapeutically effective amount of a compound of formula (I) or a pharmaceutically acceptable salt or solvate thereof as hereinbefore defined to a patient.

For the above-mentioned therapeutic uses the dosage administered will, of course, vary with the compound employed, the mode of administration, the treatment desired and the disorder indicated. The daily dosage of the compound of formula (I)/salt/solvate (active ingredient) may be in the range from 0.001 mg/kg to 30 mg/kg.

The compounds of formula (I) and pharmaceutically acceptable salts and solvates thereof may be used on their own but will generally be administered in the form of a pharmaceutical composition in which the formula (I) compound/salt/solvate (active ingredient) is in association with a pharmaceutically acceptable adjuvant, diluent or carrier. Depending on the mode of administration, the pharmaceutical composition will preferably comprise from 0.05 to 99% w (percent by weight), more preferably from 0.10 to 70% w, of active ingredient, and, from 1 to 99.95% w, more preferably from 30 to 99.90% w, of a pharmaceutically acceptable adjuvant, diluent or carrier, all percentages by weight being based on total composition.

Thus, the present invention also provides a pharmaceutical composition comprising a compound of formula (I) or a pharmaceutically acceptable salt or solvate thereof as hereinbefore defined in association with a pharmaceutically acceptable adjuvant, diluent or carrier.

The invention further provides a process for the preparation of a pharmaceutical composition of the invention which comprises mixing a compound of formula (I) or a pharmaceutically acceptable salt or solvate thereof as hereinbefore defined with a pharmaceutically acceptable adjuvant, diluent or carrier.

The pharmaceutical composition of the invention may be administered topically (e.g. to the lung and/or airways or to the skin) in the form of solutions, suspensions, heptafluoroalkane aerosols and dry powder formulations; or systemically, e.g. by oral administration in the form of tablets, capsules, syrups, powders or granules, or by parenteral administration in the form of solutions or suspensions, or by subcutaneous administration or by rectal administration in the form of suppositories or transdermally.

The present invention will now be further explained by reference to the following illustrative examples. In the examples the NMR spectra were measured on a Varian Unity spectrometer at a proton frequency of either 300 or 400 MHz. The MS spectra were measured on either a Agilent 1100 MSD G1946D spectrometer or a Hewlett Packard HP1100 MSD G1946A spectrometer. Preparative HPLC separations were performed using a Waters Symmetry® or Xterra® column using 0.1% aqueous trifluoroacetic acid: acetonitrile or 0.1% aqueous airinmoma:acetonitrile as the eluant.

EXAMPLE 1

N-(1-Adamantylmethyl)-5-chloro-2-{3-[(3-hydroxypropyl)-amino]propyl}isonicotinamide

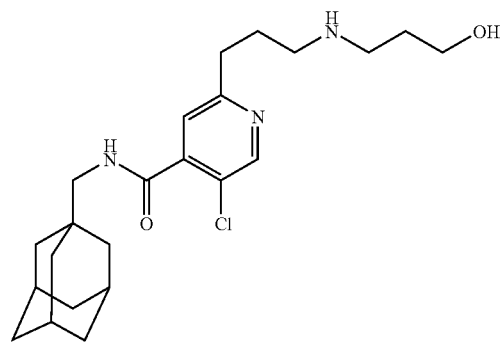

(i) 2-Bromo-5-chloro isonicotinic acid

To a stirred solution of di-isopropylamine (16 ml) in anhydrous tetrahydrofuran (300 ml) at −5° C. was added, dropwise a solution of n-butyl lithium in hexane (2.5 molar, 44 ml) and the resulting solution was stirred for 30 minutes and was then cooled to −70° C. To the cooled solution was added a solution of 2-bromo-5-chloropyridine (19.2 g) in anhydrous tetrahydrofaran (50 ml) maintaining the internal temperature of the reaction below −65° C. The reaction was maintained at −70° C. for 15 minutes and then a steady stream of dried carbon dioxide was passed through the reaction mixture for 30 minutes. The reaction was allowed to warm to room temperature and was poured into a mixture of water (300 ml) and aqueous sodium hydroxide solution (2M, 30 ml). The mixture was extracted with ether and (2×100 ml) and the combined ethereal extracts were back extracted with aqueous sodium hydroxide solution (1M, 2×100 ml). The combined aqueous extracts were acidified to pH 1 with concentrated hydrochloric acid and the resulting solid filtered and dried under vacuum at 50° C. to afford the sub-titled compound as a white solid (14.1 g).

$^1$H NMR (300 MHz, DMSO-$d_6$) δ 8.63 (1H, s); 7.98 (1H, s) MP: 246–247° C. (dec.)

(ii) N-(1-Adamantylmethyl)-2-bromo-5-chloroisonicotinamide

To a stirred suspension of 2-bromo-5-chloro isonicotinic acid (5.0 g) in anhydrous dichloromethane (30 ml) was added dimethylformamide (1 drop) followed by oxalyl chloride (3.7 ml). The reaction was stirred at room temperature for 2 hours and was then evaporated to dryness, azeotroping with toluene. The residue was suspended in ethyl acetate (100 ml) and was cooled to 5° C. where a solution of 1-adamantylmethylamine (3.47 g) and triethylamine (7.0 ml) in ethyl acetate (10 ml) was added dropwise. The mixture was stirred for 2 hours and was then poured into water and the resulting solid filtered and dried under vacuum at 40° C. to afford the titled compound as a white solid (8.05 g).

$^1$H NMR (400 MHz, CDCl$_3$) δ 8.42 (1H, s); 7.77 (1H, s); 6.24 (1H, t); 3.16 (2H, dd); 2.05–2.02 (3H, m); 1.76–1.73 (3H, m); 1.66–1.63 (3H, m); 1.57–1.55 (6H, m). MP: 153–155° C. (dec.) MS: APCI(+ve) 383/385 (M+1)

(iii) N-(1-Adamantylmethyl)-5-chloro-2-(3-hydroxy-1-propynyl)isonicotinamide A mixture of N-(1-adamantylmethyl)-2-bromo-5-chloroisonicotinamide (Example 1(ii)) (0.96 g), propargyl alcohol (0.16 g), copper (I) iodide, bis-triphenylphosphine palladium is dichloride (0.035 g) and diethylamine (10 ml) was stirred together at room temperature for 20 hours. The mixture was concentrated and the residue partitioned between ethyl acetate and 1M aqueous hydrochloric acid solution (2×25 ml) and the mixture was extracted into ethyl acetate (3×25 ml). The combined extracts were dried over anhydrous magnesium sulfate, filtered and concentrated. The residue was purified by chromatography on silica gel eluting with ethyl acetate:iso-hexane (1:4 to 1:1) and then ethyl acetate to afford the sub-titled compound (0.48 g) as an oil.

$^1$H NMR (400 MHz, CDCl$_3$) δ 8.59 (1H, s); 7.69 (1H, s); 6.30 (1H, t); 4.52 (2H, d); 3.18 (2H, d); 2.05–2.02 (3H, m); 1.87 (1H, t); 1.76–1.73 (3H, m); 1.66–1.63 (3H, m); 1.57–1.55 (6H, m). MS: APCI(+ve) 359/361 (M+1)

(iv) N-(1-Adamantylmethyl)-5-chloro-2-(3-hydroxypropyl)isonicotinamide

A stirred suspension of N-(1-adamantylmethyl)-5-chloro-2-(3-hydroxy-1-propynyl)isonicotinamide (Example 1 (iii)) (0.48 g) and 5% rhodium on carbon (0.020 g) was stirred under a positive pressure (3 barr) of hydrogen until no further uptake was observed. The mixture was filtered and concentrated. The residue was purified by chromatography on silica gel eluting with ethyl acetate to afford the sub-titled compound (0.305 g) as an oil.

$^1$H NMR (300 MHz, CDCl$_3$) δ 8.54 (1H, s); 7.50 (1H, s); 6.34 (1H, t); 3.69 (2H, dd); 3.18 (2H, d); 2.96 (2H, t); 2.62 (1H, t); 2.05–2.02 (5H, m); 1.76–1.73 (3H, m); 1.66–1.63 (3H, m); 1.57–1.55 (6H, m). MS: APCI(+ve) 363/365 (M+1)

(v) N-(1-Adamantylmethyl)-5-chloro-2-{3-[(3-hydroxypropyl)-amino]propyl}isonicotinamide To a stirred solution of N-(1-adamantylmethyl)-5-chloro-2-(3-hydroxypropyl)isonicotinamide (Example 1(iv)) (0.30 g) in dry dichloromethane (20 ml) was added Dess-Martin periodinane (0.42 g) and the resulting suspension stirred at room temperature for 30 minutes. The reaction was poured into a mixture of saturated sodium bicarbonate solution containing sodium thiosulfate (10% w/v, 20 ml) and the mixture was extracted into ethyl acetate (3×25 ml). The combined extracts were dried over anhydrous magnesium sulfate, filtered and concentrated. The crude aldehyde was dissolved in methanol (2 ml) and 3-aminopropan-1-ol (0.15 g) added along with acetic acid (0.1 ml). The mixture was stirred for 2 hours at ambient temperature and then sodium triacetoxy borohydride (0.424 g) was added and the reaction stirred for 20 hours, concentrated and the residue was partitioned between 2M aqueous hydrochloric acid solution (10 ml) and ethyl acetate (10 ml). The layers were separated and the organic phase re-extracted with 2N hydrochloric acid (2×10 ml). The combined aqueous extracts were basified with 5M aqueous ammonium hydroxide solution, extracted into ethyl acetate (2×25 ml) and the combined extracts were dried over anhydrous magnesium sulfate, filtered and concentrated. The residue was purified by chromatography on silica gel eluting with 0.7N anhydrous ammonia in methanol:dichloromethane (1:4) to afford the titled compound (0.116 g) as a white solid.

$^1$H NMR (400 MHz, CDCl$_3$) δ 8.54 (1H, s); 7.34 (1H, s); 6.97 (1H, t); 3.74 (2H, t); 3.15 (2H, d); 2.87–2.81 (4H, m); 2.66 (2H, t); 2.05–1.96 (5H, m); 1.76–1.73 (3H, m; 1.66–1.63 (5H, m); 1.57–1.55 (6H, m). MS: APCI(+ve) 420/422 (M+1) MP: 84–85° C.

EXAMPLE 2

N-(1-Adamantylmethyl)-5-chloro-2-{3-[(3-hydroxypropyl)amino]propyl}-isonicotinamide dihydrochloride

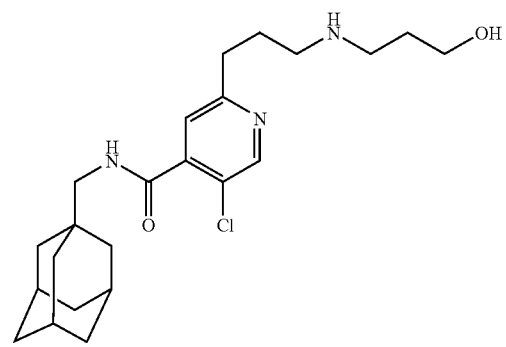

Preparative Route 1

(i) N(1-Adamantylmethyl)-2-bromo-5-chloroisonicotinamide

To a stirred solution of di-isopropylamine (2.1 ml) in anhydrous tetrahydrofuran (15 ml) at is −5° C. was added, dropwise a solution of n-butyl lithium in hexane (2.5 molar, 4.8 ml) and the resulting solution was stirred for 30 minutes and was then cooled to −70° C. To the cooled solution was added a solution of 2-bromo-5-chloropyridine (2.39 g) in anhydrous tetrahydrofuran (10 ml) maintaining the internal temperature of the reaction below −65° C. The reaction was maintained at −70° C. for 15 minutes and then a solution of 1-adamantylmethyl isocyanate (1.91 g) in anhydrous tetrahydrofuran (5 ml) was dropwise added (care exotherm). The mixture was stirred for 10 minutes and was then poured into a solution of 1M aqueous hydrochloric acid solution (50 ml) and the mixture extracted into ethyl acetate (3×25 ml). The combined extracts were dried over anhydrous magnesium sulfate, filtered and concentrated. The residue was purified by chromatography on silica gel eluting with ethyl acetate:iso-hexane (1:9 to 1:4 to 1:1) to afford the sub-titled compound (2.70 g) as a white solid.

$^1$H NMR (400 MHz, CDCl$_3$) δ 8.41 (1H, s); 7.98 (1H, s); 6.21 (1H, t); 3.16 (2H, d); 2.05–2.02 (3H, m); 1.76–1.73 (3H, m); 1.66–1.63 (3H, m); 1.57–1.55 (6H, m). MP: 193–194° C.

(ii) tert-Butyl prop-2-ynyl[3-(tetrahydro-2H-pyran-2-yloxy)propyl]carbamate

A solution of tert-butyl prop-2-ynylcarbamate (1.2 g) in anhydrous N,N-dimethylformamide (5 ml) was treated with 60% sodium hydride (0.245 g) in one portion. After evolution of hydrogen had ceased 2-(3-bromopropoxy)tetrahydro-2H-pyran (1.36 g) was added. The reaction mixture was stirred under nitrogen for 48 hours then diluted with water (50 ml) and extracted into ethyl acetate (3×25 ml). The combined extracts were dried over anhydrous sodium sulphate, filtered and concentrated to afford the sub-titled compound (1.61 g) as a colourless oil.

$^1$H NMR (400 MHz, CDCl$_3$) δ 4.60 (2H, m); 4.05 (2H, broad); 3.90–3.70 (4H, m); 3.60–3.41 (7H, m); 2.22–2.09 (3H, m); 1.91–1.82 (4H, m); 1.47 (9H, s).

(iii) tert-Butyl 3-(4-{[(1-adamantylmethyl)amino]carbonyl}-5-chloropyridin-2-yl)prop-2-ynyl[3-(tetrahydro-2H-pyran-2-yloxy)propyl]carbamate A suspension of N-(1-adamantylmethyl)-2-bromo-5-chloroisonicotinamide (Example 2(i)) (0.43 g) and tert-butyl prop-2-ynyl[3-(tetrahydro-2H-pyran-2-yloxy)propyl]carbamate (Example 2(ii)) (0.60 g) in anhydrous acetonitrile (6 ml) and triethylamine (6 ml) was purged with nitrogen for 5 minutes and then copper (I) iodide (0.004 g) and bis-triphenyphosphine palladium dichloride (0.014 g) were added. The mixture was stirred under nitrogen for 2 hours. The mixture was concentrated and the residue was purified by chromatography on silica gel eluting with iso-hexane:ethyl acetate (19:1 to 7:3) to afford the sub-titled compound (0.39 g) as a yellow gum.

$^1$H NMR (400 MHz, CDCl$_3$) δ 8.58 (1H, s); 7.67 (1H, s); 6.25 (1H, broad); 4.57 (1H, t); 4.33 (2H, broad); 3.9–3.77 (2H, m); 3.5–3.41 (4H, m); 3.18 (2H, d); 2.02 (3H, broad); 1.92–1.85 (2H, t); 1.80–1.60 (7H, m); 1.58 (12H, s); 1.48 (9H, s). MS: APCI(+ve) 516/518

(iv) tert-Butyl 3-(4-{[(1-adamantylmethyl)amino]carbonyl}-5-chloropyridin-2-yl)propyl[3-(tetrahydro-2H-pyran-2-yloxy)propyl]carbamate A stirred suspension of tert-butyl 3-(4-{[(1-adamantylmethyl)amino]carbonyl}-5-chloropyridin-2-yl)prop-2-ynyl[3-(tetrahydro-2H-pyran-2-yloxy)propyl]carbamate (Example 2(iii)) (0.35 g) and 5% rhodium on carbon (0.020 g) was stirred under a positive pressure (2 barr) of hydrogen until no further uptake was observed. The mixture was filtered and concentrated. The residue was purified by chromatography on silica gel eluting with dichloromethane:acetone (19:1 to 9:1) to afford the sub-titled compound (0.24 g) as a colourless gum.

$^1$H NMR (300 MHz, CDCl$_3$) δ 8.54 (1H, s); 7.44 (1H, s); 6.42 (1H, broad); 4.54 (1H, t); 3.83 (1H, t of d); 3.73 (1H, m); 3.50 (1H, m); 3.38 (1H, m); 3.25 (4H, t); 3.19 (2H, d); 2.78 (2H, t); 2.01–1.9 (5H, m); 1.80 (2H, t); 1.78–1.62 (4H, d of d), 1.60 (10H, d); 1.44 (9H, s). MS: APCI(+ve) 604/606 (M+1)

(v) N-(1-Adamantylmethyl)-5-chloro-2-{3-[(3-hydroxypropyl)amino]propyl}-isonicotinamide dihydrochloride tert-Butyl 3-(4-{[(1-adamantylmethyl)amino]carbonyl}-5-chloropyridin-2-yl)propyl[3-(tetrahydro-2H-pyran-2-yloxy)propyl]carbamate (Example 2(iv)) (0.24 g) was dissolved in a mixture of methanol (10 ml) and 2M aqueous hydrochloric acid solution (10 ml); the solution was left to stand for 0.5 hours. The mixture was concentrated and the residue diluted with 2M aqueous sodium hydroxide solution (25 ml). The mixture was extracted into dichloromethane (3×25 ml) and the combined extracts were concentrated. The residue was dissolved in a solution of hydrogen chloride in 1,4-dioxane (10 ml of a 4M solution) and left to stand for 0.5 hours. The solution was concentrated and the residue suspended in 2M aqueous sodium hydroxide solution (25 ml), extracted into dichloromethane (3×25 ml) and the combined extracts were concentrated. The residue was purified by chromatography on silica gel eluting with dichloromethane:methanol:0.88 aqueous ammonia (89:10:1). The isolated material was dissolved in a solution of hydrogen chloride in 1,4-dioxane (10 ml of a 4M solution) and concentrated; the resultant solid was recrystallised from ethyl acetate/methanol to afford the titled compound (0.115 g) as a colourless solid.

$^1$H NMR (400 MHz, DMSO-d$_6$) δ 8.78 (2H, broad); 8.60 (1H, s); 8.54 (1H, t); 7.36 (1H, s); 3.46 (2H, t); 2.95–2.83 (8H, m); 2.08–1.99 (2H, q); 1.95 (3H, s); 1.81–1.74 (2H, t); 1.69–1.58 (6H, q); 1.52 (6H, s). MS: APCI(+ve) 420/422 (M+1) MP: decomposed at 210° C.

Preparative Route 2

(vi) tert-Butyl[3-(4-{[(1-adamantylmethyl)amino]carbonyl}-5-chloropyridin-2-yl)propyl](3-{[tert-butyl(dimethyl)silyl]oxy}propyl)carbamate A solution of tert-butyl allyl(3-{[tert-butyl(dimethyl)silyl]oxy}propyl)carbamate (0.50 g) in 9-boroabicyclo[3.3.1]nonane (6.0 ml of a 0.5M solution in tetrahydrofuran) was heated at reflux under nitrogen for 4 hours. The solution was cooled to 0° C. and potassium phosphate (2 ml of a 3M solution in water) was added. The mixture was stirred for 15 minutes and a solution of N-(1-adamantylmethyl)-2,5-dichloroisonicotinamide (0.50 g) (prepared as described in WO 01/94338) and tetrakis(triphenylphosphine)palladium (0) (0.045 g) in anhydrous N,N-dimethylformamide (3 ml) was added. The mixture was heated at 70° C. under nitrogen for 4 hours, diluted with saturated brine (25 ml) and extracted into ethyl acetate (3×25 ml). The combined extracts were dried over anhydrous sodium sulphate, filtered and concentrated. The residue was purified by chromatography on silica, gel eluting with iso-hexane:ethyl acetate (9:1 to 4:1) to afford the sub-titled compound (0.46 g).
MS: APCI(+ve) 636/634 (M+1)

(vii) N-(1-Adamantylmethyl)-5-chloro-2-{3-[(3-hydroxypropyl)amino]propyl}isonicotinamide dihydrochloride tert-Butyl[3-(4-{[(1-adamantylmethyl)amino]carbonyl}-5-chloropyridin-2-yl)propyl](3-{[tert-butyl(dimethyl)silyl]oxy}propyl)carbamate (Example 2(vi)) (0.46 g) was dissolved in a solution of hydrogen chloride in 1,4-dioxane (10 ml of a 4M solution) and concentrated; the resultant solid was recrystallised from 1,4-dioxane/methanol and the solid collected by filtration to afford the titled compound (0.24 g) as a colourless powder.
$^1$H NMR (400 MHz, DMSO-$d_6$) δ 8.78 (2H, broad); 8.60 (1H, s); 8.54 (1H, t); 7.36 (1H, s); 3.46 (2H, t); 2.95–2.83 (8H, m); 2.08–1.99 (2H, q); 1.95 (3H, s); 1.81–1.74 (2H, t); 1.69–1.58 (6H, q); 1.52 (6H, s). MS: APCI(+ve) 420/422 (M+1) MP: decomposed at 210° C.

EXAMPLE 3

N-(1-Adamantylmethyl)-2-chloro-5-{3-[(3-hydroxypropyl)amino]propyl}nicotinamide

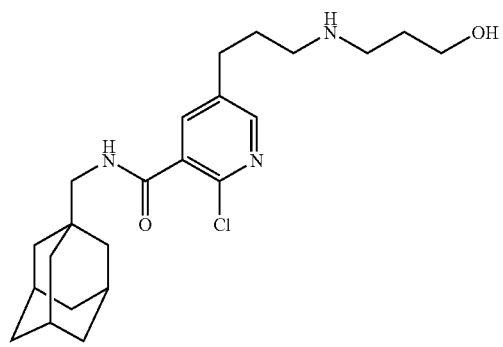

(i)
N-(1-Adamantylmethyl)-5-iodo-2-chloronicotinamide

2-Hydroxy-5-iodo-nicotinic acid (2.65 g) was added to thionyl chloride (10 ml) followed by anhydrous N,N-dimethylformamide (1 drop) and the resulting suspension heated to 100° C. for 3 hours. The mixture was cooled and concentrated, azeotroping with toluene. The residue was dissolved in dry dichloromethane (70 ml), cooled to 0° C. and a mixture of 1-adamantylmethylamine (1.65 g) and triethylamine (2.81 ml) in dry dichloromethane (30 ml) added dropwise. The reaction mixture was stirred for 1 hour, was washed with 0.5M aqueous hydrochloric acid, dried over anhydrous magnesium sulfate, filtered and concentrated. The residue was purified by chromatography on silica gel eluting with ethyl acetate:dichloromethane (1:9) to afford the sub-titled compound as a solid.
$^1$H NMR (300 MHz, CDCl$_3$) δ 8.65 (1H, d); 8.42 (1H, d); 6.50 (1H, t); 3.19 (2H, dd); 2.05–2.02 (3H, m); 1.76–1.73 (3H, m); 1.66–1.63 (3H, m); 1.57–1.55 (6H, m). MS: APCI(+ve) 430/432 (M+1) MP: 163–164° C.

(ii) N-(1-Adamantylmethyl)-2-chloro-5-(3-oxopropyl)nicotinamide

A mixture of N-(1-adamantylmethyl)-5-iodo-2-chloronicotinamide (Example 3(i)) (2.15 g), allyl alcohol (0.58 g), palladium (II) acetate (0.015 g), sodium bicarbonate (1.05 g) and tetra-butyl ammonium chloride (1.39 g) were stirred together in anhydrous N,N-dimethylformamide (20 ml) for 20 hours. The reaction mixture was poured into water (100 ml) and extracted into ethyl acetate (3×25 ml). The combined extracts were dried over anhydrous magnesium sulfate, filtered and concentrated. The residue was purified by chromatography on silica gel eluting with ethyl acetate:isohexane (1:1) to afford the sub-titled compound (0.65 g).
$^1$H NMR (300 MHz, CDCl$_3$) δ 9.82 (1H, s); 8.33 (1H, d); 8.01 (1H, d); 6.50 (1H, t); 3.19 (2H, d); 2.98 (2H, dd); 2.86 (2H, dd); 2.05–2.02 (3H, m); 1.76–1.73 (3H, m); 1.66–1.63 (3H, m); 1.57–1.55 (6H, m). MS: APCI(+ve) 361, 363 (M+1)

(iii) N-(1-Adamantylmethyl)-2-chloro-5-{3-[(3-hydroxypropyl)amino]propyl}-nicotinamide To a stirred solution of N-(1-adamantylmethyl)-2-chloro-5-(3-oxopropyl)nicotinamide (Example 3(ii)) (0.10 g) in methanol (3 ml) and acetic acid (0.1 ml) was added. 3-aminopropanol (0.042 g) and the resulting solution was stirred for 2 hours and then sodium cyanoborohydride (0.020 g) was added and the reaction mixture stirred for 20 hours. The mixture was concentrated and the residue partitioned between 2M aqueous hydrochloric acid solution and ethyl acetate (2×10 ml). The layers were separated and the organic phase re-extracted with $^2$M aqueous hydrochloric acid solution (2×10 ml). The combined aqueous extracts were basified with 5M aqueous ammonium hydroxide solution, extracted into ethyl acetate (2×25 ml) and the combined extracts were dried over anhydrous magnesium sulfate, filtered and concentrated to afford the titled compound (0.075 g) as a white solid.
$^1$H NMR (400 MHz, CDCl$_3$) δ 8.28 (1H, s); 7.93 (1H, s); 6.79 (1H, t); 3.79 (2H, t); 3.17 (2H, d); 2.86 (2H, t); 2.71 (2H, t); 2.65 (2H, t); 2.66 (2H, t); 2.05–1.96 (5H, m); 1.87–1.80 (2H, m); 1.76–1.73 (3H, m) 1.66–1.63 (3H, m); 1.57–1.55 (6H, m). MS: APCI(+ve) 420/422 (M+1) MP: 105–107° C.

EXAMPLE 4

N-(1-Adamantylmethyl)-2-chloro-5-(3-{[(1S)-2-hydroxy-1-methylethyl]amino}propyl)nicotinamide

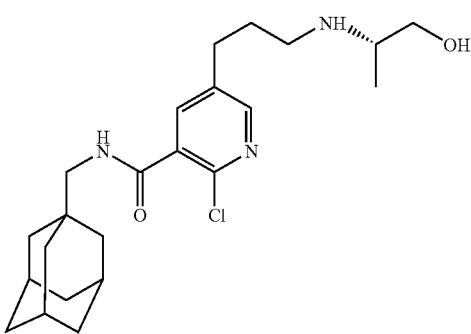

The titled compound was prepared from N-(1-adamantylmethyl)-2-chloro-5-(3-oxopropyl)nicotinamide (Example 3(ii)) (0.10 g), (S)-2-aminopropanol (0.046 g) and sodium cyanoborohydride 0.020 g) in methanol (3 ml) and acetic acid (0.1 ml) by the method of Example 3(iii). The crude product was purified by chromatography on silica gel eluting with 0.7N anhydrous ammonia in methanol:ethyl acetate (1:5) to afford the titled compound as an oil (0.082 g).

$^1$H NMR (300 MHz, CDCl$_3$) δ 8.28 (1H, s); 7.99 (1H, s); 6.64 (1H, t); 3.56 (2H, dd); 3.23 (2H, dd); 3.19 (2H, d); 2.80–2.70 (3H, m); 2.58–2.50 (1H, m); 2.05–1.96 (3H, m); 1.87–1.80 (2H, m); 1.76–1.73 (3H, m); 1.66–1.63 (3H, m); 1.57–1.55 (6H, m); 1.04 (3H, d). MS: APCI(+ve) 420/422 (M+1)

EXAMPLE 5

N-(1-Adamantylmethyl)-2-chloro-5-(3-{[(1R)-2-hydroxy-1-methylethyl]amino}propyl)nicotinamide

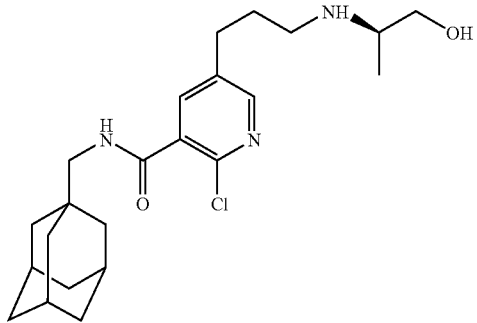

The titled compound was prepared from N-(1-adamantylmethyl)-2-chloro-5-(3-oxopropyl)nicotinamide (Example 3(ii)) (0.10 g), (R)-2-aminopropanol (0.046 g) and sodium cyanoborohydride (0.020 g) in methanol (3 ml) and acetic acid (0.1 ml) by the method of Example 3(iii). The product was purified by chromatography on silica gel eluting with 0.7M anhydrous ammonia in methanol:ethyl acetate (1:5) to afford the titled compound as an oil (0.085 g).

$^1$H NMR (300 MHz, CDCl$_3$) δ 8.28 (1H, s); 7.99 (1H, s); 6.64 (1H, t); 3.56 (2H, dd); 3.23 (2H, dd); 3.19 (2H, d); 2.80–2.70 (3H, m); 2.58–2.50 (1H, m); 2.05–1.96 (3H, m); 1.87–1.80 (2H, m); 1.76–1.73 (3H, m); 1.66–1.63 (3H, m); 1.57–1.55 (6H, m); 1.04 (3H, d). MS: APCI(+ve) 420/422 (M+1)

EXAMPLE 6

N-(1-Adamantylmethyl)-2-(3-aminopropyl)-5-chloroisonicotinamide hydrochloride

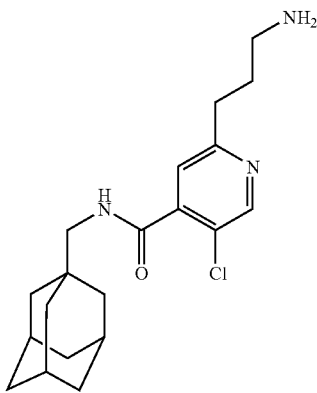

(i) tert-Butyl 3-(4-{[(1-adamantylmethyl)amino]carbonyl}-5-chloropyridin-2-yl)prop-2-ynylcarbamate.

A suspension of N-(1-adamantylmethyl)-5-chloro-2-iodoisonicotinamide (Example2(i)) (0.43 g) and tert-butyl prop-2-ynylcarbamate, (0.31 g) in anhydrous acetonitrile (5 ml) and triethylamine (5 ml) was purged with nitrogen for 5 minutes and the copper (I) iodide (0.004 g) and bis-triphenyphosphine palladium dichloride (0.014 g) were added. The mixture was stirred under nitrogen for 0.75 hours. The mixture was concentrated and the residue was purified by chromatography on silica gel eluting with acetone:dichloromethane (1:19) to afford the sub-titled compound (0.34 g) as a yellow foam.

$^1$H NMR (400 MHz, CDCl$_3$) δ 8.58 (1H, s); 7.67 (1H, s); 6.25 (1H, t); 4.82 (1H, broad); 4.18 (2H, d); 3.18 (2H, d); 2.02 (3H, s); 1.76–1.64 (4H, d of d); 1.60–1.57 (10H, d); 1.46 (9H, s). MS: APCI(+ve) 458/460 (M+1)

(ii) N-(1-Adamantylmethyl)-2-(3-aminopropyl)-5-chloroisonicotinamide hydrochloride A stirred suspension of tert-butyl 3-(4-{[(1-adamantylmethyl)amino]carbonyl}-5-chloropyridin-2-yl)prop-2-ynylcarbamate (Example 6(i)) (0.34 g) and 5% rhodium on carbon was stirred under a positive pressure (2 barr) of hydrogen until no further uptake was observed. The mixture was filtered and concentrated. The residue was dissolved in a solution of hydrogen chloride in 1,4-dioxane (10 ml of a 4M solution) and left to stand for 0.5 hours. The solution was concentrated and the residue triturated with ethyl acetate to afford the titled compound (0.174 g) as a beige powder.

$^1$H NMR (300 MHz, DMSO-d$_6$) δ 8.60 (1H, s); 8.54 (1H, t); 8.02 (3H, broad); 7.34 (1H, s); 2.94 (2H, d); 2.85 (4H, m); 1.97 (5H, m); 1.7–1.58 (6H, q); 1.52 (6H, s). MS: APCI(+ve) 362/364 (M+1) MP: 150° C. (dec.)

EXAMPLE 7

N-(1-Adamantylmethyl)-5-chloro-2-[3-(ethylamino)propyl]isonicotinamide hydrochloride

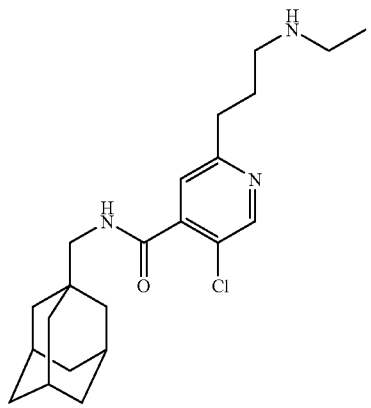

Preparative Route 1

(i) tert-Butyl ethyl(prop-2-ynyl)carbamate

The sub-titled compound was prepared from tert-butyl prop-2-ynylcarbamate (0.6g), 60% sodium hydride (0.186 g), ethyl iodide (1.55 ml) and anhydrous N-methyl-2-pyrrolidinone (4 ml) by the method of Example 2(ii). The crude product was purified by chromatography on silica gel eluting with iso-hexane:ethyl acetate (19:1) to afford (0.34 g) of a colourless oil.

$^1$H NMR (400 MHz, CDCl$_3$) δ 4.04 (2H, broad); 3.36 (2H, q); 2.18 (1H, t); 1.14 (3H, t); 1.47 (9H, s).

(ii) tert-Butyl 3-(4-{[(1-adamantylmethyl)amino]carbonyl}-5-chloropyridin2-yl)prop-2-ynyl(ethyl)carbamate The sub-titled compound was prepared from N-(1 adamantylmethyl)-5-chloro-2-iodoisonicotinamide (Example 2(i)) (0.40 g), tert-butyl ethyl(prop-2-ynyl)carbamate (Example 7(i)) (0.34 g), copper (I) iodide (0.004 g), bis-triphenyphosphine palladium dichloride (0.014 g), triethylamine (5 ml) and anhydrous acetonitrile (5 ml) by the method of Example 2(iii). The crude product was purified by chromatography on silica gel eluting with iso-hexane:ethyl acetate (9:1 to 7:3) to afford the sub-titled compound (0.30 g).

$^1$H NMR (400 MHz CDCl$_3$) δ 8.58. (1H, s); 7.67 (1H, s); 6.22 (1H, broad); 4.31 (2H, broad); 3.42 (2H, q); 3.18 (2H, d); 2.02 (3H, broad); 1.80–1.60 (6H, d of d); 1.57 (6H, s); 1.48 (9H, s); 1.18(3H, t). MS: APCI(+ve) 486/488 (M+1)

(iii) N-(1-Adamantylmethyl)-5-chloro-2-[3-(ethylamino)propyl]isonicotinamide hydrochloride The titled compound was prepared from tert-butyl 3-(4-{[(1-adamantylmethyl)amino]-carbonyl}-5-chloropyridin-2-yl)prop-2-ynyl(ethyl)carbamate (Example 7(ii)) (0.30 g) by the method of Example 6(ii). The crude hydrochloride salt was suspended in 2M aqueous sodium hydroxide solution (25 ml), extracted into ethyl acetate (3×25 ml). and the combined extracts were concentrated. The residue was purified by chromatography on silica gel eluting with dichloromethane:methanol:0.88 aqueous ammonia (89:10:1). The isolated material was dissolved in a solution of hydrogen chloride in 1,4-dioxane (10 ml of a 4M solution) and concentrated; the resultant solid was triturated with ethyl acetate and the solid collected by filtration. Final purification was by preparative reverse phase HPLC to afford the titled compound (0.025 g) as a colourless powder.

$^1$H NMR (300 MHz, DMSO-d$_6$) δ 8.84 (2H, broad); 8.61 (1H, s); 8.54 (1H, t); 7.36 (1H, s); 3.0–2.80 (8H, m); 2.04 (2H, q); 1.95 (3H, s); 1.7–1.58 (6H, q); 1.52 (6H, s); 1.19 (3H, t). MS: APCI(+ve) 390/392 (M+1) MP: 206–208° C. (dec.)

Preparative Route 2

(iv) tert-Butyl allyl(ethyl)carbamate

The sub-titled compound was prepared from tert-butyl allylcarbamate (1.0 g), 60% sodium hydride (0.254 g), ethyl iodide (1.55 ml) and anhydrous N-methyl-2-pyrrolidinone (4 ml) by the method of Example 2(ii). The crude product was purified by chromatography on silica gel eluting with iso-hexane:ethyl acetate (19:1) to afford (0.53 g) of a colourless oil.

$^1$H NMR (400 MHz, CDCl$_3$) δ 5.78 (1H, m); 5.12 (2H, m), 3.80 (2H, s); 3.22 (2H, d); 1.46 (9H, s); 1.08 (3H, t).

(v) N-(1-Adamantylmethyl)-5-chloro-2-[3-(ethylamino)propyl]isonicotinamide hydrochloride A solution of tert-butyl allylcarbamate (Example 7(iv)) (0.23 g) in 9-boroabicyclo[3.3.1]nonane (5 ml of a 0.5M solution in tetrahydrofuran) was heated at reflux under nitrogen for 6 hours. The solution was cooled to room temperature and potassium phosphate (1 ml of a 3M solution in water) was added. The mixture was stirred for 15 minutes and a solution of N-(1-adamantylmethyl)-2-bromo-5-chloroisonicotinamide (Example 1(ii)) (0.383 g) and dichloro[1,1'-bis(diphenylphosphino)ferrocenyl]palladium (II) (0.045 g) in anhydrous N,N-dimethylformamide (8 ml) was added. The mixture was stirred for 6 hours, diluted with saturated brine (25 ml) and extracted into ethyl acetate (3×25 ml). The combined extracts were dried over anhydrous sodium sulphate, filtered and concentrated. The residue was purified by chromatography on silica gel eluting with iso-hexane:ethyl acetate (4:1 to 2:1). The isolated material (0.30 g) was dissolved in a solution of hydrogen chloride in 1,4-dioxane (10 ml of a 4M solution) and concentrated; the resultant solid was triturated with ethyl acetate and the solid collected by filtration to afford the titled compound (0.245 g) as a colourless powder.

EXAMPLE 8

N-(1-Adamantylmethyl)-5-chloro-2-({2-[(3-hydroxypropyl)amino]-ethyl}thio)isonicotinamide hydrochloride

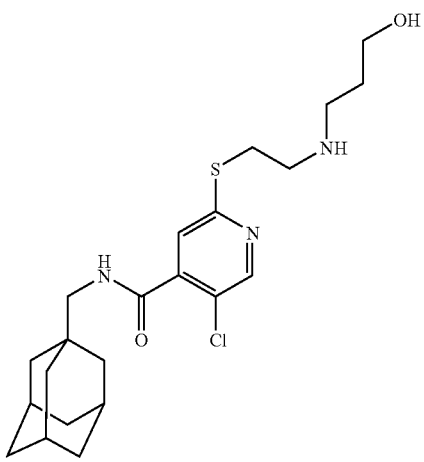

(i) 2-({2-[(tert-Butoxycarbonyl)amino]ethyl}thio)-5-chloroisonicotinic acid

To a solution of 2,5-dichloroisonicotinic acid (1.82 g) in anhydrous N,N-dimethylformamide (10 ml) was added 60% sodium hydride (0.455 g) in small portions. After gas evolution had ceased tert-butyl 2-mercaptoethylcarbamate (1.60 ml) was added. The reaction mixture was then heated at 60° C. under nitrogen for 10 hours. Further amounts of 60% sodium hydride (0.225 g) and tert-butyl 2-mercaptoethylcarbamate (1.60 ml) were then added and heating was continued for 2 hours. The reaction mixture was concentrated and the residue suspended in 2M aqueous hydrochloric acid (25 ml) and extracted into ethyl acetate (3×25 ml). The combined extracts were dried over anhydrous sodium sulphate, filtered and concentrated. The residue was purified by chromatography on silica gel eluting with iso-hexane:ethyl acetate:acetic acid (6:4:0.1) to afford the sub-titled compound (1.0 g) as a colourless powder.

$^1$H NMR (300 MHz, DMSO-$d_6$) δ 8.59 (1H, s); 7.60(1H, s); 7.02 (1H, s); 3.20 (4H, s); 1.37 (9H, s).

(ii) tert-Butyl 2-[(4-{[(1-adamantylmethyl)amino]carbonyl}-5-chloropyridin-2-yl)thio]ethyl[3-(tetrahydro-2H-pyran-2-yloxy)propyl]carbamate To a solution of 2-({2-[(tert-butoxycarbonyl)amino]ethyl}thio)-5-chloroisonicotinic acid (Example 8(i)) (0.332 g) in anhydrous N-methyl-2-pyrrolidinone (5 ml) was added 60% sodium hydride (0.084 g). After 0.5 hours 2-(3-bromopropoxy)tetrahydro-2H-pyran (0.244 g) was added and the mixture was stirred for 16 hours under nitrogen. The reaction mixture was diluted with water (50 ml) and ethyl acetate (50 ml) followed by 2M aqueous hydrochloric acid solution (50 ml). The mixture was extracted into ethyl acetate (3×25 ml) and the combined extracts were dried over anhydrous sodium sulphate, filtered and concentrated. The residue was dissolved in anhydrous N,N-dimethylformamide (5 ml) and 1,1'-carbonyldiimidazole (0.162 g) was added. After 3 hours the mixture was treated with 1-adamantylmethylamine (0.163 g) in one portion and the whole was stirred for 72 hours. The reaction mixture was diluted with water (50 ml) and extracted into ethyl acetate (3×25 ml); the combined extracts were dried over anhydrous sodium sulphate, filtered and concentrated. The residue was purified by chromatography on silica gel eluting with dichloromethane:ethyl acetate (9:1) to afford the sub-titled compound (0.15 g) as a colourless oil.

MS: APCI(+ve) 622/624 (M+1).

(iii) N-(1-Adamantylmethyl)-5-chloro-2-({2-[(3-hydroxypropyl)amino]ethyl}-thio)isonicotinamide hydrochloride The titled compound was prepared from tert-butyl 2-[(4-{[(1-adamantylmethyl)amino]carbonyl}-5-chloropyridin-2-yl)thio]ethyl[3-(tetrahydro-2H-pyran-2-yloxy)propyl]carbamate (Example 8(ii)) (0.15 g) by the method of Example 2(v). The crude hydrochloride salt was triturated with ethyl acetate to afford the titled compound (0.084 g) as a colourless foam.

$^1$H NMR (300 MHz, DMSO-$d_6$) δ 8.81 (1H, broad); 8.57 (1H, s); 8.54 (1H, t); 7.44 (1H, s); 3.50–3.42 (4H, m); 3.19 (2H, t); 3.01 (2H, t); 2.93 (2H, d); 1.94 (3H, s); 1.76 (2H, quintet); 1.69–1.57 (6H, q); 1.51 (6H, s). MS: APCI(+ve) 438/440 (M+1).

EXAMPLE 9

N-(1-Adamantylmethyl)-5-chloro-2-(3-{[(1R)-2-hydroxy-1-methylethyl]amino}propyl)isonicotinamide, dihydrochloride

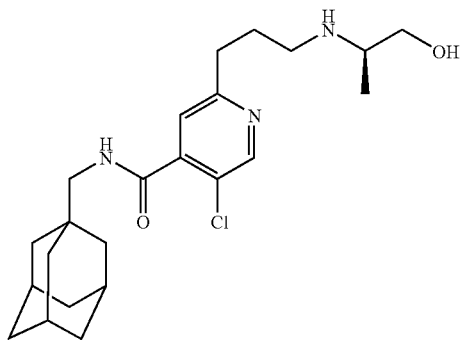

By the method outlined for Example 1(v) and using (R)-2-amino-1-propanol, the compound N-(1-adamantylmethyl)-5-chloro-2-(3-{[(1R)-2-hydroxy-1-methylethyl]amino}propyl)isonicotinamide was afforded as an oil.

$^1$H NMR (300 MHz, CDCl$_3$) δ 8.55 (1H, s); 7.45 (1H, s); 6.47 (1H, t); 3.53 (1H, dd); 3.21–3.16 (3H, m); 2.88 (2H, t); 2.81–2.69 (2H, m); 2.56–2.48 (1H, m); 2.05–1.96 (3H, m); 1.96–1.88 (2H, m); 1.76–1.63 (6H, m); 1.57–1.55 (6H, m); 1.03 (3H, d). MS: APCI(+ve) 420/422 (M+1)

The compound from above (0.100 g) was dissolved in dry hydrogen chloride in 1,4-dioxane (4N, 2 ml) and was concentrated. The residue was recrystallised from methanol: ethyl acetate to afford the titled compound (0.095 g) as a solid.

$^1$H NMR (300 MHz, DMSO-d$_6$) δ 8.62 (2H, br); 8.60 (1H, s); 8.53 (1H, t); 7.35 (1H, s); 3.65 (1H, dd); 3.47 (1H, dd); 3.22 (1H, br); 2.94 (2H, d); 2.85 (2H, t); 2.04 (2H, p); 1.98–1.96 (3H, m); 1.76–1.63 (6H, m); 1.57–1.55 (6H, m); 1.18 (3H, d). MS: APCI(+ve) 420/422 (M+1) MP: 205–208° C.

EXAMPLE 10

N-(1-Adamantylmethyl)-5-chloro-2-(3-{[(1S)-2-hydroxy-1-methylethyl]amino}propyl)isonicotinamide, dihydrochloride

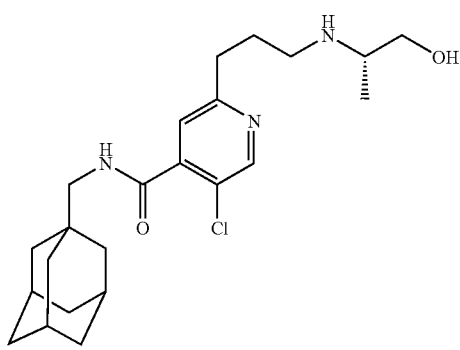

By the method outlined for Example 1(v) and using (S)-2-amino-1-propanol, the compound N-(1-adamantylmethyl)-5-chloro-2-(3-{[(1S)-2-hydroxy-1-methylethyl] amino}propyl)isonicotinamide was afforded as an oil.

$^1$H NMR (300 MHz, CDCl$_3$) δ 8.55 (1H, s); 7.45 (1H, s); 6.47 (1H, t); 3.53 (1H, dd); 3.21–3.16 (3H, m); 2.88 (2H, t); 2.81–2.69 (2H, m); 2.56–2.48 (1H, m); 2.05–1.96 (3H, m); 1.96–1.88 (2H, m); 1.76–1.63 (6H, m); 1.57–1.55 (6H, m); 1.03 (3H, d). MS: APCI(+ve) 420/422 (M+1)

The compound from above (0.060 g) was dissolved in dry hydrogen chloride in 1,4-dioxane (4N, 2 ml) and was concentrated. The residue was recrystallised from methanol: ethyl acetate to afford the titled compound (0.045 g) as a solid.

$^1$H NMR (300 MHz, DMSO-d$_6$) δ 8.62 (2H, br); 8.60 (1H, s); 8.53 (1H, t); 7.35 (1H, s); 3.65 (1H, dd); 3.47 (1H, dd); 3.22 (1H, br); 2.94 (2H, d); 2.85 (2H, t); 2.04 (2H, p); 1.98–1.96 (3H, m); 1.76–1.63 (6H, m); 1.57–1.55 (6H, m); 1.18 (3H, d). MS: APCI(+ve) 420/422 (M+1) MP: 205–208° C.

EXAMPLE 11

N-(1-Adamantylmethyl)5-chloro-2-{3-[(2-hydroxyethyl)amino]propyl}-isonicotinamide hydrochloride

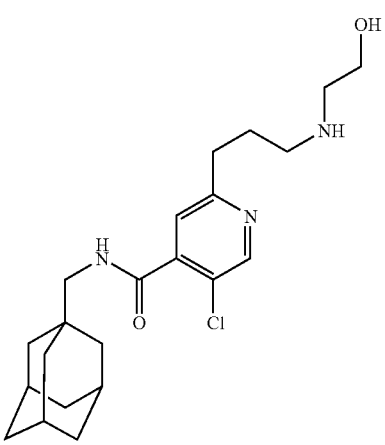

(i) tert-Butyl (2-{[tert-butyl(dimethyl)silyl]oxy}ethyl)prop-2-yn-1-ylcarbamate

The sub-titled compound was prepared from tert-butyl prop-2-yn-1-ylcarbamate (0.8 g), 60% sodium hydride (0.227 g), (2-bromoethoxy)-tert-butyldimethylsilane (1 ml) and anhydrous N-methyl-2-pyrrolidinone (4 ml) by the method of Example 2(ii). The crude product was purified by chromatography on silica gel eluting with iso-hexane:ethyl acetate (25:1) to afford (0.8 g).

$^1$H NMR (300 MHz, CDCl$_3$) δ 4.13 (2H, broad); 3.75 (2H, broad t); 3.42 (2H, t); 2.18 (1H, t); 1.47 (9H, s); 0.89 (9H, s); 0.04 (6H, s).

(ii) tert-Butyl 3-(4-{[(1-adamantylmethyl)amino] carbonyl}-5-chloropyridin-2-yl)prop-2-ynyl(2-{[tert-butyl(dimethyl)silyl]oxy}ethyl)carbamate The sub-titled compound was prepared from N-(1 adamantylmethyl)-2-bromo-5-chloroisonicotinamide (Example 2(i)) (0.37 g), tert-butyl (2-{[tert-butyl(dimethyl)silyl] oxy}ethyl)prop-2-yn-1-ylcarbamate (Example 11(i)) (0.54 g), copper (I) iodide (0.004 g), bis-triphenyphosphine palladium dichloride (0.014 g), triethylamine (6 ml) and anhydrous acetonitrile (6 ml) by the method of Example 2(iii). The crude product was purified by chromatography on silica gel eluting with, iso-hexane:ethyl acetate (8:1 to 4:1) to afford the sub-titled compound (0.28 g) as a yellow gum.

$^1$H NMR (300 MHz, CDCl$_3$) δ 8.58 (1H, s); 7.67 (1H, s); 6.23 (1H, broad); 4.40 (2H, m); 3.77 (2H, broad); 3.47 (2H, t); 3.18 (2H, d); 2.03 (3H, broad); 1.80–1.55 (12H, m); 1.48 (9H, s); 0.88 (9H, s); 0.05 (6H, s).

(iii) N-(1-Adamantylmethyl)-5-chloro-2-{3-[(2-hydroxyethyl)amino]propyl}-isonicotinamide hydrochloride The titled compound was prepared from tert-butyl 3-(4-{[(1-adamantylmethyl)amino]carbonyl}-5-chloropyridin-2- yl)prop-2-ynyl(2-{[tert-butyl(dimethyl)silyl]oxy}ethyl)carbamate (Example 11(ii)) (0.28 g) by the method of Example 6(ii). The crude hydrochloride salt was triturated with ethyl acetate to afford the titled compound (0.176 g) as a beige powder.

$^1$H NMR (300 MHz, DMSO-$d_6$) δ 8.75 (2H, broad); 8.60 (1H, s); 8.53 (1H, t); 7.35 (1H, s); 3.65 (2H, t); 3.05–2.90 (6H, m); 2.84 (2H, t); 2.04 (2H, quintet); 1.95 (3H, s); 1.64 (6H, q); 1.52 (6H, s). MS: APCI(+ve) 406/408 (M+1). MP: 204–205° C. (dec.)

EXAMPLE 12

N-(1-Adamantylmethyl)-5-chloro-2-{2-[(3-hydroxypropyl)amino]ethoxy}isonicotinamide, hydrochloride

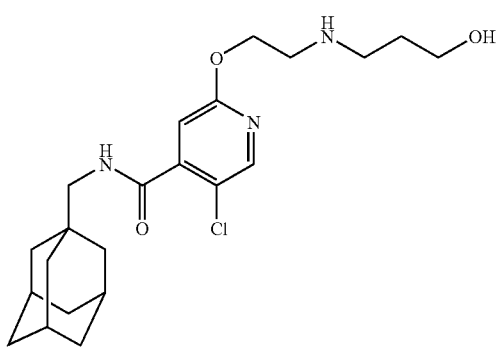

(i) N-(1-Adamantylmethyl)-5-chloro-2-(2-hydroxyethoxy)isonicotinamide

Sodium hydride (60%, 0.080 g) was added to ethylene glycol (3 ml) and the resulting suspension stirred under an atmosphere of nitrogen for 30 minutes. To this mixture was added a solution of N-(1-adamantylmethyl)-2-bromo-5-chloroisonicotinamide (Example 1(ii)) (0.192 g) in anhydrous N-methyl-2-pyrrolidinone (1 ml). The stirring bar was removed and the resulting solution heated in a MARS microwave for 15 minutes (300 Watts, 150° C.). The mixture was cooled and poured into water (50 ml) and extracted into is ethyl acetate (3×10 ml). The combined organic extracts were washed with brine (2×10 ml), dried over anhydrous magnesium sulfate, filtered and concentrated. The residue was purified by chromatography on silica gel eluting with ethyl acetate:isohexane (1:1) to afford the sub-titled compound (0.092 g) as a white solid.

$^1$H NMR (300 MHz, CDCl$_3$) δ 8.16 (1H, s); 7.09 (1H, s); 6.20 (1H, br); 4.45 (2H, dd); 3.96 (2H, ddd); 3.17 (2H, d); 2.54 (1H, t); 2.05–1.96 (3H, m); 1.76–1.73 (3H, m); 1.66–1.63 (3H, m); 1.57–1.55 (6H, m). MS: APCI(+ve) 364/366 (M+1) MP: 154–155° C.

(ii) N-(1-Adamantylmethyl)-5-chloro-2-{2-[(3-hydroxypropyl)amino]ethoxy}isonicotinamide, hydrochloride To a stirred solution of N-(1-adamantylmethyl)-5-chloro-2-(2-hydroxyethoxy)isonicotinamide (Example 12(i)) (0.10 g) in dry dichloromethane (5 ml) was added Dess-Martin periodinane (0.212 g) and the resulting suspension stirred at room temperature for 30 minutes. The reaction was poured into a mixture of saturated sodium bicarbonate solution containing sodium thiosulfate (10% w/v, 20 ml) and the mixture was extracted into ethyl acetate (3×25 ml). The combined extracts were dried over anhydrous magnesium sulfate, filtered and concentrated. The crude aldehyde was dissolved in methanol (2 ml) and 3-aminopropan-1-ol (0.075 g) added along with acetic acid (0.1 ml). The mixture was stirred for 2 hours at ambient temperature and then sodium triacetoxy borohydride (0.159 g) added and the reaction stirred for 20 hours, concentrated and the residue was partitioned between 2M aqueous hydrochloric acid solution and ethyl acetate (2×10 ml). The layers were separated and the organic phase re-extracted with 2N hydrochloric acid (2×10 ml). The combined aqueous extracts were basified with 5M aqueous ammonium hydroxide solution, extracted into ethyl acetate (2×25 ml) and the combined extracts were dried over anhydrous magnesium sulfate, filtered and concentrated to afford the compound, N-(1-adamantylmethyl)-5-chloro-2-{2-[(3-hydroxypropyl)amino] ethoxy}isonicotinamide (0.05 g), as a foam.

$^1$H NMR (400 MHz, CDCl$_3$) δ 8.15 (1H, s); 7.01 (1H, s); 6.31 (1H, br); 4.41 (2H, t); 3.80 (2H, d); 3.16 (2H, d); 3.00 (2H, t); 2.94 (3H, t); 2.05–1.96 (3H, m); 1.76–1.73 (5H, m); 1.66–1.63 (3H, m); 1.57–1.55 (6H, m). MS: APCI(+ve) 421/423 (M+1)

The compound from above (0.050 g) was dissolved in dry hydrogen chloride in 1,4-dioxane (4N, 2 ml) and was concentrated. The residue was triturated with dry ether and filtered to afford N-(1-adamantylmethyl)-5-chloro-2-{2-[(3-hydroxypropyl)amino]ethoxy}isonicotinamide hydrochloride (0.024 g) as a white solid.

$^1$H NMR (300 MHz, DMSO-$d_6$) δ 8.85 (2H, broad); 8.57 (1H, s); 8.54 (1H, t); 8.34 (1H, s); 6.86 (1H, s); 4.53 (2H, t); 3.54 (2H, t); 3.38–3.32 (2H, m); 3.06–3.02 (2H, m); 2.94 (2H, d); 1.94 (3H, s); 1.88–1.82 (2H, m); 1.76–1.73 (3H, m); 1.66–1.63 (3H, m); 1.57–1.55 (6H, m). MS: APCI(+ve) 421/423 (M+1)

EXAMPLE 13

N-(1-Adamantylmethyl)-5-chloro-2-({2-[(2-hydroxyethyl)amino]ethyl}-amino)isonicotinamide dihydrochloride

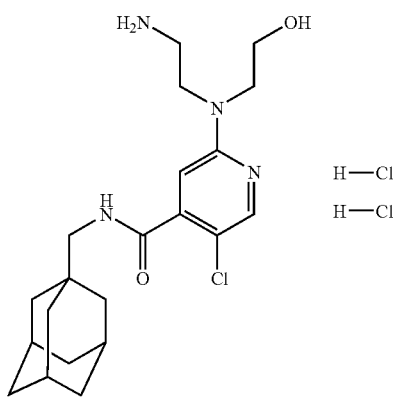

(i) tert-Butyl 2-[(4-{[(1-adamantylmethyl)amino] carbonyl}-5-chloropyridin-2-yl)(2-hydroxyethyl) amino]ethylcarbamate N-(2-Hydroxyethyl)-ethylenediamine (0.208 g) was added to a mixture of N-(1-adamantylmethyl)-2-bromo-5-chloroisonicotinamide (0.192 g, Example 1(ii)) and potassium carbonate (0.14 g) in anhydrous N-methyl-2-pyrrolidinone (3 ml). The resulting solution heated in a MARS microwave for 10 minutes (300 Watts, 150° C.). The mixture was cooled and poured into water (50 ml) and extracted into ethyl acetate (3×10 ml). The combined organic extracts were washed with brine (2×10 ml), dried over anhydrous magnesium sulfate, filtered and concentrated. The residue was dissolved into ethyl acetate 30 ml and di-tert-butylcarbonate (0.218 g) added. The resulting mixture was left to stand at room temperature for 2 hours and was then concentrated under reduced pressure. The residue was purified by chromatography on silica gel eluting with ethyl acetate to afford tert-butyl 2-[(4-{[(1-adamantylmethyl)amino]carbonyl}-5-chloropyridin-2-yl)(2-hydroxyethyl)amino]ethylcarbamate (0.013 g).

$^1$H NMR (300 MHz, CDCl$_3$) δ 8.08 (1H, s); 6.96 (1H, s); 6.43 (1H, br); 4.95 (1H, br); 3.83 (2H, t); 3.70–3.62 (4H, m); 3.67 (2H, q); 3.17 (2H, d); 2.05–1.96 (3H, m); 1.76–1.73 (3H, m); 1.66–1.63 (3H, m); 1.57–1.55 (6H, m); 1.37 (9H, s). MS: APCI(+ve) 507, 509 (M+1)

(ii) N-(1-Adamantylmethyl)-5-chloro-2-({2-[(2-hydroxyethyl)amino]ethyl}-amino)isonicotinamide dihydrochloride tert-Butyl 2-[(4-{[(1-adamantylmethyl)amino]carbonyl}-5-chloropyridin-2-yl)(2-hydroxyethyl)amino]ethylcarbamate (Example 13(i)) (0.013 g) was dissolved in anhydrous hydrogen chloride in 1,4-dioxane (4M, 2 ml) and the resulting mixture was allowed to stand at room temperature for 30 minutes. The mixture was concentrated under reduced pressure to afford the titled product (0.020 g).

$^1$H NMR (300 MHz, DMSO-d$_6$) δ 8.39 (1H, t); 8.11 (1H, s); 7.85 (2H, br); 6.69 (1H, s); 3.74 (2H, t); 3.07–3.96 (4H, br); 2.92 (2H, d); 1.94 (3H, s); 1.76–1.73 (3H, m); 1.66–1.63 (3H, m); 1.57–1.55 (6H, m). MS: APCI(+ve) 407, 409 (M+1)

EXAMPLE 14

N-(1-Adamantylmethyl)-5-chloro-2-[3-(isopropylamino)propyl]isonicotinamide dihydrochloride

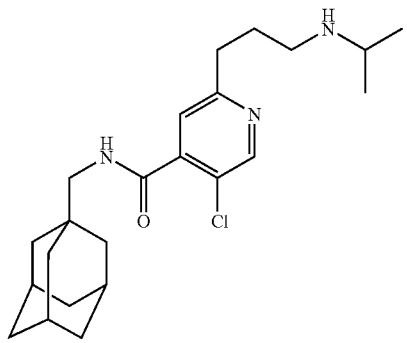

(i) N-(1-Adamantylmethyl)-2-(3-{[tert-butyl(dimethyl)silyl]oxy}propyl)-5-chloroisonicotinamide A solution of 9-borabicyclo[3.3.1]nonane at 0.5 M in tetrhydrofuran (2.78 mL, 1.39 mmol) was added to neat (allyloxy)(tert-butyl)dimethylsilane (0.15 mL, 0.69 mmole). The mixture was heated to 60° C. for 2 hours under nitrogen. The reaction was subsequently cooled to room temperature and a solution of potassium phosphate (0.37 g) in water (1 mL) was added slowly. A solution of N-(1-adamantylmethyl)-2,5-dichloroisonicotinamide (0.20 g, 0.59 mmol; prepared as described in WO 01/94338) in dimethylformamide (3 mL) was added followed by tetrakis(triphenyphosphine) palladium (0) (7 mg). The solution was heated to 70° C. for 2 hours; allowed to cool to room temperature then partitioned between ethyl acetate (20 mL) and brine (10 mL). The aqueous phase was further extracted with ethyl acetate (2×20 mL) and the combined organics were washed with brine (20 mL); dried over magnesium sulphate; filtered and evaporated under vacuum to give the crude product (0.70 g) as a yellow oil, which was used, as such, without any further purification.

(ii) N-(1-Adamantylmethyl)-5chloro-2-(3-hydroxypropyl)isonicotinamide

The residue from above was dissolved in tetrahydrofuran (10 mL) and cooled to 0° C. To this a solution of tetra-n-butyl ammonium fluoride (0.75 mL of a 1M solution) was added and the mixture warmed to room temperature for 2 hours. After this time the solution was cooled to 0° C. and treated with 0.6 mL of tetra-n-butyl ammonium fluoride and stirring continued for an additional hour at room temperature. The reaction mixture was subsequently diluted with diethyl ether (30 mL); washed with water (2×10 mL); brine (20 mL); dried over magnesium sulphate; filtered and evaporated under vacuum. The residue was purified by chromatography on silica gel eluting with dichloromethane:ethyl acetate:methanol (15:4:1) to afford the sub-titled compound (0.21 g) as a clear oil.

$^1$H NMR (400 MHz, CDCl$_3$) δ 8.55 (1H, s); 7.51 (1H, s); 6.32 (1H, bs); 3.69 (2H, t); 3.19 (2H, d); 2.96 (2H, t); 1.96–2.05 (5H, m); 1.70 (6H, q); 1.58 (6H, s) MS: APCI(+ve) 363, 365 (M+1).

(iii) N-(1-Adamantylmethyl)-5-chloro-2-(3-oxopropyl)isonicotinamide

To a stirred solution of N-(1-adamantylmethyl)-5-chloro-2-(3-hydroxypropyl)isonicotinamide (0.12 g, 0.33 mmol) (Example 14(ii)) in dry dichloromethane (10 mL) Dess-Martin periodinane (0.14 g, 0.33 mmol) was added. The resulting mixture was stirred at room temperature for 4 hours. The reaction was treated with diethyl ether (20 mL) and a saturated sodium bicarbonate solution containing sodium thiosulfate (0.37 g, in 4 mL). The mixture was stirred for 10 minutes and the organics separated; washed with brine (10 mL); dried over anhydrous magnesium sulfate; filtered; treated with acetic acid (0.30 mL) and concentrated. MS: APCI(+ve) 361, 363 (M+1).

(iv) N-(1-Adamantylmethyl)-5-chloro-2-[3-(isopropylamino)propyl]isonicotinamide dihydrochloride The crude aldehyde from above was dissolved in methanol (2 mL) and treated with isopropylamine (0.084 mL, 0.99 mmol) along with acetic acid (0.10 mL). The mixture was stirred for 10 minutes at ambient temperature and then sodium triacetoxy borohydride (0.14 g, 0.66 mmol) was added. The reaction was stirred for 20 hours, concentrated and the residue dissolved in ethyl acetate (20 mL). The organics were washed with a saturated solution of sodium bicarbonate (10 mL); brine (10 mL); dried over anhydrous magnesium sulfate; filtered and concentrated to afford an oil (0.118 g). The crude compound was dissolved in dichloromethane (5 mL); treated with dry hydrogen chloride in 1,4-dioxane (4N, 0.4 mL) and was concentrated after 10 minutes. The residue was filtered from dichloromethane (20 mL) to afford the titled compound (0.098 g) as a white solid.

$^1$H NMR (400 MHz, DMSO-$d_6$) δ 8.61–8.51 (3H, m); 3.32–3.26 (1H, m); 2.95–2.84 (6H, m); 2.05–2.00 (2H, m); 1.98 (3H, s); 1.68 (6H, q); 1.59 (6H, s); 1.22 (6H, d). MS: APCI(+ve) 404, 406 (M+1).

EXAMPLE 15

N-(1-Adamantylmethyl)-5-chloro-2-(3-{[(2S)-2-hydroxypropyl]amino}propyl)isonicotinamide, dihydrochloride

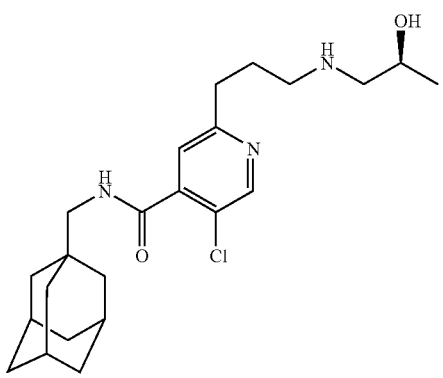

By the method outlined for Example 14(iv) and using (2S)-1-aminopropan-2-ol, the compound, N-(1-adamantylmethyl)-5-chloro-2-(3-{[(2S)-2-hydroxypropyl]amino}propyl)isonicotinamide, was afforded as an oil. Purification was by preparative reverse phase HPLC. The isolated material (0.081 g) was dissolved in a solution of hydrogen chloride in 1,4-dioxane (1 mL of a 4M solution) and concentrated to afford the titled compound as a colorless powder (0.091 g).

$^1$H NMR (400 MHz, DMSO-$d_6$) δ 8.91 (1H, bs); 8.71(1H, bs); 8.60 (1H, s); 8.56 (1H, t); 3.99–3.94 (1H, m); 2.95–2.94 (5H, m); 2.85 (2H, t); 2.76–2.70 (1H, m); 2.10–2.02 (2H, m); 1.95 (3H, s); 1.64 (6H, q); 1.52 (6H, s); 1.10 (3H, d). MS: APCI(+ve) 420, 422 (M+1).

EXAMPLE 16

N-(1-Adamantylmethyl)-5-chloro-2-(3-{[(2R)-2,3-dihydroxypropyl]amino}propyl)isonicotinamide, dihydrochloride

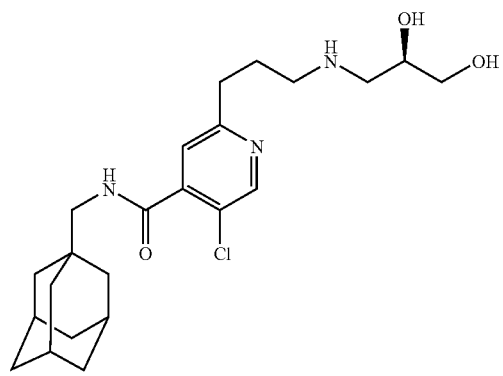

By the method outlined for Example 14(iv) and using (2R)-3-aminopropane-1,2-diol, the compound, N-(1-adamantylmethyl)-5-chloro-2-(3-{[(2R)-2,3-dihydroxypropyl]amino}propyl)isonicotinamide, was afforded as an oil. The residue was purified by chromatography on silica gel eluting with dichloromethane:methanol:ammonia (10:1:1). The isolated material was dissolved in dichloromethane, treated with a solution of hydrogen chloride in 1,4-dioxane (1 mL of a 4M solution) and concentrated to afford the titled compound as a colorless powder (0.098 g).

$^1$H NMR (400 MHz, CD$_3$OD) δ 8.65–8.62 (2H, m); 7.44 (1H, s); 3.90–3.87 (1H, m); 3.55 (2H, dq); 3.20–2.97 (8H, m); 2.18–2.11 (2H, m); 1.99 (3H, s); 1.73 (6H, q); 1.62 (6H, s). MS: APCI(+ve) 436, 438 (M+1). MP: 217–219° C.

EXAMPLE 17

N-(1-Adamantylmethyl)-5-chloro-2-(3-{[(2S)-2,3-dihydroxypropyl]amino}propyl)isonicotinamide, dihydrochloride

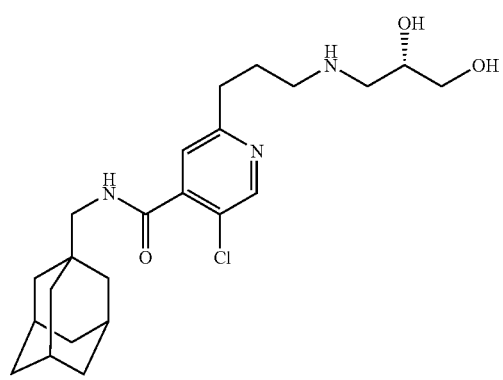

By the method outlined for Example 14(iv) and using (2S)-3-aminopropane-1,2-diol, the compound, N-(1-adamantylmethyl)-5-chloro-2-(3-{[(2S)-2,3-dihydroxypropyl]amino}propyl)isonicotinamide, was afforded as an oil. The residue was purified by chromatography on silica gel eluting with dichloromethane:methanol:ammonia (10:1:1). The isolated material was dissolved in dichloromethane, treated with a solution of hydrogen chloride in 1,4-dioxane (1 mL of a 4M solution) and concentrated to afford the titled compound as a colorless powder (0.057 g).

$^1$H NMR (400 MHz, CD$_3$OD) δ 8.64 (2H, s); 7.45 (1H, s); 3.92–3.89 (1H, m); 3.55 (2H, dq); 3.20–2.97 (8H, m); 2.18–2.11 (2H, m); 1.99 (3H, s); 1.73 (6H, q); 1.62 (6H, s). MS: APCI(+ve) 436, 438 (M+1).

EXAMPLE 18

N-(1-Adamantylmethyl)-5-chloro-2-{3-[(4-methylcyclohexyl)amino]propyl}isonicotinamide dihydrochloride

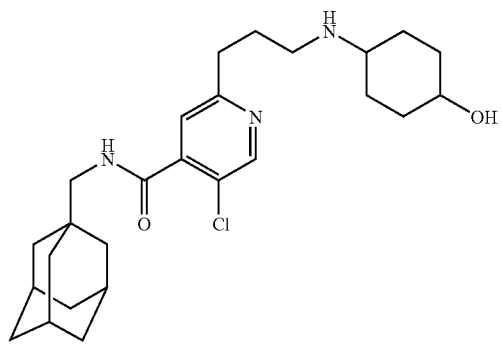

By the method outlined for Example 14(iv) and using 4-aminocyclohexanol, the titled compound, N-(1-adamantylmethyl)-5-chloro-2-{3-[(4-methylcyclohexyl)amino]propyl}isonicotinamide, was afforded as an oil. Purification was by preparative reverse phase HPLC. The isolated material (0.022 g) was dissolved in dichloromethane, treated with a solution of hydrogen chloride in 1,4-dioxane (1 mL of a 4M solution) and concentrated to afford the titled compound as a colorless powder (0.025 g).

$^1$H NMR (300 MHz, CD$_3$OD) δ 8.63 (1H, s); 7.39 (1H, s); 3.61–3.58 (1H, m); 3.10–3.01 (5H, m); 2.96 (2H, t); 2.19–2.00 (5H, m); 1.70 (6H, q); 1.64 (6H, s); 1.47–1.30 (8H, m). MS: APCI(+ve) 460, 462 (M+1). MP: 242–244° C.

EXAMPLE 19

N-(1-Adamantylmethyl)-5-chloro-2-{3-[(2-hydroxy-2-methylpropyl)amino]propyl}isonicotinamide dihydrochloride

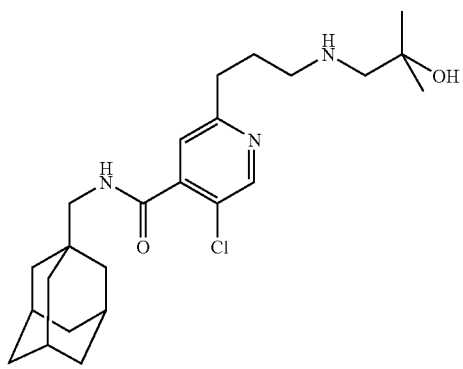

By the method outlined for Example 14(iv) and using 1-amino-2-methylpropan-2-ol, the titled compound, N-(1-adamantylmethyl)-5-chloro-2-{3-[(2-hydroxy-2-methylpropyl)amino]propyl}isonicotinamide, was afforded as an oil. Purification was by preparative reverse phase HPLC. The isolated material (0.015 g) was dissolved in dichloromethane, treated with a solution of hydrogen chloride in 1,4-dioxane (1 mL of a 4M solution) and concentrated to afford the titled compound as a colorless powder (0.019 g).

$^1$H NMR (300 MHz, CD$_3$OD) δ 8.65 (1H, s); 7.44 (1H, s); 3.16–3.09 (4H, m); 3.01 (4H, t); 2.21–2.16 (2H, m); 2.00 (3H, s); 1.75 (6H, q); 1.64 (6H, d); 1.33 (6H, s). MS: APCI(+ve) 434, 436 (M+1). MP: 236–238° C.

EXAMPLE 20

N-(1-Adamantylmethyl)-5-chloro-2-(3-{[(1R)-1-(hydroxymethyl)-2-methylpropyl]amino}propyl)isonicotinamide, dihydrochloride

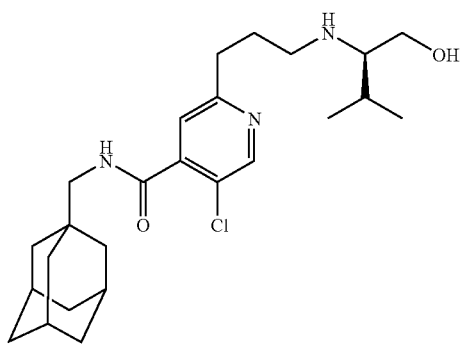

By the method outlined for Example 14(iv) and using (2R)-2-amino-3-methylbutan-1-ol, the compound, N-(1-adamantylmethyl)-5-chloro-2-(3-{[(1R)-1-(hydroxymethyl)-2-methylpropyl]amino}propyl)isonicotinamide, was afforded as an oil. Purification was by preparative reverse phase HPLC. The isolated material (0.065 g) was dissolved in dichloromethane, treated with a solution of hydrogen chloride in 1,4-dioxane (1 mL of a 4M solution) and concentrated to afford the titled compound as a colorless powder (0.071 g).

$^1$H NMR (400 MHz, DMSO-d$_6$) δ 8.60 (1H, s); 8.54 (1H, bt); 8.36 (1H, bs); 7.36 (1H, s); 3.72–3.68 (1H, m); 3.63–3.57 (2H, m); 3.16–3.04 (2H, bm); 2.94 (2H, d); 2.87 (2H, t); 2.11–2.02 (4H, m); 1.95 (3H, s); 1.64 (6H, q); 1.52 (6H, s); 0.98 (3H, d); 0.94 (3H, d). MS: APCI(+ve) 448, 450 (M+1).

EXAMPLE 21

N-(1-Adamantylmethyl)-5-chloro-2-(3-{[2-(methylamino)ethyl]amino}propyl)isonicotinamide dihydrochloride

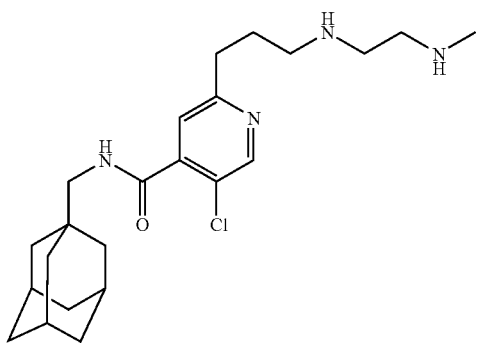

By the method outlined for Example 14(iv) and using tert-butyl 2-aminoethyl(methyl)carbamate, tert-butyl 2-{[3-(4-{[(1-adamantylmethyl)amino]carbonyl}-5-chloropyridin-2-yl)propyl]amino}ethyl(methyl)carbamate was afforded as an oil. The latter (0.118 g) was dissolved in dichloromethane and treated with dry hydrogen chloride in 1,4-dioxane (4N, 1 mL) and was concentrated after 2 hours to give the deprotected material. The residue was recrystallised from dichloromethane (3 ml) to afford the titled compound (0.035 g) as a white solid.

$^1$H NMR (300 MHz, CD$_3$OD) δ 8.71 (1H, s); 7.54 (1H, s); 3.43 (4H, s); 3.22–3.17 (4H, m); 3.09–3.02 (4H, m); 2.81 (3H, s); 2.24–2.19 (2H, m); 2.01 (3H, s); 1.75 (6H, q); 1.64 (6H, s); MS: APCI(+ve) 419, 421 (M+1). MP: 216–219° C.

EXAMPLE 22

N-(1-Adamantylmethyl)-5-chloro-2-(3-{[3-(methylamino)propyl]amino}propyl)isonicotinamide bis(trifluoroacetate)

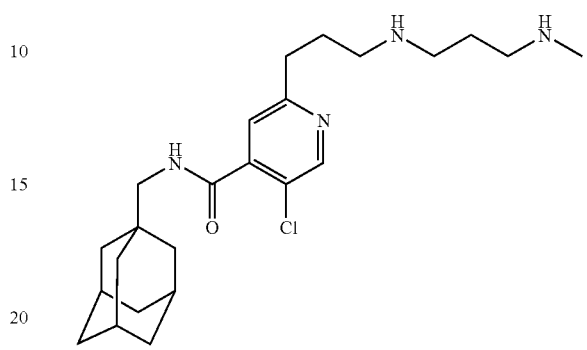

By the method outlined for Example 14(iv) and using tert-butyl 3-aminopropyl(methyl)carbamate, tert-butyl 3-{[3-(4-{[(1-adamantylmethyl)amino]carbonyl}-5-chloropyridin-2-yl)propyl]amino}propyl(methyl)carbamate was afforded as an oil. The latter (0.121 g) was dissolved in dichloromethane and treated with dry hydrogen chloride in 1,4-dioxane (4N, 1 mL) and was concentrated after 2 hours to give the deprotected material. The residue was purified by preparative reverse phase HPLC to afford the titled compound (0.028 g) as a white solid.

$^1$H NMR (400 MHz, CD$_3$OD) δ 8.57 (1H, s); 7.33 (1H, s); 3.13–3.06 (8H, m); 2.93 (2H, t); 2.72 (3H, s); 2.16–2.05 (4H, m); 1.98 (3H, s); 1.75 (6H, q); 1.62 (6H, s). MS: APCI(+ve) 433, 435 (M+1). MP: 210–212° C.

EXAMPLE 23

N-(1-Adamantylmethyl)-5-chloro-2-[3-({2-[(2-hydroxyethyl)amino]ethyl}amino)propyl]isonicotinamide dihydrochloride

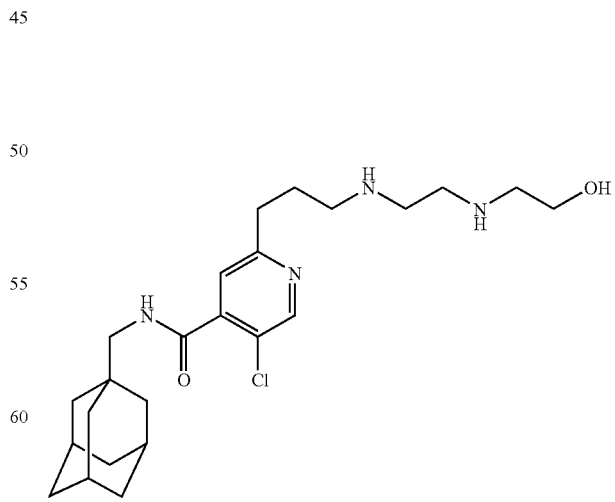

By the method outlined for Example 14(iv) and using tert-butyl 2-aminoethyl(2-hydroxyethyl)carbamate, tert-butyl 2-{[3-(4-{[(1-adamantylmethyl)amino]carbonyl}-5-chloropyridin-2-yl)propyl]amino}ethyl(2-hydroxyethyl) carbamate was afforded as an oil. The latter (0.062 g) was dissolved in dichloromethane and treated with dry hydrogen chloride in 1,4-dioxane (4N, 1 mL) and was concentrated after 2 hours to give the deprotected material. The residue was recrystallised from dichloromethane (3 mL) to afford the titled compound (0.006 g) as a white solid.

$^1$H NMR (300 MHz, CD$_3$OD) δ 8.61 (1H, s); 7.39 (1H, s); 3.86 (2H, t); 3.47 (4H, t); 3.27–3.16 (4H, m); 3.10–3.08 (2H, m); 2.99 (2H, t); 2.22–2.17 (2H, m); 2.01 (3H, s); 1.75 (6H, q); 1.64 (6H, d). MS: APCI(+ve) 449, 451 (M+1). MP: 231–233° C.

EXAMPLE 24

N-(1-Adamantylmethyl)-5-chloro-2-(3-{[2-(diethylamino)ethyl]amino}propyl)isonicotinamide dihydrochloride

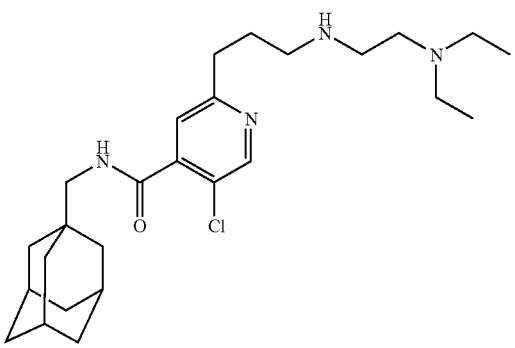

By the method outlined for Example 14(iv) and using N,N-diethylethane-1,2-diamine, the titled compound, N-(1-adamantylmethyl)5-chloro-2-(3-{[2-(diethylamino)ethyl]amino}propyl)isonicotinamide, was afforded as an oil. Purification was by preparative reverse phase HPLC. The isolated material (0.057 g) was dissolved in dichloromethane, treated with a solution of hydrogen chloride in 1,4-dioxane (1 mL of a 4M solution) and concentrated to afford the titled compound as a colorless powder (0.062 g).

$^1$H NMR (400 MHz, CD$_3$OD) δ 8.62 (1H, s); 7.43 (1H, s); 3.51 (4H, s); 3.35–3.31 (2H, m); 3.18 (2H, t); 3.08 (2H, s); 2.99 (2H, t); 2.21–2.17 (2H, m); 1.99 (3H, s); 1.74 (6H, q); 1.63 (6H, s). MS: APCI(+ve) 461, 463 (M+1).

EXAMPLE 25

N-(1-Adamantylmethyl)-5-chloro-2-(3-{[2-hydroxy-1-(hydroxymethyl)ethyl]amino}propyl)isonicotinamide dihydrochloride

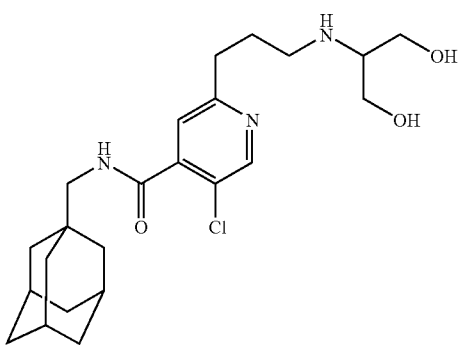

By the method outlined for Example 14(iv) and using 2-aminopropane-1,3-diol, the titled compound, N-(1-adamantylmethyl)-5-chloro-2-(3-{[2-hydroxy-1-(hydroxymethyl)ethyl]amino}propyl)isonicotinamide, was afforded as an oil. Purification was by preparative reverse phase HPLC. The isolated material (0.072 g) was dissolved in dichloromethane, treated with a solution of hydrogen chloride in 1,4-dioxane (1 mL of a 4M solution) and concentrated to afford the titled compound as a colorless powder (0.080 g).

$^1$H NMR (400 MHz, CD$_3$OD) δ 8.61 (1H, s); 7.40 (1H, s); 3.80 (2H, dd); 3.73 (2H, dd); 3.19 (2H, t), 3.07 (2H, s); 2.99 (2H, t); 2.19–2.11 (2H, m); 1.98 (3H, s); 1.73 (6H, q); 1.61 (6H, s). MS: APCI(+ve) 436, 438 (M+1). MP: 201–203° C.

EXAMPLE 26

N-(1-Adamantylmethyl)-5chloro-2-{3-[(2-hydroxyethyl)(methyl)amino]propyl}isonicotinamide dihydrochloride

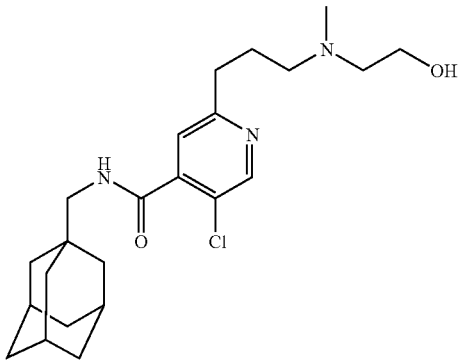

By the method outlined for Example 14(iv) and using 2-(methylamino)ethanol, the titled compound, N-(1-adamantylmethyl)-5-chloro-2-{3-[(2-hydroxyethyl)(methyl)amino]propyl}isonicotinamide, was afforded as an oil. Purification was by preparative reverse phase HPLC. The isolated material (0.061 g) was dissolved in dichloromethane, treated with a solution of hydrogen chloride in 1,4-dioxane (1 mL of a 4M solution) and concentrated to afford the titled compound as a white powder (0.069 g).

$^1$H NMR (400 MHz, CD$_3$OD) δ 8.64 (2H, bs); 7.46 (1H, s); 3.87–3.84 (2H, m); 3.39–3.16 (4H, m); 3.07 (2H, s); 2.99 (2H, t); 2.91 (3H; s); 2.24–2.16 (2H, m); 1.98 (3H, s); 1.73 (6H, q); 1.61 (6H, s). MS: APCI(+ve) 420, 422 (M+1). MP: 206–208° C.

EXAMPLE 27

N-(1-Adamantylmethyl)-5-chloro-2-{3-[(3-hydroxy-2,2-dimethylpropyl)amino]propyl}isonicotinamide dihydrochloride

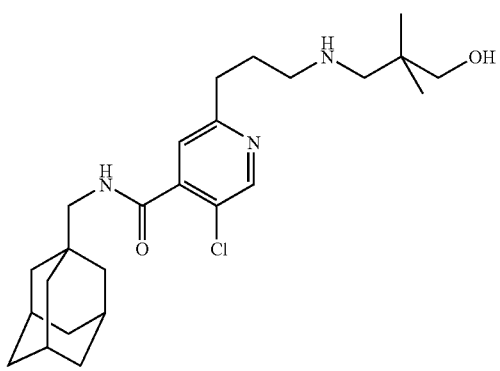

By the method outlined for Example 14(iv) and using 3-amino-2,2-dimethylpropan-1-ol, the titled compound, N-(1-adamantylmethyl)-5-chloro-2-{3-[(3-hydroxy-2,2-dimethylpropyl)amino]propyl}isonicotinamide, was afforded as an oil. The compound from above (0.122 g) was dissolved in dichloromethane and treated with dry hydrogen chloride in 1,4-dioxane (4N, 0.4 mL) and was concentrated after 10 minutes. The residue was filtered from dichloromethane (20 mL) to afford the titled compound (0.091 g) as a solid.

$^1$H NMR (300 MHz, CD$_3$OD) δ 8.66 (1H, s), 7.44 (1H, s); 3.49 (2H, s); 3.13–3.08 (4H, m); 3.01–2.96 (4H, m); 2.23–2.12 (2H, m); 2.00 (3H, s); 1.75 (6H, q); 1.64 (6H, d); 1.05 (6H, s). MS: APCI(+ve) 448, 450 (M+1).

EXAMPLE 28

N-(1-Adamantylmethyl)-5-chloro-2-(3-{[(2R)-2-hydroxypropyl]amino}propyl)isonicotinamide, dihydrochloride

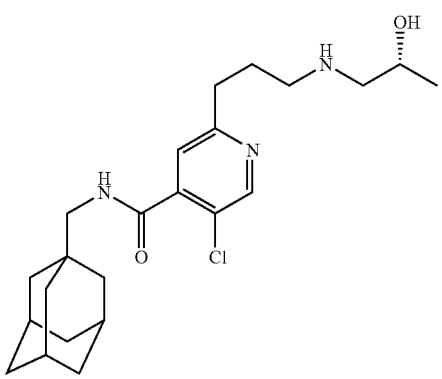

By the method outlined for Example 14(iv) and using (2R)-1-aminopropan-2-ol, the compound, N-(1-adamantylmethyl)-5-chloro-2-(3-{[(2R)-2-hydroxypropyl]amino}propyl)isonicotinamide, was afforded as an oil. The compound from above (0.062 g) was dissolved in dichloromethane and treated with dry hydrogen chloride in 1,4-dioxane (4N, 0.4 mL) and was concentrated after 10 minutes. The residue was filtered from dichloromethane (10 mL) to afford the titled compound (0.033 g) as a solid.

$^1$H NMR (400 MHz, CD$_3$OD) δ 8.57 (2H, bs); 7.35 (1H, s); 4.04–3.96 (1H, m); 3.10–3.06 (4H, m); 2.95 (2H, t); 2.85 (2H, t); 2.16–2.10 (2H, m); 1.98 (3H, s); 1.73 (6H, q); 1.62 (6H, s); 1.21 (3H, d). MS: APCI(+ve) 420, 422 (M+1). MP: 224–226° C.

EXAMPLE 29

N-(1-Adamantylmethyl)-5chloro-2-({[3-(methylamino)propyl]amino}methyl)isonicotinamide dihydrochloride

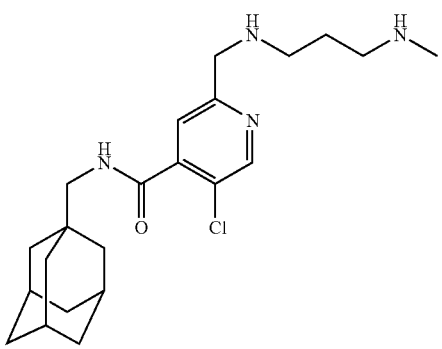

(i) N-(1-Adamantylmethyl)-5chloro-2-vinylisonicotinamide

N-(1-Adamantylmethyl)-2,5-dichloroisonicotinamide (2.32 g) and tributyl(vinyl)stannane (2.61 g) were stirred together in dry N,N-dimethylformamide (50 mL) at room temperature under nitrogen. The latter was treated with a few crystals of 2,6-ditert-butyl-4-methylphenol and dichloro[bis(triphenylphosphine)]palladium(II) (0.24 g). The reaction mixture was warmed to 80° C. for 4 hours and subsequently cooled to room temperature. The mixture was poured into ethyl acetate (50 mL) and washed with water (2×25 mL) then brine (30 mL). The organics were dried over anhydrous magnesium sulfate, filtered and concentrated. The residue was purified by chromatography on silica gel eluting with ethyl acetate:dichloromethane (1:20) to afford the sub-titled compound (2.21 g).

$^1$H NMR (300 MHz, CDCl$_3$) δ 8.58 (1H, s); 7.62 (1H, s); 6.79 (1H, dd); 6.36 (1H, bs); 6.25 (1H, dd); 5.56 (1H, dd); 3.19 (2H, d); 1.98 (3H, s); 1.70 (6H, q); 1.59 (6H, s). MS: APCI(+ve) 331, 333 (M+1).

(ii) N-(1-Adamantylmethyl)-5-chloro-2-formylisonicotinamide

N-(1-Adamantylmethyl)-5-chloro-2-vinylisonicotinamide (Example 29(i)) (1.70 g) was dissolved in dichloromethane (50 mL), treated with acetic acid (1 mL) and cooled to −78° C. under nitrogen. Ozone was bubbled through the resulting solution for 2 hours while maintaining the temperature. Nitrogen was subsequently bubbled through the solution for 10 minutes and dimethylsulfide (2 mL) was added. The solution was warmed to room temperature washed with sodium bicarbonate (2×10 mL) and brine (30 mL); the organics were dried over anhydrous magnesium sulfate, filtered and concentrated. The residue was purified by chromatography on silica gel eluting with ethyl acetate:dichloromethane (1:20) to afford the sub-titled compound (1.13 g).

$^1$H NMR (300 MHz, CDCl$_3$) δ 10.06 (1H, s); 8.81 (1H, s); 8.15 (1H, s); 6.20 (1H, bs); 3.17 (2H, d); 2.02 (3H, s); 1.70 (6H, q); 1.58 (6H, s). MS: APCI(+ve) 333, 335 (M+1).

(iii) N-(1-Adamantylmethyl)-5-chloro-2-({[3-(methylamino)propyl]amino}methyl)isonicotinamide dihydrochloride N-(1-Adamantylmethyl)-5-chloro-2-formylisonicotinamide (Example 29(ii)) (0.2 g) was dissolved in methanol (10 mL) and tert-butyl 3-aminopropyl(methyl)carbamate, (0.39 g) added along with acetic acid (0.2 mL). The mixture was stirred for 15 minutes at ambient temperature and then sodium triacetoxyborohydride (0.25 g) was added and the reaction stirred for 20 hours, concentrated and the residue partitioned between 2M aqueous hydrochloric acid solution (10 mL) and ethyl acetate (10 mL). The layers were separated and the organic phase re-extracted with 2N hydrochloric acid (2×10 mL). The combined aqueous extracts were basified with 5M aqueous ammonium hydroxide solution, extracted into ethyl acetate (2×25 mL) and the combined extracts were dried over anhydrous magnesium sulfate, filtered and concentrated. The residue was dissolved in dichloromethane and treated with dry hydrogen chloride in 1,4-dioxane (4N, 1 mL) and was concentrated after 2 hours to give the deprotected material. The residue was recrystallised from dichloromethane (10 mL) to afford the titled compound (0.110 g).

$^1$H NMR (300 MHz, CD$_3$OD) δ 8.75 (1H, s); 8.67 (1H, bt); 7.56 (1H, s); 4.48 (2H, s); 3.27 (2H, t); 3.18–3.09 (4H, m); 2.75 (3H, s); 2.25–2.15 (2H, m); 2.01 (3H, s); 1.76 (6H, q); 1.65 (6H, s). MS: APCI(+ve) 405, 407 (M+1). MP: 285–287° C.

EXAMPLE 30

N-(1-Adamantylmethyl)-5-chloro-2-[({2-[(2-hydroxyethyl)amino]ethyl}amino)methyl]isonicotinamide dihydrochloride

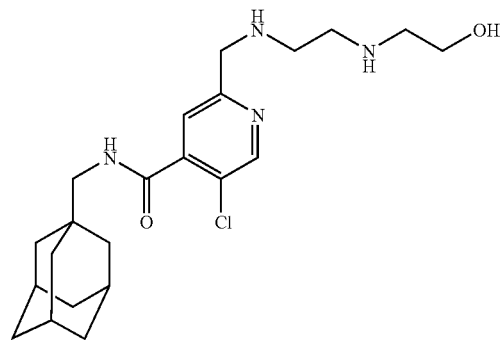

By the method outlined for Example 29 (iii) and using tert-butyl 2-aminoethyl(2-hydroxyethyl)carbamate, tert-butyl 2-{[(4-{[(1-adamantylmethyl)amino]carbonyl}-5-chloropyridin-2-yl)methyl]amino}ethyl(2-hydroxyethyl)carbamate was afforded as an oil. The latter was dissolved in dichloromethane and treated with dry hydrogen chloride in 1,4-dioxane (4N, 1 mL) and was concentrated after 2 hours to give the deprotected material. The residue was recrystallised from dichloromethane (5 mL) to afford the titled compound (0.118 g) as a white solid.

$^1$H NMR (400 MHz, CD$_3$OD) δ 8.76 (1H, s); 8.64 (1H, t); 7.55 (1H, s); 4.51 (2H, s); 3.85–3.83 (2H, m); 3.57–3.32 (4H, m); 3.23–3.21 (2H, m); 3.08 (2H, d); 1.99 (3H, s); 1.74 (6H, q); 1.62 (6H, s). MS: APCI(+ve) 421, 423 (M+1). MP: 289–292° C.

EXAMPLE 31

N-(1-Adamantylmethyl)-5-chloro-2-({[2-(methylamino)ethyl]amino}methyl)isonicotinamide dihydrochloride

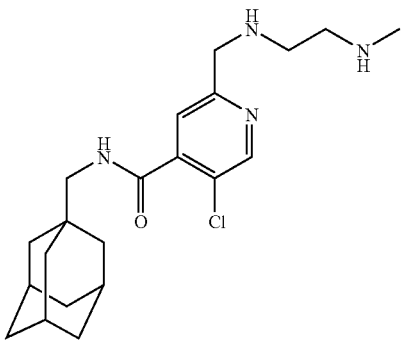

By the method outlined for Example 29 (iii) and using tert-butyl 2-aminoethyl(methyl)carbamate, tert-butyl 2-{[(4-{[(1-adamantylmethyl)amino]carbonyl}-5-chloropyridin-2-yl)methyl]amino}ethyl(methyl)carbamate was afforded as an oil. The latter was dissolved in dichloromethane and treated with dry hydrogen chloride in 1,4-dioxane (4N, 1 mL) and was concentrated after 3 hours to give the deprotected material. Purification was by preparative reverse phase HPLC. The compound (0.058 g) was subsequently dissolved in dichloromethane and treated with dry hydrogen chloride in 1,4-dioxane (4N, 0.4 mL) and was concentrated after 10 minutes to give the desired compound as a white solid (0.062 g).

$^1$H NMR (400 MHz, CD$_3$OD) δ 8.73 (1H, s); 8.66 (1H, t); 7.55 (1H, s); 4.54 (2H, s); 3.58–3.55 (2H, m); 3.50–3.47 (2H, m); 3.08 (2H, d); 2.81 (3H, s); 1.99 (3H, s); 1.74 (6H, q); 1.63 (6H, s). MS: APCI(+ve) 391, 393 (M+1). MP: 259–262° C.

EXAMPLE 32

N-(1-Adamantylmethyl)-5-chloro-2-{3-[(2-hydroxyethyl)amino]ethyl}isonicotinamide dihydrochloride

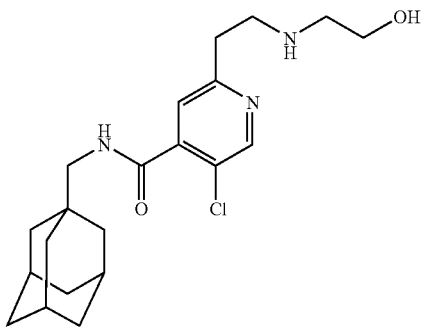

N-(1-Adamantylmethyl)-5-chloro-2-vinylisonicotinamide (0.37 mmolar, 125 mg) (Example 29(i) was dissolved in a mixture of methanol (1 mL), isopropanol (1 mL) and acetic acid (1 mL). The resulting solution was treated with 2-aminoethanol (1 mL) and heated to 100° C. for 18 h The solution was allowed to cool to room temperature, poured into saturated sodium bicarbonate solution (20 mL) and extracted with dichloromethane (2×20 mL). The combined organic extracts were dried over anhydrous magnesium sulfate, filtered and concentrated. The residue was purified by chromatography on silica gel eluting with methanol:dichloromethane:ammonia (10:30:0.1). The isolated material was dissolved in a solution of hydrogen chloride in 1,4-dioxane (1 mL of a 4M solution) and concentrated to afford the titled compound as a colorless powder (0.027 g).

$^1$H NMR (400 MHz, DMSO-d$_6$) δ 8.95 (2H, m); 8.62 (1H, s); 8.55 (1H, t); 7.41 (1H, s); 3.68 (2H, t); 3.32 (2H, m); 3.20 (2H, m); 3.04 (2H, m); 2.95 (2H, d); 1.95 (3H, m); 1.71–1.57 (6H, m); 1.53 (6H, m). MS: APCI(+ve) 392, 394 (M+1). MP: 242–244° C.

EXAMPLE 33

N-(1-Adamantylmethyl)-5-chloro-2-{3-[(3-hydroxypropyl)amino]ethyl}isonicotinamide dihydrochloride

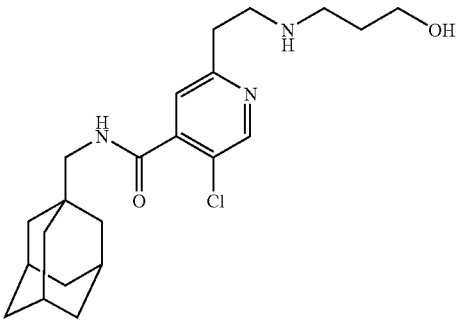

N-(1-Adamantylmethyl)-5-chloro-2-vinylisonicotinamide (0.37 mmolar, 125 mg) (Example 29(i)) was dissolved in a mixture of methanol (1 mL), isopropanol (1 mL) and acetic acid (1 mL). The resulting solution was treated with 3-aminopropanol (1 mL) and heated to 100° C. for 18 h. The solution was allowed to cool to room temperature, poured into saturated sodium bicarbonate solution (20 mL) and extracted with dichloromethane (2×20 mL). The combined organic extracts were dried over anhydrous magnesium sulfate, filtered and concentrated. The residue was purified by chromatography on silica gel eluting with methanol:dichloromethane:ammonia (10:30:0.1). The isolated material was dissolved in a solution of hydrogen chloride in 1,4-dioxane (1 mL of a 4M solution) and concentrated to afford the titled compound as a colorless powder (0.025 g).

$^1$H NMR (400 MHz, DMSO-d$_6$) δ 8.82 (2H, m); 8.62 (1H, s); 8.54 (1H, t); 7.43 (1H, s); 3.50 (2H, t); 3.30 (2H, m); 3.17 (2H, m); 3.02 (2H, m); 2.95 (2H, d); 1.95 (3H, m); 1.78 (2H, quintet); 1.71–1.57 (6H, m); 1.53 (6H, m). MS: APCI(+ve) 406, 408 (M+1). MP: 240–242° C.

EXAMPLE 34

N-(1-Adamantylmethyl)-5-chloro2-[3-(methylamino)propyl]isonicotinamide hydrochloride

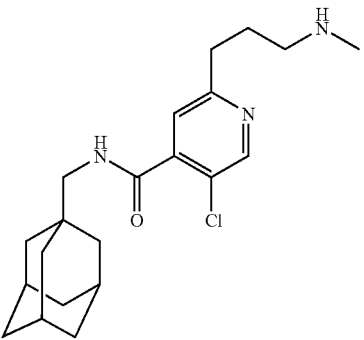

A solution of tert-butyl allyl(methyl)carbamate (0.27 g) in 9-boroabicyclo[3.3.1]nonane (6.24 ml of a 0.5M solution in tetrahydrofuran) was heated at reflux under nitrogen for 4 hours. The solution was cooled to 0° C. and potassium phosphate (1.5 ml of a 3M solution in water) was added. The mixture was stirred for 15 minutes and a solution of N-(1-adamantylmethyl)-2-bromo-5-chloroisonicotinamide (Example 1(ii)) (0.50 g) and dichloro[1,1'-bis(diphenylphosphino)ferrocenyl]palladium (II) (0.045 g) in anhydrous N,N-dimethylformamide (4 ml) was added. The mixture was heated at 60° C. under nitrogen for 3 hours, diluted with saturated brine (25 ml) and extracted into ethyl acetate (3×25 ml). The combined extracts were dried over anhydrous sodium sulphate, filtered and concentrated. The residue was purified by chromatography on silica gel eluting with isohexane:ethyl acetate (6:1 to 1.5:1). The isolated material (0.50 g) was dissolved in a solution of hydrogen chloride in 1,4-dioxane (10 ml of a 4M solution) and concentrated; the resultant solid was recrystallised from 1,4-dioxane/methanol and the solid collected by is filtration to afford the titled compound (0.19 g) as a colourless powder.

$^1$H NMR (400 MHz, DMSO-$d_6$) δ 8.84 (2H, broad); 8.60 (1H, s); 8.53 (1H, t); 7.35 (1H, s); 2.95–2.82 (6H, m); 2.02 (2H, q); 1.95 (3H, s); 1.64 (6H, q); 1.52 (6H, s). MS: APCI(+ve) 378/376 (M+1) MP: 210–212° C.

EXAMPLE 35

N-(1-Adamantylmethyl)-5-bromo-2-{[(2S)-2-hydroxy-3-(methylamino)propyl]oxy}isonicotinamide

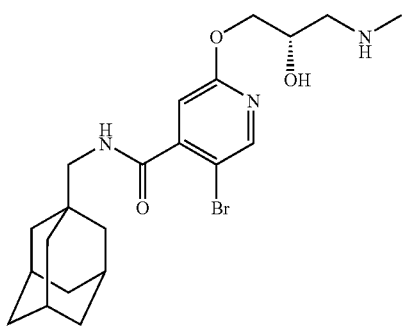

(i) N-(1-Adamantylmethyl)-5-bromo-2-methoxyisonicotinamide n-Butyllithium (2.51 ml of a 2.5M solution in hexanes) was added to diisopropylamine (0.88 ml) in dry tetrahydrofuran,(15 ml) at 65° C. To this solution was added a solution of 5-bromo-2-methoxypyridine (0.82 ml) in dry tetrahydrofuran (10 ml) dropwise over 30 minutes at –65° C. A solution of 1-adamantylmethylisocyanate (1 g) in dry tetrahydrofuran (10 ml) was then added in small portions over 30 minutes at –65° C. The reaction mixture was allowed to warm to 0° C., diluted with saturated brine (20 ml) and extracted into ethyl acetate (3×20 ml). The combined extracts were dried over anhydrous sodium sulphate, filtered and concentrated. The residue was purified by chromatography on silica gel eluting with dichloromethane:acetone (19:1 to 2.5:1) to afford the sub-titled compound (1.1 g) as a colourless powder.
MS: APCI(+ve) 381/379 (M+1)

(ii) N-(1-Adamantylmethyl)-5-bromo-2-hydroxyisonicotinamide

Sodium iodide (0.48 g) was added to a solution of trimethylsilylchloride (0.41 ml) in acetonitrile (30 ml) and the mixture was stirred for 1 hour. N-(1-Adamantylmethyl)-5-bromo-2-methoxyisonicotinamide (0.94 g) (Example 35(i)) was then added and the reaction mixture was heated at 60° C. under nitrogen for 3 hours. The reaction mixture was diluted with water (150 ml) and the resultant solid was collected by filtration and dried by means of ethanol/toluene azeotrope. The solid was triturated with diethyl ether and collected by filtration to afford the sub-titled compound (0.70 g).

(iii) N-(1-Adamantylmethyl)-5-bromo-2-[(2S)-oxiran-2-ylmethoxy]isonicotinamide

A suspension of (S)-glycidyl nosylate (0.29 g), caesium carbonate (1.82 g) and N-(1-adamantylmethyl)-5-bromo-2hydroxyisonicotinamide (0.41 g) (Example 35(ii)) in anhydrous N,N-dimethylformamide (6 ml) was heated at 60° C. under nitrogen for 2 hours. The reaction mixture was allowed to cool to room temperature, diluted with water (50 ml) and extracted into ethyl acetate (3×20 ml). The combined extracts were dried over anhydrous sodium sulphate, filtered and concentrated. The residue was purified by chromatography on silica gel eluting with dichloromethane:ethyl acetate (4:1 to 0:1) to afford the sub-titled compound (0.12 g).

MS: APCI(+ve) 423/421 (M+1)

(iv) N-(1-Adamantylmethyl)-5-bromo-2-{[(2S)-2-hydroxy-3-(methylamino)propyl]oxy}isonicotinamide A mixture of N-(1-adamantylmethyl)-5-bromo-2-[(2S)-oxiran-2-ylmethoxy]isonicotinamide (0.12 g) (Example 35(iii)), 40% aqueous methylamine (4 ml) and 1,4-dioxane (4 ml) was stirred for 4 hours. The reaction mixture was concentrated and the residue was purified by chromatography on silica gel eluting with ethyl acetate:ethanol:0.880 ammonia solution (4:1:0.1 to 1.5:1:0.1). The isolated material was dissolved in a solution of hydrogen chloride in 1,4-dioxane (10 ml of a 4M solution) and concentrated to afford the titled compound (0.039 g).

$^1$H NMR (400 MHz, DMSO-$d_6$) δ 8.80 (1H, broad); 8.60 (1H, broad); 8.49 (1H, t): 8.36 (1H,s); 6.83 (1H, s); 5.87 (1H,d); 4.3–4.1 (3H, m); 2.92 (2H, d); 2.57 (3H, broad triplet); 1.94 (3H, s); 1.64 (6H, q); 1.52 (6H, s). MS: APCI(+ve) 454/452 (M+1)

EXAMPLE 36

N-(1-Adamantylmethyl)-2-({3-[bis(3-hydroxypropyl)amino]propyl}amino)-3-chloroisonicotinamide dihydrochloride

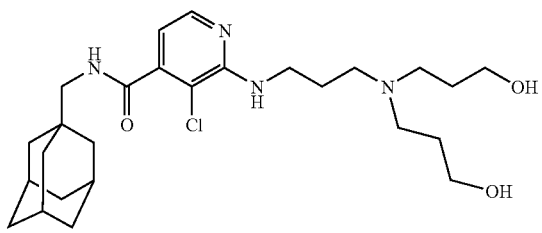

(i) tert-Butyl 3-[(4-{[(1-adamantylmethyl)amino]carbonyl}-3-chloropyridin-2-yl)amino]propylcarbamate N-(1-Adamantylmethyl)-2,3-dichloroisonicotinamide (0.4 g) and tert-butyl 3-aminopropylcarbamate (0.4 g) in DMSO (4 ml) were heated in a sealed tube at 160 C for 5 hrs. Ethyl acetate was added and the solution was washed with NaHCO$_3$ solution, water, KHSO$_4$ solution and water. The solution was dried and the solvent was evaporated. The resulting oil was subjected to flash chromatography, using ethyl acetate/hexane as eluant, to give the title compound as a colourless oil (0.41 g).
MS (ES+) 477, 479

(ii) N-(1-Adamantylmethyl)-2-[(3-aminopropyl)amino]-3-chloroisonicotinamide dihydrochloride tert-Butyl 3-[(4-{[(1-adamantylmethyl)amino]carbonyl}-3-chloropyridin-2-yl)amino]propylcarbamate (0.41 g) Example 36(i)) in methanol (15 ml) was treated with a solution of HCl in 1,4-dioxane (4 ml) and the mixture was stirred at room temperature for 18 hrs. The solution was evaporated. Methanol was added and the solution was evaporated to give the title compound as a pale yellow solid.
MS (ES+) 377, 379

(iii) N-(1-Adamantylmethyl)-2-({3-[bis(3-{[tert-butyl(dimethyl)silyl]oxy}propyl)amino]propyl}amino)-3-chloroisonicotinamide To N-(1-adamantylmethyl)-2-[(3-aminopropyl)amino]-3-chloroisonicotinamide (0.32 g) (Example 36(ii)) and 3-{[tert-butyl(dimethyl)silyl]oxy}propanal (0.16 g) in dichloromethane (15 ml) was added sodium triacetoxyborohydride (0.18 g). The mixture was stirred for 18 hrs at room temperature. NaHCO$_3$ solution was added and the product was extracted into dichloromethane. The solution was dried and the solvent was evaporated. Flash chromatography, using NH$_3$/MeOH/CH$_2$Cl$_2$ as eluant, gave the title compound as a colourless oil.

(iv) N-(1-Adamantylmethyl)-2-({3-[bis(3-hydroxypropyl)amino]propyl}amino)-3-chloroisonicotinamide dihydrochloride N-(1-adamantylmethyl)-2-({3-[bis(3-{[tert-butyl(dimethyl)silyl]oxy}propyl)amino]-propyl}amino)3-chloroisonicotinamide (Example 36(iii)) in methanol (5 ml) was treated with HCl in 1,4-dioxane (3 ml). The mixture was stirred at room temperature for 3 hrs. The solvent was evaporated. The product was purified by reverse phase HPLC, using NH$_3$/H$_2$O/CH$_3$CN as eluant. The resulting oil in methanol was treated with ethereal HCl and the solvent was evaporated to yield the title compound as a white solid (0.14 g).
$^1$H NMR (400 MHz, DMSO-d$_6$) δ 8.68 (1H, t), 8.10 (1H, d), 6.86 (1H, d), 3.65–3.74 (6H, m), 3.30–3.36 (6H, m), 3.075 (2H, d), 2.12–2.22 (2H, m), 1.93–2.02 (7H, m), 1.77 (3H, d), 1.69 (3H, d), 1.62 (6H, s). MS (APCI+) 493, 495 [M+H]$^+$ Pharmacological Analysis Certain compounds such as benzoylbenzoyl adenosine triphosphate (bbATP) are known to be agonists of the P2X$_7$ receptor, effecting the formation of pores in the plasma membrane (Drug Development Research (1996), 37(3) p. 126). Consequently, when the receptor is activated using bbATP in the presence of ethidium bromide (a fluorescent DNA probe), an increase in the fluorescence of intracellular DNA-bound ethidium bromide is observed. The increase in fluorescence can be used as a measure of P2X$_7$ receptor activation and therefore to quantify the effect of a compound on the P2X$_7$ receptor.

In this manner, each of the title compounds of the Examples was tested for antagonist activity at the P2X$_7$ receptor. Thus, the test was performed in 96-well flat bottomed microtitre plates, the wells being filled with 250 µl of test solution comprising 200 µl of a suspension of THP-1 cells (2.5×10$_6$ cells/ml) containing 10$^{-4}$M ethidium bromide, 25 µl of a high potassium buffer solution containing 10$^{-5}$M bbATP, and 25 µl of the high potassium buffer solution containing 3×10$^{-5}$M test compound. The plate was covered with a plastics sheet and incubated at 37° C. for one hour. The plate was then read in a Perkin-Elmer fluorescent plate reader, excitation 520 nm, emission 595 nm, slit widths: Ex 15 nm, Em 20 nm. For the purposes of comparison, bbATP (a P2X$_7$ receptor agonist) and pyridoxal 5-phosphate (a P2X$_7$ receptor antagonist) were used separately in the test as controls. From the readings obtained, a pIC$_{50}$ figure was calculated for each test compound, this figure being the negative logarithm of the concentration of test compound necessary to reduce the bbATP agonist activity by 50%. Each of the compounds of the Examples demonstrated antagonist activity, having a pIC$_{50}$ figure>4.50. For example, the compounds of Example 12 and Example 26 had pIC$_{50}$ values of 7.1 and 7.8 respectively.

The invention claimed is:

1. A compound of formula

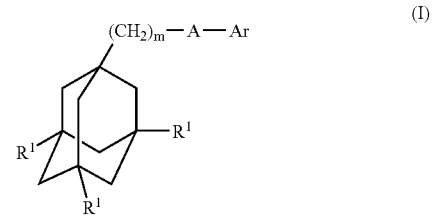

(I)

wherein m represents 1, 2 or 3;
each R$^1$ independently represents a hydrogen or halogen atom;
A represents C(O)NH or NHC(O);
Ar represents a group

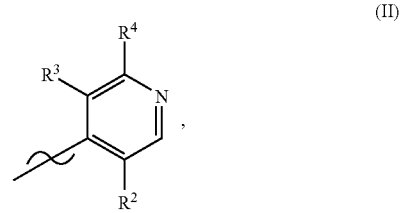

(II)

-continued

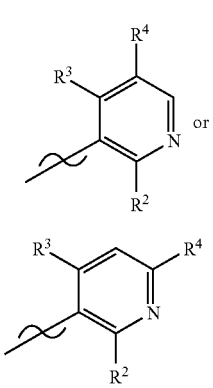

one of R² and R³ represents halogen, nitro, amino, hydroxyl, or a group selected from (i) C₁–C₆ alkyl optionally substituted by at least one halogen atom, (ii) C₃–C₈ cycloalkyl, (iii) C₁–C₆ alkoxy optionally substituted by at least one halogen atom, and (iv) C₃–C₈ cycloalkyloxy, and the other of R² and R³ represents a hydrogen or halogen atom;

R⁴ represents a group

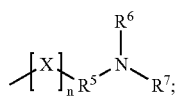

X represents an oxygen or sulphur atom or a group >N—R⁸;

n is 0 or 1;

R⁵ represents a C₁–C₅ alkyl group which may be optionally substituted by at least one substituent selected from hydroxyl, halogen and C₁–C₆ alkoxy;

R⁶ and R⁷ each independently represent a hydrogen atom, C₁–C₆ alkyl (optionally substituted by at least one substituent selected from hydroxyl, halogen, C₁–C₆ alkoxy, and (di)-C₁–C₄ alkylamino (itself optionally substituted by at least one hydroxyl group)), or C₃–C₈ cycloalkyl (optionally substituted by at least one substituent selected from hydroxyl, halogen and C₁–C₆ alkoxy); and R⁸ represents a hydrogen atom or a C₁–C₅ alkyl group which may be optionally substituted by at least one substituent selected from hydroxyl, halogen and C₁–C₆ alkoxy; with the provisos that:

(a) when n is 0, then A is NHC(O), and (b) when n is 1, X represents oxygen and A is C(O)NH, then R⁶ and R⁷ do not both simultaneously represent a hydrogen atom or do not both simultaneously represent an unsubstituted C₁–C₆ alkyl, or when one of R⁶ and R⁷ represents a hydrogen atom, then the other of R⁶ and R⁷ does not represent an unsubstituted C₁–C₆ alkyl; and (c) when n is 1, X is oxygen, sulphur or NH and A is NHC(O), then R⁶ and R⁷ do not both simultaneously represent a hydrogen atom or do not both simultaneously represent an unsubstituted C₁–C₆ alkyl, or when one of R⁶ and R⁷ represents a hydrogen atom, then the other of R⁶ and R⁷ does not represent an unsubstituted C₁–C₆ alkyl or —CH₂CH₂OH;

or a pharmaceutically acceptable salt or solvate thereof.

2. A compound of formula (I) according to claim 1, wherein m represents 1, 2 or 3;

each R¹ independently represents a hydrogen or halogen atom;

A represents C(O)NH or NHC(O);

Ar represents a group

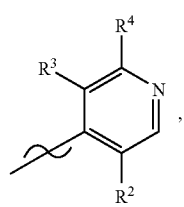

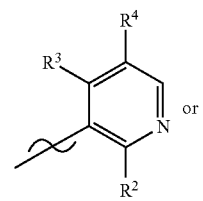

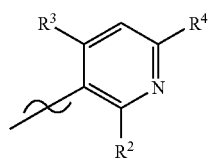

one of R² and R³ represents halogen, nitro, amino, hydroxyl, or a group selected from (i) C₁–C₆ alkyl optionally substituted by at least one halogen atom, (ii) C₃–C₈ cycloalkyl, (iii) C₁–C₆ alkoxy optionally substituted by at least one halogen atom, and (iv) C₃–C₈ cycloalkyloxy, and the other of R² and R³ represents a hydrogen or halogen atom;

R⁴ represents a group

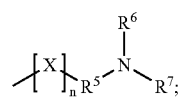

X represents an oxygen or sulphur atom or a group >N—R⁸;

n is 0 or 1;

R⁵ represents a C₁–C₅ alkyl group which may be optionally substituted by at least one substituent selected from hydroxyl, halogen and C₁–C₆ alkoxy; and R⁶, R⁷ and R⁸ each independently represent a hydrogen atom or a C₁–C₅ alkyl group which may be optionally substituted by at least one substituent selected from hydroxyl, halogen and C₁–C₆ alkoxy;

with the provisos that:

(d) when n is 0, then A is NHC(O), and (e) when n is 1, X represents oxygen and A is C(O)NH, then R⁶ and R⁷ do not both simultaneously represent a hydrogen atom or do not both simultaneously represent an unsubstituted C₁–C₅ alkyl, or when one of $R^6$ and $R^7$ represents a hydrogen atom, then the other of $R^6$ and $R^7$ does not represent an unsubstituted $C_1$–$C_5$ alkyl, and (f) when n is 1, X is oxygen, sulphur or NH and A is NHC(O), then $R^6$ and $R^7$ do not both simultaneously represent a hydrogen atom or do not both simultaneously represent an unsubstituted $C_1$–$C_5$ alkyl, or when one of $R^6$ and $R^7$ represents a hydrogen atom, then the other of $R^6$ and $R^7$ does not represent an unsubstituted $C_1$–$C_5$ alkyl or —$CH_2CH_2OH$;

or a pharmaceutically acceptable salt or solvate thereof.

3. A compound according to claim 1, wherein m is 1.

4. A compound according to claim 1, wherein A represents NHC(O).

5. A compound according to claim 1, wherein Ar represents a group of formula (II) or (III).

6. A compound according to claim 5, wherein Ar represents a group of formula (II).

7. A compound according to claim 1, wherein one of $R^2$ and $R^3$ represents a halogen atom and the other of $R^2$ and $R^3$ represents a hydrogen atom.

8. A compound according to claim 1, wherein n is 0.

9. A compound according to claim 1, wherein
m represents 1;
each $R^1$ represents a hydrogen atom;
A represents NHC(O);
Ar represents a group

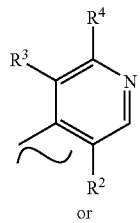

(II)

or

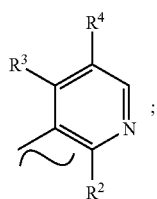

(III)

one of $R^2$ and $R^3$ represents a halogen atom, and the other of $R^2$ and $R^3$ represents a hydrogen atom;
$R^4$ represents a group

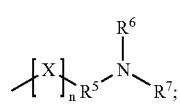

(V)

X represents an oxygen or sulphur atom or a group >N—$R^8$;
n is 0 or 1;
$R^5$ represents a $C_1$–$C_3$ alkyl group optionally substituted by at least one hydroxyl group;
$R^6$ and $R^7$ each independently represent a hydrogen atom, $C_1$–$C_5$ alkyl (optionally substituted by one or two substituents independently selected from hydroxyl and (di)-$C_1$–$C_2$ alkylamino (itself optionally substituted by at least one hydroxyl group)), or $C_6$ cycloalkyl (substituted by at least one hydroxyl group);
$R^8$ represents a hydrogen atom or a $C_2$ alkyl group substituted by at least one hydroxyl group.

10. A compound according to claim 1, wherein
m represents 1;
each $R^1$ represents a hydrogen atom;
A represents NHC(O);
Ar represents a group

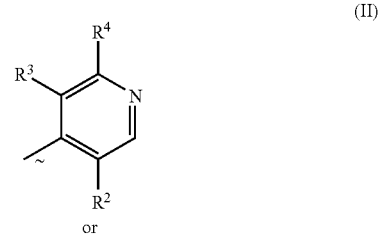

(II)

or

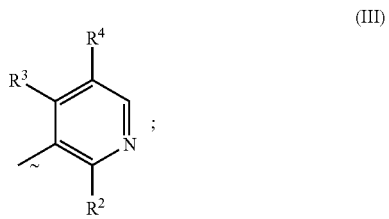

(III)

one of $R^2$ and $R^3$ represents a halogen atom, and the other of $R^2$ and $R^3$ represents a hydrogen atom;
$R^4$ represents a group

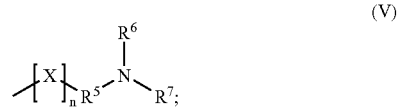

(V)

X represents an oxygen or sulphur atom or a group >N—$R^8$;
n is 0 or 1;
$R^5$ represents a $C_2$–$C_3$ alkyl group optionally substituted by at least one hydroxyl group;
$R^6$ and $R^7$ each independently represent a hydrogen atom or a $C_1$–$C_5$ alkyl group optionally substituted by one or two hydroxyl groups;
$R^8$ represents a hydrogen atom or a $C_2$ alkyl group substituted by at least one hydroxyl group.

11. A compound being selected from any one of:
N-(1-Adamantylmethyl)-5-chloro-2-{3-[(3-hydroxypropyl)-amino]propyl}isonicotinamide,
N-(1-Adamantylmethyl)-5-chloro-2-{3-[(3-hydroxypropyl)amino]propyl}-isonicotinamide dihydrochloride,
N-(1-Adamantylmethyl)-2-chloro-5-{3-[(3-hydroxypropyl)amino]propyl}nicotinamide,
N-(1-Adamantylmethyl)-2-chloro-5-(3-{[(1S)-2-hydroxy-1-methylethyl]amino}propyl)nicotinamide,
N-(1-Adamantylmethyl)-2-chloro-5-(3-{[(1R)-2-hydroxy-1-methylethyl]amino}propyl)nicotinamide,
N-(1-Adamantylmethyl)-2-(3-aminopropyl)-5-chloroisonicotinamide hydrochloride,
N-(1-Adamantylmethyl)-5-chloro-2-[3-(ethylamino)propyl]isonicotinamide hydrochloride, N-(1-Adamantylmethyl)-5-chloro-2-({2-[(3-hydroxypropyl)amino]-ethyl}thio)isonicotinamide hydrochloride,
N-(1-Adamantylmethyl)-5-chloro-2-(3-{[(1R)-2-hydroxy-1-methylethyl]amino}propyl)isonicotinamide, dihydrochloride,
N-(1-Adamantylmethyl)-5-chloro-2-(3-{[(1S)-2-hydroxy-1-methylethyl]amino}propyl)isonicotinamide, dihydrochloride,
N-(1-Adamantylmethyl)-5-chloro-2-{3-[(2-hydroxyethyl)amino]propyl}isonicotinamide hydrochloride,
N-(1-Adamantylmethyl)-5-chloro-2-{2-[(3-hydroxypropyl)amino]ethoxy}isonicotinamide, hydrochloride
N-(1-Adamantylmethyl)-5-chloro-2-({2-[(2-hydroxyethyl)amino]ethyl}-amino)isonicotinamide dihydrochloride,
N-(1-Adamantylmethyl)-5-chloro-2-[3-(isopropylamino)propyl]isonicotinamide dihydrochloride,
N-(1-Adamantylmethyl)-5-chloro-2-(3-{[(2S)-2-hydroxypropyl]amino}propyl)isonicotinamide, dihydrochloride,
N-(1-Adamantylmethyl)-5-chloro-2-(3-{[(2R)-2,3-dihydroxypropyl]amino}propyl)isonicotinamide, dihydrochloride,
N-(1-Adamantylmethyl)-5-chloro-2-(3-{[(2S)-2,3-dihydroxypropyl]amino}propyl)isonicotinamide, dihydrochloride,
N-(1-Adamantylmethyl)-5-chloro-2-{3-[(4-methylcyclohexyl)amino]propyl}isonicotinamide dihydrochloride,
N-(1-Adamantylmethyl)-5-chloro-2-{3-[(2-hydroxy-2-methylpropyl)amino]propyl}isonicotinamide dihydrochloride,
N-(1-Adamantylmethyl)-5-chloro-2-(3-{[(1R)-1-(hydroxymethyl)-2-methylpropyl]amino}propyl)isonicotinamide, dihydrochloride,
N-(1-Adamantylmethyl)-5-chloro-2-(3-{[2-(methylamino)ethyl]amino}propyl)isonicotinamide dihydrochloride,
N-(1-Adamantylmethyl)-5-chloro-2-(3-{[3-(methylamino)propyl]amino}propyl)isonicotinamide bis(trifluoroacetate),
N-(1-Adamantylmethyl)-5-chloro-2-[3-({2-[(2-hydroxyethyl)amino]ethyl}amino)propyl]isonicotinamide dihydrochloride,
N-(1-Adamantylmethyl)-5-chloro-2-(3-{[2-(diethylamino)ethyl]amino}propyl)isonicotinamide dihydrochloride,
N-(1-Adamantylmethyl)-5-chloro-2-(3-{[2-hydroxy-1-(hydroxymethyl)ethyl]amino}propyl)isonicotinamide dihydrochloride,
N-(1-Adamantylmethyl)-5-chloro-2-{3-[(2-hydroxyethyl)(methyl)amino]propyl}isonicotinamide dihydrochloride,
N-(1-Adamantylmethyl)-5-chloro-2-{3-[(3-hydroxy-2,2-dimethylpropyl)amino]propyl}isonicotinamide dihydrochloride,
N-(1-Adamantylmethyl)-5-chloro-2-(3-{[(2R)-2-hydroxypropyl]amino}propyl)isonicotinamide, dihydrochloride,
N-(1-Adamantylmethyl)-5-chloro-2-({[3-(methylamino)propyl]amino}methyl)isonicotinamide dihydrochloride,
N-(1-Adamantylmethyl)-5-chloro-2-[({2-[(2-hydroxyethyl)amino]ethyl}amino)methyl]isonicotinamide dihydrochloride,
N-(1-Adamantylmethyl)-5-chloro-2-({[2-(methylamino)ethyl]amino}methyl)isonicotinamide dihydrochloride,
N-(1-Adamantylmethyl)-5-chloro-2-{3-[(2-hydroxyethyl)amino]ethyl}isonicotinamide dihydrochloride,
N-(1-Adamantylmethyl)-5-chloro-2-{3-[(3-hydroxypropyl)amino]ethyl}isonicotinamide dihydrochloride,
N-(1-Adamantylmethyl)-5-chloro-2-[3-(methylamino)propyl]isonicotinamide hydrochloride,
N-(1-Adamantylmethyl)-5-bromo-2-{[(2S)-2-hydroxy-3-(methylamino)propyl]oxy}isonicotinamide, and
N-(1-Adamantylmethyl)-2-({3-[bis(3-hydroxypropyl)amino]propyl}amino)-3-chloroisonicotinamide dihydrochloride, or pharmaceutically acceptable salts and solvates thereof.

12. A process for the preparation of a compound according to claim 1, which comprises:

(i) when n is 0 and $R^5$ represents $CH_2$, reacting a compound of formula

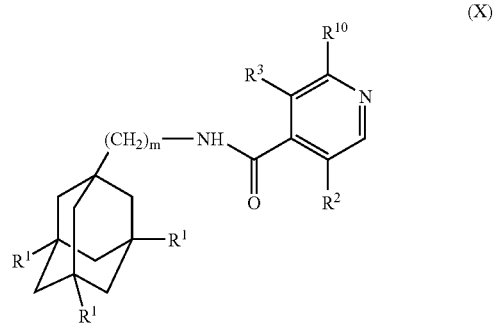

(X)

wherein $R^{10}$ represents —C(O)H or —$CH_2L^1$, $L^1$ represents a leaving group and m, $R^1$, $R^2$ and $R^3$ are as defined in formula (I), or a compound of formula

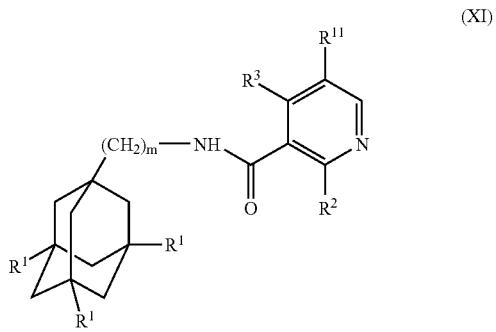

(XI)

wherein $R^{11}$ represents —C(O)H or —$CH_2L^2$, $L^2$ represents a leaving group and m, $R^1$, $R^2$ and $R^3$ are as defined in formula (I), or a compound of formula

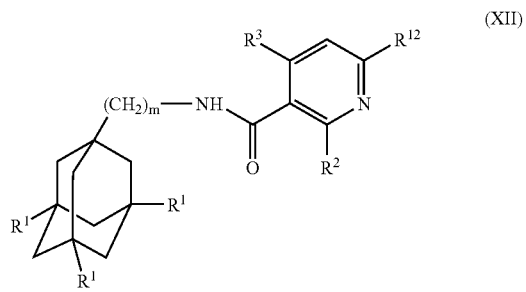

(XII)

wherein $R^{12}$ represents —C(O)H or —CH$_2$L$^3$, L$^3$ represents a leaving group and m, $R^1$, $R^2$ and $R^3$ are as defined in formula (I), with a compound of formula (XIII), HNR$^6$R$^7$, wherein $R^6$ and $R^7$ are as defined in formula (I), under reductive amination conditions when $R^{10}$, $R^{11}$ or $R^{12}$ represents —C(O)H or in the presence of a suitable base when $R^{10}$, $R^{11}$ or $R^{12}$ represents —CH$_2$L$^1$, —CH$_2$L$^2$ or —CH$_2$L$^3$; or (ii) when n is 0, $R^5$ is (CH$_2$)$_2$ and $R^6$ and $R^7$ are both hydrogen, reacting a compound of formula (X) as defined in (i) above in which $R^{10}$ represents —CH$_2$L$^1$, or a compound of formula (XI) as defined in (i) above in which $R^{11}$ represents —CH$_2$L$^2$, or a compound of formula (XII) as defined in (i) above in which $R^{12}$ represents —CH$_2$L$^3$, with an alkali metal cyanide, followed by a hydrogenation reaction; or (iii) when n is 0, $R^5$ is (CH$_2$)$_2$ and at least one of $R^6$ and $R^7$ is other than hydrogen, reacting a compound as prepared in (ii) above with at least one compound of formula (XIV), R$^{13}$C(O)H, wherein $R^{13}$ represents an optionally substituted C$_1$–C$_6$ alkyl or C$_3$–C$_8$ cycloalkyl group as defined for $R^6$ and $R^7$ in formula (I), under reductive amination conditions; or (iv) when n is 0 and $R^5$ represents a C$_3$–C$_5$ alkyl group optionally substituted as in formula (I), reacting a compound of formula

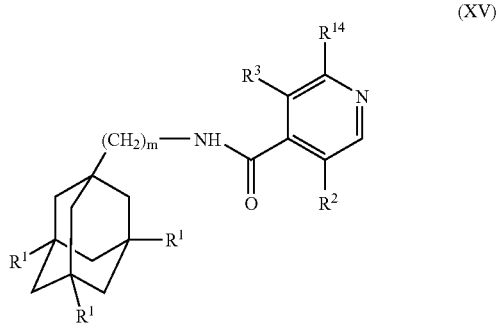

(XV)

wherein $R^{14}$ represents a leaving group and m, $R^1$, $R^2$ and $R^3$ are as defined in formula (I), or a compound of formula

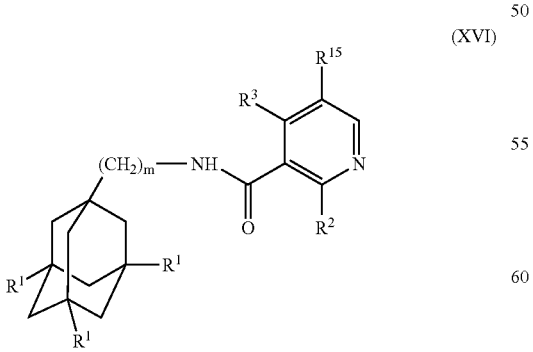

(XVI)

wherein $R^{15}$ represents a leaving group and m, A, $R^1$, $R^2$ and $R^3$ are as defined in formula (I), or a compound of formula

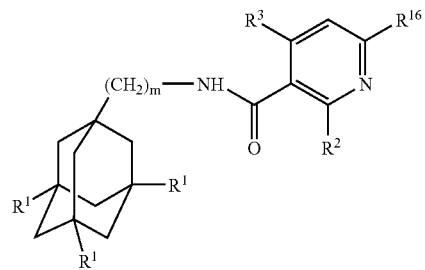

(XVII)

wherein $R^{16}$ represents a leaving group and m, $R^1$, $R^2$ and $R^3$ are as defined in formula (I), with a compound of formula

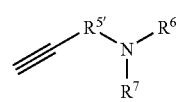

(XVIII)

wherein $R^{5'}$ represents a C$_1$–C$_3$ alkyl group optionally substituted as defined for $R^5$ in formula (I) and $R^6$ and $R^7$ are as defined in formula (I), followed by a hydrogenation reaction; or (v) when n is 0 and $R^5$ represents a C$_3$–C$_5$ alkyl group optionally substituted as defined in formula (I), reacting a compound of formula (XV), (XVI) or (XVII) as defined in (iv) above, with a compound of formula

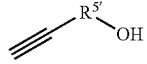

(XIX)

wherein $R^{5'}$ is as defined in formula (XVIII) in (iv) above, followed by a hydrogenation reaction and then an oxidation reaction and then by reaction with a compound of formula (XIII) as defined in (i) above under reductive amination conditions; or (vi) when n is 1 and X is oxygen or >N—R$^8$, reacting a compound of formula

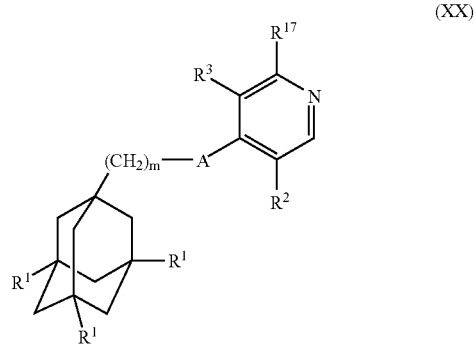

(XX)

wherein $R^{17}$ represents a leaving group and m, A, $R^1$, $R^2$ and $R^3$ are as defined in formula (I), or a compound of formula

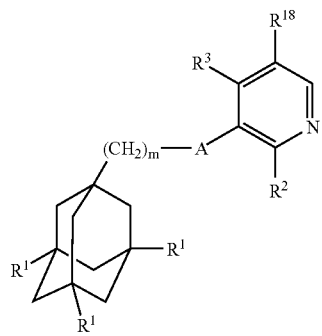
(XXI)

wherein $R^{18}$ represents a leaving group and m, A, $R^1$, $R^2$ and $R^3$ are as defined in formula (I), or a compound of formula

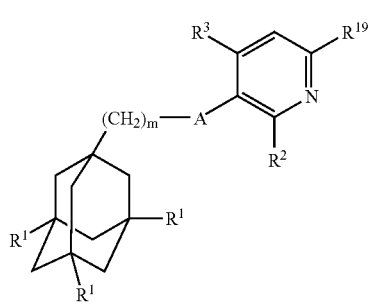
(XXII)

wherein $R^{19}$ represents a leaving group and m, A, $R^1$, $R^2$ and $R^3$ are as defined in formula (I), with a compound of formula

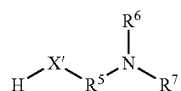
(XXIII)

wherein X' represents oxygen or >N—$R^8$ and $R^5$, $R^6$, $R^7$ and $R^8$ are as defined in formula (I); or (vii) when A is NHC(O), n is 1 and X is sulphur, reacting a compound of formula

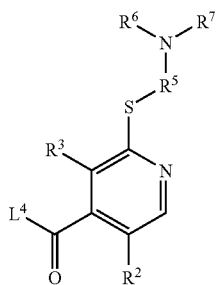
(XXIV)

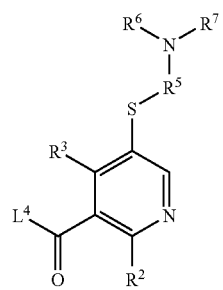
(XXV)

or

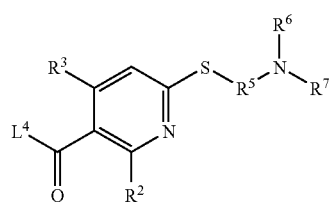
(XXVI)

wherein, in each of formulae (XXIV), (XXV) and (XXVI), $L^4$ represents a leaving group and $R^2$, $R^3$, $R^5$, $R^6$ and $R^7$ are as defined in formula (I), with a compound of formula

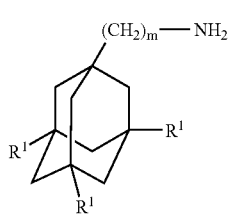
(XXVII)

wherein m and $R^1$ are as defined in formula (I); or (viii) when A is C(O)NH, n is 1 and X is sulphur, reacting a compound of formula

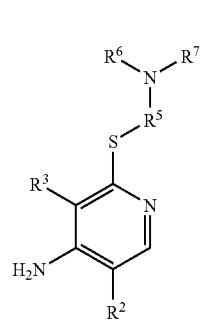
(XXVIII)

-continued

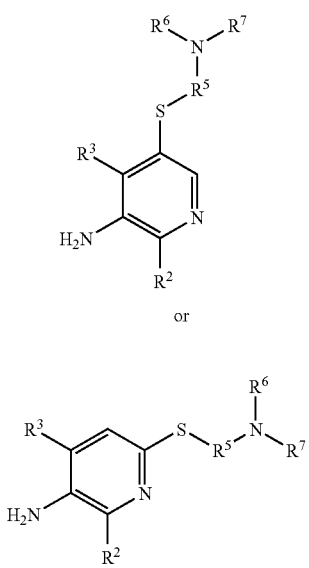
(XXIX)

or (XXX)

wherein, in each of formulae (XXVIII), (XXIX) and (XXX), $R^2$, $R^3$, $R^5$, $R^6$ and $R^7$ are as defined in formula (I), with a compound of formula

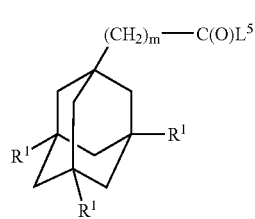
(XXXI)

wherein $L^5$ represents a leaving group and m and $R^1$ are as defined in formula (I); or (ix) when n is 0 and $R^5$ represents a $C_2$–$C_5$ alkyl group substituted as defined in formula (I), reacting a compound of formula

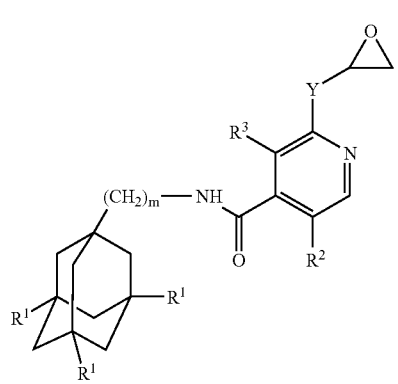
(XXXII)

or a compound of formula

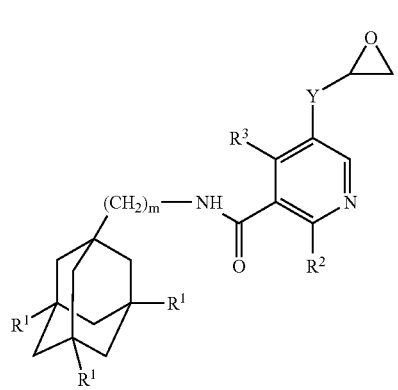
(XXXIII)

or a compound of formula

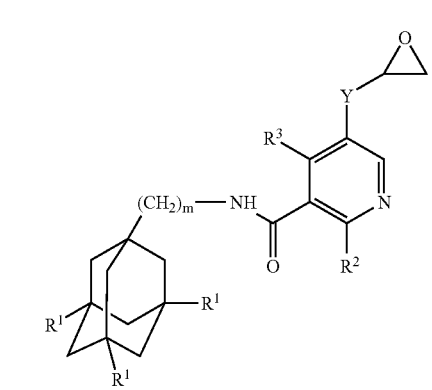
(XXXIV)

wherein, in each of formulae (XXXII), (XXXIII) and (XXXIV), Y represents a bond or a $C_1$–$C_3$ alkyl and m, $R^1$, $R^2$ and $R^3$ are as defined in formula (I), with a compound of formula (XIII) as defined in (i) above, and optionally thereafter reacting with a $C_1$–$C_6$ alkylating agent or with a halogenating agent; or (x) when n is 0 and $R^5$ represents a $C_3$–$C_5$ alkyl group optionally substituted as defined in formula (I), reacting a compound of formula (XV), (XVI) or (XVII) as defined in (iv) above, with a pre-treated compound of formula

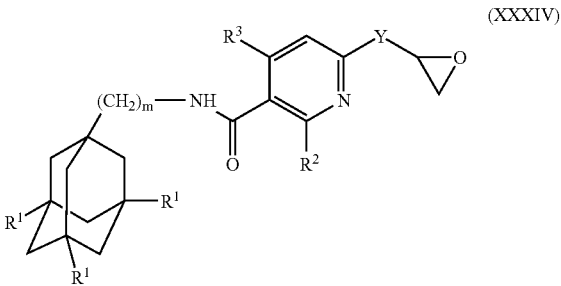
(XXXV)

in which $L^6$ represents a hydrogen atom and $R^{5'}$ represents a $C_1$–$C_3$ alkyl group optionally substituted as defined for $R^5$ in formula (I) and $R^6$ and $R^7$ are as defined in formula (I), wherein the compound of formula (XXXV) is pre-treated with a hydroborating agent; or (xi) when n is 0 and $R^5$ represents a $C_3$–$C_5$ alkyl group optionally substituted as defined in formula (I), reacting a compound of formula (XV), (XVI) or (XVII) as defined in (iv) above in the presence of a suitable catalyst, with a pre-treated compound of formula

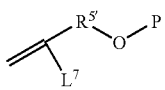

(XXXVIII)

in which $L^7$ represents a hydrogen atom and $R^{5'}$ represents a $C_1$–$C_3$ alkyl group optionally substituted as defined for $R^5$ in formula (I) and P is a suitable protecting group, wherein the compound of formula (XXXVIII) is pre-treated with a hydroborating agent, followed by removal of the protecting group, P, in a deprotection reaction, then by an oxidation reaction and then by reaction with a compound of formula (XIII) as defined in (i) above under reductive amination conditions; or (xii) when n is 0 and $R^5$ is $(CH_2)_2$, reacting a compound of formula (XV), (XVI) or (XVII) as defined in (iv) above with a compound of formula

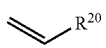

(XXXIX)

wherein $R^{20}$ represents a suitable leaving group, in the presence of a suitable catalyst, followed by reaction with a compound of formula (XIII) as defined in (i) above; or (xiii) when n is 0 and $R^5$ is $CH_2$, reacting a compound of formula (XV), (XVI) or (XVII) as defined in (iv) above with a compound of formula (XXXIX) as defined in (xii) above, followed by an oxidation reaction and then by reaction with a compound of formula (XIII) as defined in (i) above under reductive amination conditions;

and optionally after (i), (ii), (iii), (iv), (v), (vi), (vii), (viii), (ix), (x), (xi), (xii) or (xiii) carrying out one or more of the following:
  converting the compound obtained to a further compound according to claim 1
  forming a pharmaceutically acceptable salt or solvate of the compound.

13. An intermediate compound of formula

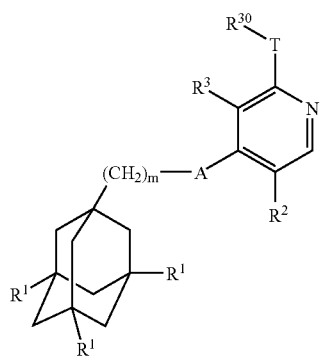

(IA)

wherein T represents —C≡C— or —CH$_2$CH$_2$—;

$R^{30}$ represents —CHO, —CH$_2$OP$^1$ or a group of formula

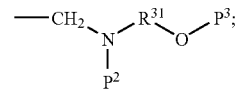

$P^1$ represents a hydrogen atom or a suitable protecting group;

$P^2$ represents a suitable protecting group;

$P^3$ represents a suitable protecting group;

$R^{31}$ represents a $C_1$–$C_5$ alkyl group; and m, A, $R^1$, $R^2$ and $R^3$ are as defined in claim 1.

14. An intermediate compound according to claim 13, wherein:
  m represents 1;
  A represents NHC(O);
  each $R^1$ represents a hydrogen atom;
  $R^2$ represents a halogen atom; and
  $R^3$ represents a hydrogen atom.

15. A pharmaceutical composition comprising a compound of formula (I) or a pharmaceutically acceptable salt or solvate thereof as claimed in claim 1 in association with a pharmaceutically acceptable adjuvant, diluent or carrier.

16. A process for the preparation of a pharmaceutical composition as claimed in claim 15 which comprises mixing a compound of formula (I) or a pharmaceutically acceptable salt or solvate thereof as defined in claim 1 with a pharmaceutically acceptable adjuvant, diluent or carrier.

17. A method of treating rheumatoid arthritis in a patient, the method comprising;
  administering a compound of formula (I) or a pharmaceutically acceptable salt or solvate thereof as claimed in claim 1 in the treatment of rheumatoid arthritis.

18. A method of treating an obstructive airways disease in a patient, the method comprising;
  administering a compound of formula (I) or a pharmaceutically acceptable salt or solvate thereof as claimed in claim 1 in the treatment of an obstructive airways disease.

19. The method according to claim 18, wherein the obstructive airways disease is asthma or chronic obstructive pulmonary disease.

* * * * *